(12) United States Patent
Sawant et al.

(10) Patent No.: US 12,370,379 B2
(45) Date of Patent: *Jul. 29, 2025

(54) SYSTEM AND METHOD FOR RADIATION THERAPY USING SPATIAL-FUNCTIONAL MAPPING AND DOSE SENSITIVITY OF BRANCHING STRUCTURES AND FUNCTIONAL SUB-VOLUMES

(71) Applicants: University Of Maryland, Baltimore, Baltimore, MD (US); The Board of Regents of the University of Texas System, Austin, TX (US); Broncus Medical Inc., San Jose, CA (US)

(72) Inventors: Amit Sawant, Columbia, MD (US); Robert Timmerman, Westlake, TX (US); Yulong Yan, Plano, TX (US); Henky Wibowo, San Jose, CA (US); Esther Vicente, Baltimore, MD (US); Arezoo Modiri, Rosedale, MD (US)

(73) Assignees: University Of Maryland, Baltimore, Baltimore, MD (US); The Board of Regents of the University of Texas System, Austin, TX (US); Broncus Medical Inc., San Jose, CA (US)

( * ) Notice: Subject to any disclaimer, the term of this patent is extended or adjusted under 35 U.S.C. 154(b) by 239 days.

This patent is subject to a terminal disclaimer.

(21) Appl. No.: 18/165,540

(22) Filed: Feb. 7, 2023

(65) Prior Publication Data
US 2023/0181930 A1    Jun. 15, 2023

Related U.S. Application Data

(63) Continuation of application No. 16/853,304, filed on Apr. 20, 2020, now Pat. No. 11,633,623.
(Continued)

(51) Int. Cl.
| | | |
|---|---|---|
| A61N 5/10 | (2006.01) | |
| G06T 7/00 | (2017.01) | |
| G06T 7/11 | (2017.01) | |

(52) U.S. Cl.
CPC ......... *A61N 5/1031* (2013.01); *A61N 5/1064* (2013.01); *A61N 5/1077* (2013.01);
(Continued)

(58) Field of Classification Search
CPC .............. G06T 7/0012; G06T 7/11; G06T 2207/10076; G06T 2207/10088;
(Continued)

(56) References Cited

U.S. PATENT DOCUMENTS

| | | | |
|---|---|---|---|
| 11,633,623 B2* | 4/2023 | Sawant | A61N 5/1064 378/65 |
| 2013/0197878 A1* | 8/2013 | Fiege | G06F 30/20 703/2 |

(Continued)

OTHER PUBLICATIONS

Vedam, S.S., et al., "Acquiring a four-dimensional computed tomography dataset using an external respiratory signal," Phys Med Biol. 2003, pp. 45-62, vol. 48.
(Continued)

Primary Examiner — Wassim Mahrouka
(74) Attorney, Agent, or Firm — Wolter Van Dyke Davis, PLLC; Eugene J. Molinelli; Cian G. O'Brien

(57) ABSTRACT

A method and apparatus for radiation therapy using functional measurements of branching structures. The method includes determining a location of each voxel of a plurality of voxels in a reference frame of a radiation device. The method further includes obtaining measurements that indicate a tissue type at each voxel. The method further includes determining a subset of the voxels based on an anatomical parameter of a respective branching structure of a set of branching structures indicated by the measurements. The
(Continued)

method further includes determining a subset of the voxels that enclose an organ-at-risk (OAR) volume. The method further includes determining a value of a utility measure at each voxel. The method further includes determining a series of beam shapes and intensities which minimize a value of an objective function based on a computed dose delivered to each voxel and the utility measure for that voxel summed over all voxels.

20 Claims, 59 Drawing Sheets

Related U.S. Application Data

(60) Provisional application No. 62/904,096, filed on Sep. 23, 2019, provisional application No. 62/836,176, filed on Apr. 19, 2019, provisional application No. 62/836,174, filed on Apr. 19, 2019.

(52) U.S. Cl.
CPC .............. *G06T 7/0012* (2013.01); *G06T 7/11* (2017.01); *A61N 5/1039* (2013.01); *A61N 5/1045* (2013.01); *A61N 2005/1055* (2013.01); *G06T 2207/10076* (2013.01); *G06T 2207/10088* (2013.01); *G06T 2207/30061* (2013.01)

(58) Field of Classification Search
CPC ........ G06T 2207/30061; A61N 5/1031; A61N 5/1064; A61N 5/1077; A61N 5/1039; A61N 5/1045; A61N 2005/1055
See application file for complete search history.

(56) References Cited

U.S. PATENT DOCUMENTS

| | | | |
|---|---|---|---|
| 2016/0023018 A1 | 1/2016 | Zhang et al. | |
| 2017/0246477 A1* | 8/2017 | Zhang | A61N 5/1047 |
| 2018/0345042 A1 | 12/2018 | Voronenko et al. | |
| 2019/0054320 A1 | 2/2019 | Owens et al. | |

OTHER PUBLICATIONS

Vinogradskiy, Y., et al., "Use of 4-dimensional computed tomography-based ventilation imaging to correlate lung dose and function with clinical outcomes." Int J Radiat Oncol Biol Phys 2013, pp. 366-371, vol. 86, No. 2.
Ward, M.P., et al., "A flexible platform for biofeedback-driven control and personalization of electrical nerve stimulation therapy,". IEEE Trans Neura Syst Rehabil Eng 2014, pp. 475-484, vol. 23, No. 3.
Wisnivesky, J.P., et al., "Radiation therapy for the treatment of unresected stage I-II non-small cell lung cancer," Chest 2005, pp. 1461-1467, vol. 128, No. 3.
Xing et al. "Inverse Planning for Functional Image-Guided Intensity-Modulated Radiation Therapy." Physics in Medicine and Biology, 47, 2002, pp. 3567-3578 (Year: 2002).
Yamamoto, T., et al., "Impact of four-dimensional computed tomography pulmonary ventilation imaging-based functional avoidance for lung cancer radiotherapy," Int J Radiat Oncol Biol Phys 2011, pp. 279-288, vol. 79, No. 1.
Yamamoto, T., et al., "Investigation of four-dimensional computed tomography-based pulmonary ventilation in-aging in patients with emphysematous lung regions," Phys Med Biol 2011, pp. 2279-2298, vol. 56.
Yaremko, B.P., et al., "Reduction of normal lung irradiation in locally advanced non-small-cell lung cancer patients, using ventilation images for functional avoidance," Int J Radiat Oncol Biol Phys 2007, pp. 562-571, vol. 68, No. 2.
Zhang, J., et al., "Radiation-induced reductions in regional lung perfusion: 0.1-12 year data from a prospective clinical study," Int J Radiat Oncol Biol Phys 2010, pp. 425-432, vol. 76, No. 2.
Adebahr, S., et al., "LungTech, an EORTC phase II trial of stereotactic body radiotherapy for centrally located lung tumours: A clinical perspective," Br J Radiol 2015, pp. 1-15, vol. 88, No. 1051.
Admiraal, M.A., et al., "Dose calculations accounting for breathing motion in stereotactic lung radiotherapy based on 4D-CT and the internal target volume," Radiotherapy and Oncology 2008, pp. 55-60, vol. 86, No. 1.
Baker, R., et al., "Clinical and dosimetric predictors of radiation pneumonitis in a large series of patients treated with stereotactic body radiation therapy to the lung," Int J Radiat Oncol Biol Phys 2013, pp. 190-195, vol. 85, No. 1.
Balasubramanian, A., et al., "Predictive modeling of respiratory tumor motion for real-time prediction of baseline shifts," Phys Med Biol. 2017, pp. 1791-1809, vol. 62, No. 5.
Bortfeld, T., et al. "Effects of motion on the total dose distribution," Semin Radiat Oncol. 2004, pp. 41-51, vol. 14, No. 1.
Chang, J.Y., et al., "Stereotactic ablative radiotherapy versus lobectomy for operable stage I non-small-cell lung cancer: A pooled analysis of two randomised trials," Lancet Oncol 2015, pp. 630-637, vol. 16, No. 6.
Chi, A., et al., "Systemic review of the patterns of failure following stereotactic body radiation therapy in early-stage non-small-cell lung cancer: Clinical implications," Radiother Oncol 2010, pp. 1-11, vol. 94.
Chmura, S.J., et al., Stereotactic radiotherapy for pulmonary metastases. Semin Thorac Cardiovasc Surg 2013, pp. 292-299, vol. 25, Issue 4.
Christian, J.A., et al., "The incorporation of SPECT functional lung imaging into inverse radiotherapy planning for non-small cell lung cancer," Radiother Oncol 2005, pp. 271-277, vol. 77.
Farr, K.P., et al., "Inclusion of functional in-formation from perfusion SPECT improves predictive value of dose-volume parameters in lung toxicity outcome after radiotherapy for non-small cell lung cancer: A prospective study," Radiother Oncol 2015, pp. 9-16, vol. 117.
Faught, A.M., et al., "Evaluating the toxicity reduction with computed tomographic ventilation functional avoidance radiation therapy," Int J Radiat Oncol Biol Phys 2017, pp. 325-333, vol. 99, No. 2.
Faught, A.M., et al., "Evaluating which dose-function metrics are most critical for functional-guided radiation therapy," Int J Radiat Oncol Biol Phys 2017, pp. 202-209, vol. 99, No. 1.
Ford, E C., et al., "Respiration-correlated spiral ct: A method of measuring respiratory-induced anatomic motion for radiation treatment planning," Med Phys. 2003, pp. 88-97, vol. 30, No. 1.
Ge, H., et al., "Quantification and minimization of uncertainties of internal target volume for stereotactic body radiation therapy of lung cancer," Int J Radiat Oncol Biol Phys. 2013, pp. 438-443, vol. 85, No. 2.
Glide-Hurst, C.K., et al., "A simplified method of four-dimensional dose accumulation using the mean patient density representation," Med Phys. 2008, pp. 5269-5277, vol. 35, No. 12.
Graham, M.W., et al., "Robust 3-D airway tree segmentation for image-guided peripheral bronchoscopy," IEEE Trans Med Imaging 2010, pp. 982-997, vol. 29, No. 4.
Hagan, A., et al., "Multi-GPU configuration of 4D intensity modulated radiation therapy inverse planning using global optimization," Physics in Medicine & Biology 2018, pp. 1-21, vol. 63, No. 2.
Heath, E. and Seuntjens, J., "A direct voxel tracking method for four-dimensional monte carlo dose calculations in deforming anatomy," Med Phys 2006, pp. 434-445, vol. 33, No. 2.
Kadoya, N., et al., "Multi-institutional validation study of commercially available deformable image registration software for thoracic images." Int J Radiat Oncol Biol Phys 2016, pp. 422-431, vol. 96, No. 2.
Kang, K.H., et al., "Complications from stereotactic body radiotherapy for lung cancer," Cancer (Basel). 2015, pp. 981-1004, vol. 7.
Karlsson, K., et al., "Retrospective cohort study of bronchial doses and radiation-induced atelectasis after stereotactic body radiation

(56) References Cited

OTHER PUBLICATIONS therapy of lung tumors located close to the bronchial tree," Int J Radiat Oncol Biol Phys 2013, pp. 590-595, vol. 87, No. 3.

Kazemzadeh, N., et al., "Virtual bronchoscopy-guided treatment planning to map and mitigate radiation-induced airway injury in lung sabr," Int J Radiat Oncol Biol Phys. 2018, pp. 210-218, vol. 102, No. 1.

Keall, P., "4-dimensional computed tomography imaging and treatment planning," Semin Radiat Oncol. 2004, pp. 81-90, vol. 14, No. 1.

Keall, P.J., et al., "The management of respiratory motion in radiationoncology report of aapm task group 76," Med Phys. 2006, pp. 3874-3900, vol. 33, No. 10.

Kelsey, C.R., et al., "Radiation-induced narrowing of the tracheobronchial tree: An in-depth analysis," Lung Cancer 2006, pp. 111-116, vol. 52.

Kim, J., et al., "To gate or not to gate—dosimetric evaluation comparing gated vs. Itv-based methodologies in stereotactic ablative body radiotherapy (SAbR) treatment of lung cancer," Radiat Oncol. 2016, pp. 1-11, DOI: 10.1186/s13014-0699-2.

Kimura, T., et al., "Phase I study of stereotactic body radiation therapy for centrally located stage IA non-small cell lung cancer (JROSG10-1)," Int J Clin Oncol 2017, pp. 849-856, vol. 33.

Kipritidis, J., et al., "Validating and improving CT ventilation imaging by correlating with ventilation 4D-PEI/CT using 68Ga-labeled nanoparticles," Med Phys. 2014, pp. 1-40, vol. 41, No. 1, DOI: 10.1118/1.4856055.

Kong, F.M., et al., et al., "High-dose radiation improved local tumor control and overall survival in patients with inoperable/unresectable non-small-cell lung cancer: Long-term results of a radiation dose escalation study," Int J Radiat Oncol Biol Phys 2005, pp. 324-333, vol. 63, No. 2.

Lavrenkov, K., et al., "A potential to reduce pulmonary toxicity: The use of perfusion SPECT wipth IMRT for functional lung avoidance in radiotherapy of non-small cell lung cancer." Radiother Oncol 2007, pp. 156-162, vol. 83.

Marks, L.B., et al., "Radiation dose-volume effects in the lung," Int J Radiat Oncol Biol Phys 2010, pp. S70-S76, vol. 76, No. 3.

Matsuo, Y., et al., "Dose-volume metrics associated with radiation pneumonitis after stereotactic body radiation therapy for lung cancer," Int J Radiat Oncol Biol Phys 2012, pp. e545-e549, vol. 83, No. 4.

Matsuo, Y., et al., "Preliminary report of late recurrences, at 5 years or more, after stereotactic body radiation therapy for non-small cell lung cancer." J Thorac Oncol 2012, pp. 453-456, vol. 7, No. 2.

McGuire, S.M., et al., "A methodology for using SPECT to reduce intensity-modulated radiation therapy (IMRT) dose to functioning lung," Int J Radiat Oncol Biol Phys 2006, pp. 1543-1552, vol. 66, No. 5.

Meng, X., et al., "Changes in functional lung regions during the course of radiation therapy and their potential impact on lung dosimetry for non-small cell lung cancer," Int J Radiat Oncol Biol Phys 2014, pp. 145-151, vol. 89, No. 1.

Mexner, V, et al., "Effects of respiration-induced density variations on dose distributions in radiotherapy of lung cancer," Int J Radiat Oncol Biol Phys. 2009, pp. 1266-1275, vol. 74, No. 4.

Miller, K.L., et al., "Bronchial stenosis: An underreported complication of high-dose external beam radiotherapy for lung cancer?," Int J Radiat Oncol Biol Phys 2005, pp. 64-69, vol. 61, No. 1.

Modiri, A, et al., "Inversed-planned respiratory phase gating in lung conformal radiation therapy," Int J Radiat Oncol Biol Phys. 2017, pp. 317-324, No. 99, No. 2.

Modiri, A., et al. "Inverse 4D conformal planning for lung SBRT using particle swarm optimization," Phys Med Biol 2016, pp. 6181-6202, vol. 61, No. 16.

Ochs, M., et al., "The No. of alveoli in the human lung," Am J Respir Crit Care Med 2004, pp. 120-124, vol. 169.

Park, C., et al., "Universal survival curve and single fraction equivalent dose: Useful tools in understanding potency of ablative radiotherapy," Int J Radiat Oncol Biol Phys 2008, pp. 847-852, vol. 70, No. 3.

Rosu, M. and Hugo, G.D., "Advances in 4D radiation therapy for managing respiration: Part II—4D treatment planning," Z Med Phys. 2012, pp. 272-280, vol. 22, No. 4.

Shioyama, Y., et al., "Preserving functional lung using perfusion imaging and intensity-modulated radiation therapy for advanced-stage non-small cell lung cancer," Int J Radiat Oncol Biol Phys 2007, pp. 1349-1358, vol. 68, No. 5.

Siva, S., et al., "Stereotactic radiotherapy for pulmonary oligometastases: A systematic review," J Thorac Oncol 2010, pp. 1091-1099, vol. 5, No. 7.

Song, S.Y., et al., "Fractionated stereotactic body radiation therapy for medically inoperable stage I lung cancer adjacent to central large bronchus," Lung Cancer. 2009, pp. 89-93, vol. 66, No. 1.

Theuws, J.C., et al., "Dose-effect relations for early local pulmonary injury after irradiation for malignant lymphoma and breast cancer," Radiother Oncol 1998, pp. 33-43, vol. 48.

Timmerman, R.D., et al., "Excessive toxicity when treating central tumors in a phase II study of stereotactic body radiation therapy for medically inoperable early-stage lung cancer," J Clin Oncol 2006, pp. 4833-4839, vol. 24, No. 30.

Timmerman, R.D., et al., Long-term results of RTOG 0236: A phase II trial of stereotactic body radiation therapy (SBRT) in the treatment of patients with medically inoperable stage I non-small cell lung cancer. Int J Radiat Oncol Biol Phys 2014, p. S30, vol. 90.

Van Hoorn, J.E., et al., "Bronchoscopic manifestations of airway toxicity after radiotherapy," Clin Lung Cancer. 2018, pp. e875-e878, vol. 19, No. 6.

Bezjak, A., et al., Efficacy and toxicity analysis of NRG oncology/RTOG 0813 trial of stereotactic body radiation therapy (SBRT) for centrally located non-small cell lung cancer (NSCLC), Int J Radiat Oncol Biol Phys 2016, pp. S8, vol. 96, Issue 2.

* cited by examiner

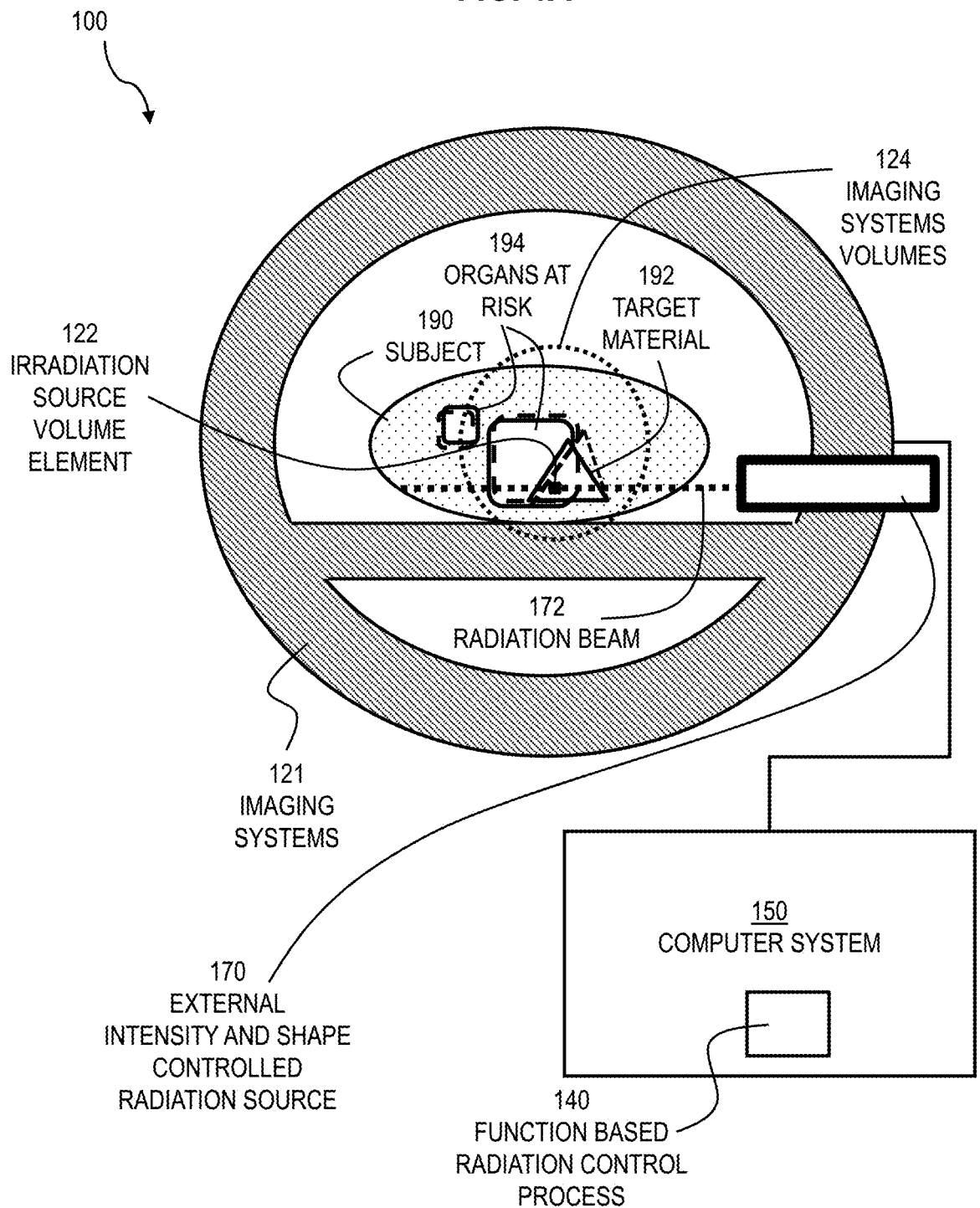

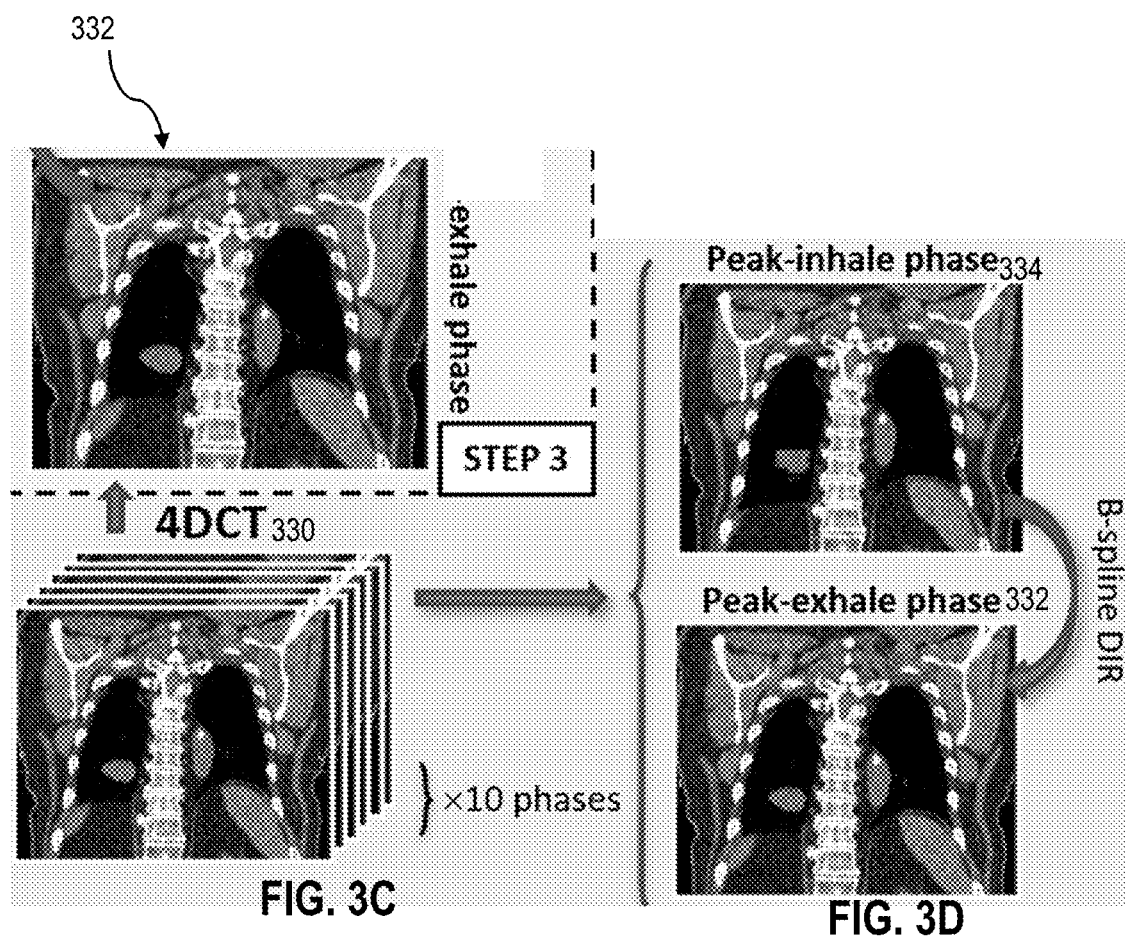
FIG. 3C
FIG. 3D
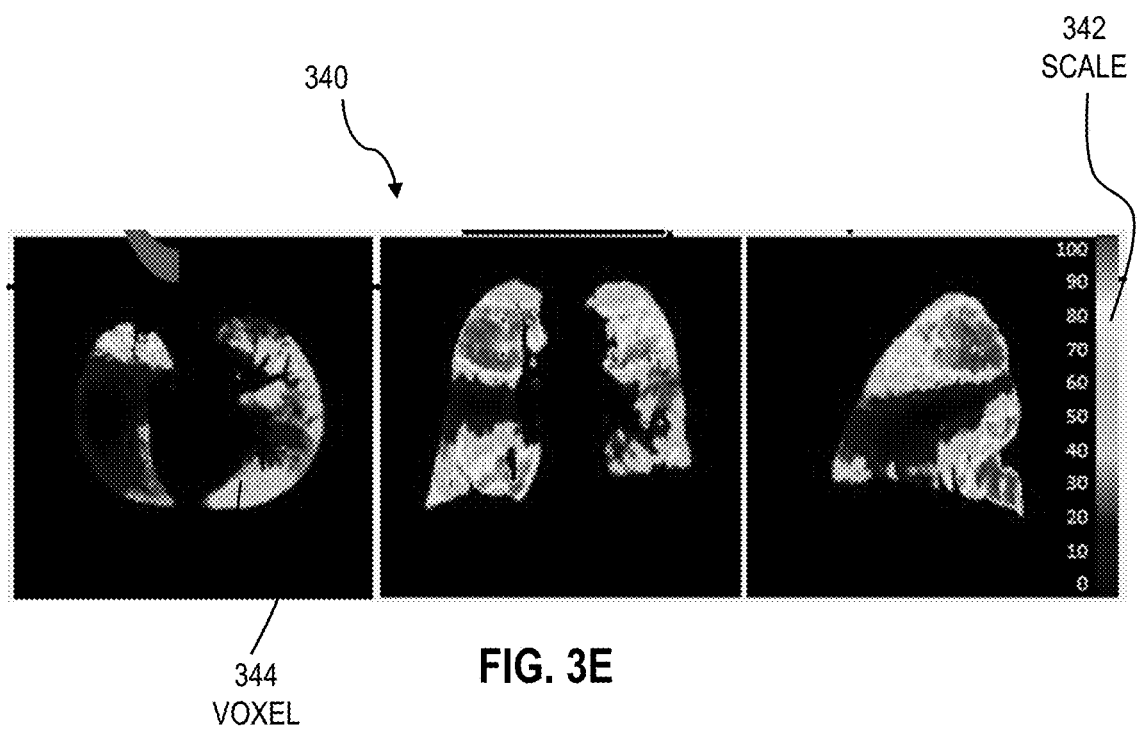
FIG. 3E

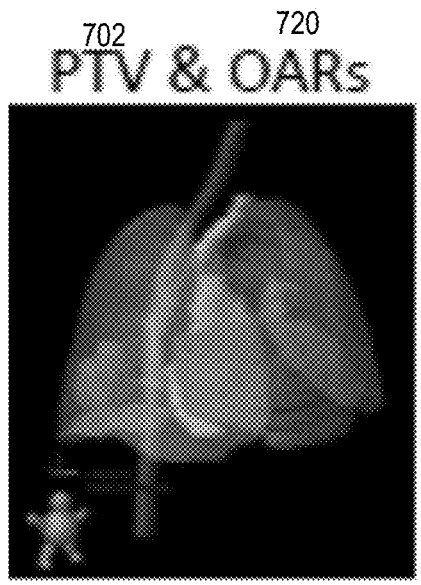
FIG. 10A
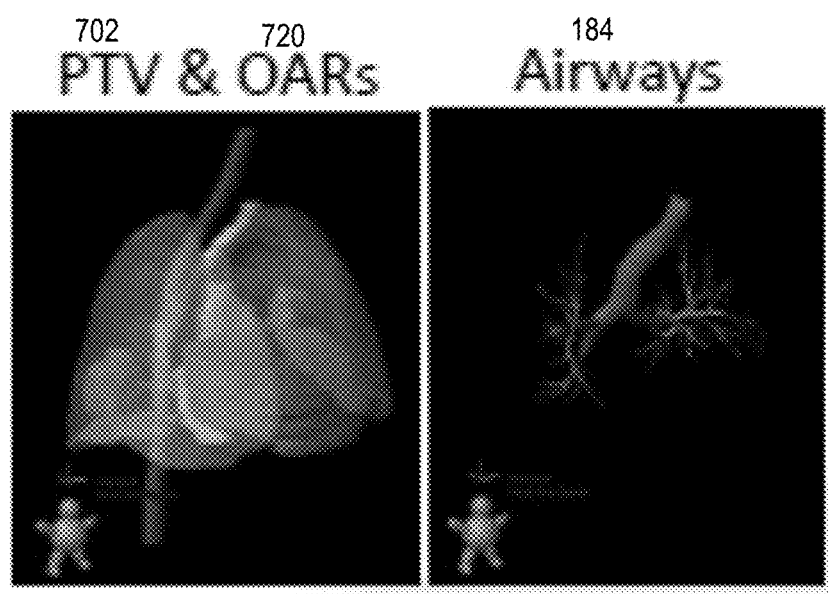
FIG. 10B
FIG. 10C

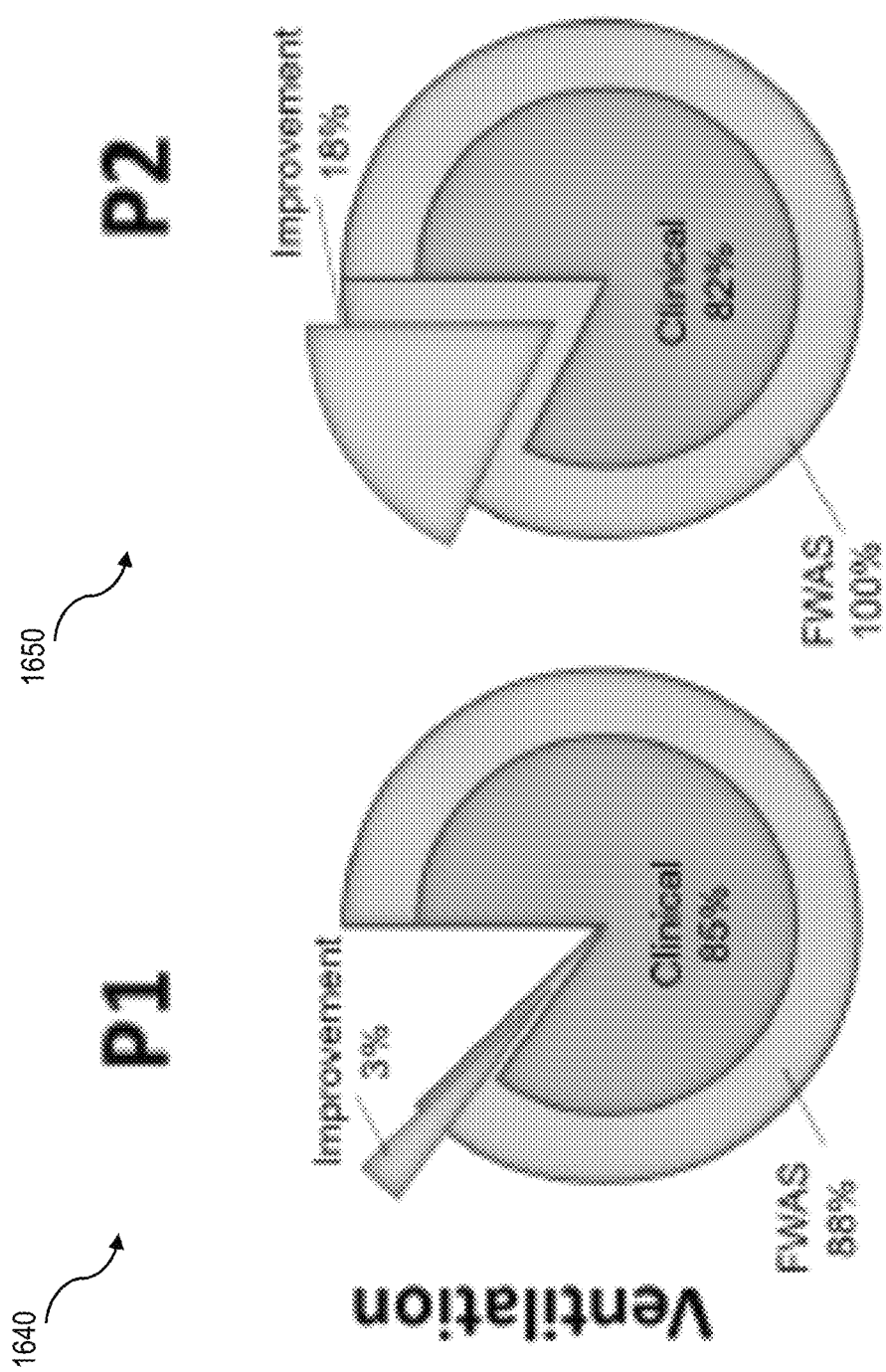

SYSTEM AND METHOD FOR RADIATION THERAPY USING SPATIAL-FUNCTIONAL MAPPING AND DOSE SENSITIVITY OF BRANCHING STRUCTURES AND FUNCTIONAL SUB-VOLUMES

CROSS-REFERENCE TO RELATED APPLICATIONS

This application is a continuation of U.S. patent application Ser. No. 16/853,304, filed Apr. 20, 2020, which claims benefit of Provisional Application No. 62/836,174, filed Apr. 19, 2019, Provisional Application No. 62/836,176 filed Apr. 19, 2019, and Provisional Application No. 62/904,096 filed Sep. 23, 2019, the entire contents of each are hereby incorporated by reference as if fully set forth herein, under 35 U.S.C. § 119(e).

STATEMENT OF GOVERNMENTAL INTEREST

This invention was made with government support under Grant Number CA202761 awarded by National Institutes of Health. The government has certain rights in the invention.

BACKGROUND

Radiotherapy is a treatment for cancer patients involving the use of high-energy radiation. When high-energy radiation is delivered to a subject, it kills cells in the body. Although the high-energy radiation kills tumor cells in the subject's body, it may also kill normal tissue cells and tissue cells of organs-at-risk (OARs) that lie in the radiation field. Thus, the goal of conventional radiotherapy is to deliver a sufficient radiation dose to the tumor to kill the tumor cells while minimizing the radiation dose delivered to the normal tissue cells and OAR tissue cells that surround the tumor.

SUMMARY

While some methods for radiation therapy are known which spatially map functional regions of the lungs and generate avoidance radiation therapy (RT) plans that preferentially avoid irradiating high-functioning lung regions, it is here recognized that these known methods do not account for branching structures (e.g. airway tree and pulmonary vasculature) of the anatomy that are especially vulnerable to radiation damage. In contrast to functional sub-volumes, which function as "parallel structures" (i.e., the structure would still maintain partial function if there were radiation damage to a fractional portion of its volume), airways and vessels function as "branching structures" (i.e., damage to an airway or blood vessel segment means that all the downstream airways or vessels, and the corresponding functional lung volumes supported by them are rendered dysfunctional). Thus, these prior methods of radiation therapy may cause irreparable damage to branching structures such as the airways and pulmonary vessels responsible for servicing the high-functioning lung regions. Here are described improved methods which considers both the branching structures and the high value regions serviced by them, such as high-functioning lung regions (e.g. sub-lobar volumes which contain numerous alveoli), the airways responsible for airflow delivery to these high-functioning lung regions and the network of pulmonary vessels that carry oxygenated and deoxygenated blood from and to alveoli, respectively.

While some prior methods for radiation therapy are known which perform dose estimations for various tissue types (e.g. target, organ-at-risk, etc.) to account for breathing motion, such methods are not suitable for many branching structures. In one example, these prior methods involve measuring the tissue types over multiple phases of a breathing cycle and then calculating a maximum volume (or an average volume) of the tissue type among all breathing phases when computing dose distributions for the RT plan. Thus, here is described an improved method which computes a dose to the tissue type at each phase of the breathing cycle separately and then combines the computed dose at each phase of the breathing cycle taking into account the anatomical variations across breathing phases in order to compute dose distributions for the RT plan.

In a first set of embodiments, a method is provided for radiation therapy using functional measurements of branching structures. The method includes determining a location of each voxel of a plurality of voxels in a reference frame of a radiation device that emits a beam of radiation with controlled intensity and beam cross sectional shape. The method further includes obtaining measurements that indicate a tissue type inside a subject at each voxel of the plurality of voxels based on an imaging device. The method further includes determining a first subset of the plurality of voxels that enclose a target volume to be irradiated with a therapeutic dose of radiation by the radiation device. The method further includes determining a plurality of second subsets of the plurality of voxels, where each second subset is based on an anatomical parameter of a respective branching structure of a set of branching structures indicated by the measurements. The method further includes determining a third subset of the plurality of voxels that enclose an organ-at-risk (OAR) volume and the third subset is associated with one or more second subsets. The method further includes determining a value of a utility measure at each voxel of the plurality of voxels. The method further includes determining data that indicates a series of beam shapes and intensities which minimize a value of an objective function that is based on a computed dose delivered to each voxel and the utility measure for that voxel summed over all voxels. The method further includes controlling the radiation device to deliver the series of beam shapes and intensities based on the determined data.

In a second set of embodiments, a computer-readable medium carrying one or more sequences of instructions is provided, where execution of the one or more sequences of instructions by one or more processors causes the one or more processors to perform the step of receiving measurements from an imaging device that relate to tissue type inside a subject at each voxel of a plurality of voxels. Additionally, execution of the one or more sequences of instructions further causes the processor to determine a first subset of the plurality of voxels that enclose a target volume. Additionally, execution of the one or more sequences of instructions further causes the processor to determine a plurality of second subsets of the plurality of voxels, where each second subset is based on an anatomical parameter of a respective branching structure of a set of branching structures indicated by the measurements. Additionally, execution of the one or more sequences of instructions further causes the processor to determine a third subset of the plurality of voxels that enclose an OAR volume, where the third subset is associated with one or more second subsets. Additionally, execution of the one or more sequences of instructions further causes the processor to determine a value of a utility measure at each voxel of the plurality of voxels. Additionally, execution of the one or more sequences of instructions further causes the processor to determine data that indicates a series of beam shapes and intensities from a radiation device which minimize a value of an objective function that is based on a computed dose delivered to each voxel and the utility measure for that voxel summed over all voxels. Additionally, execution of the one or more sequences of instructions further causes the processor to control the radiation device to deliver the series of beam shapes and intensities based on the determined data.

In a third set of embodiments, a system is provided for radiation therapy using functional measurements of branching structures. The system includes a radiation device to emit a beam of radiation with controlled intensity and beam cross sectional shape in each voxel of a plurality of voxels in a reference frame of the radiation device. The system further includes one or more imaging devices to obtain one or more measurements that relate to tissue type inside a subject at each voxel of the plurality of voxels. The system further includes at least one processor and at least one memory including one or more sequence of instructions. The memory and the sequence of instructions are configured to, with the processor, cause the processor to receive the one or more measurements from the one or more imaging devices to determine a first subset of the plurality of voxels that enclose a target volume to be irradiated by the radiation device. The memory and the sequence of instructions are configured to, with the processor, cause the processor to determine a plurality of second subsets of the plurality of voxels, where each second subset is based on an anatomical parameter of a respective branching structure of a set of branching structures indicated by the measurements. The memory and the sequence of instructions are configured to, with the processor, cause the processor to determine a third subset of the plurality of voxels that enclose an OAR volume and the third subset is associated with one or more second subsets. The memory and the sequence of instructions are configured to, with the processor, cause the processor to determine a value of a utility measure at each voxel of the plurality of voxels. The memory and the sequence of instructions are configured to, with the processor, cause the processor to determine data that indicates the controlled intensity and beam cross sectional shape in each voxel that minimize a value of an objective function that is based on a computed dose delivered to each voxel and the utility measure for that voxel summed over all voxels. The memory and the sequence of instructions are configured to, with the processor, cause the processor to control the radiation device to deliver the series of beam shapes and intensities based on the determined data.

Still other aspects, features, and advantages are readily apparent from the following detailed description, simply by illustrating a number of particular embodiments and implementations, including the best mode contemplated for carrying out the invention. Other embodiments are also capable of other and different features and advantages, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

Embodiments are illustrated by way of example, and not by way of limitation, in the figures of the accompanying drawings in which like reference numerals refer to similar elements and in which:

FIG. 1A is a block diagram that illustrates an example system for radiation therapy using voxel based functional measurements of organs-at-risk (OAR), according to an embodiment;

FIG. 3C is an image that illustrates an example of a four-dimensional computed tomography (4DCT) of the subject including a CT image at a peak exhalation phase, according to an embodiment;

FIG. 3D is an image that illustrates an example of CT images of the 4DCT of FIG. 3C at the peak inhale phase and peak exhale phase, according to an embodiment;

FIG. 3E is an image that illustrates an example of a ventilation map based on the CT images of FIG. 3D at the peak inhale and peak exhale phases, according to an embodiment;

FIG. 10A is an image that illustrates an example of a PTV and OAR within a subject, according to a conventional clinical method;

FIGS. 10B and 10C are images that illustrates an example of a PTV and OARs including a branching structure within a subject, according to an embodiment;

FIGS. 16E through 16H are pie charts that illustrate an example of the preservation of ventilation for a probability of no airway collapse of 95% for different subjects based on FIGS. 15E through 15H, according to embodiments;

DETAILED DESCRIPTION

Figure 1B:
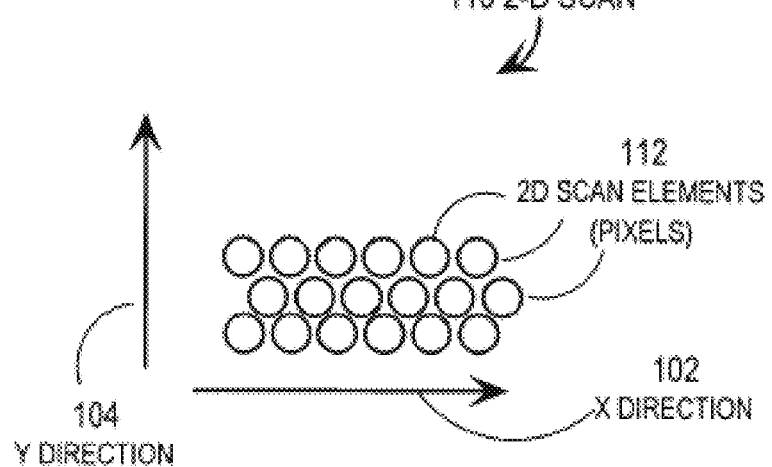
FIG. 1B is a block diagram that illustrates example scan elements in a 2D scan, such as one scanned image from a CT scanner.

A method and apparatus are described for radiation therapy using functional measurements of branching structures. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus, a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about X" implies a value in the range from 0.5× to 2×, for example, about 100 implies a value in a range from 50 to 200. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Some embodiments of the invention are described below in the context of radiation therapy for a mass in or near an OAR, such as the heart, spinal cord or esophagus. In some embodiments, the OAR is branching structures (e.g. airways, pulmonary vessels, etc.). For purposes of this description, "branching structure" is an OAR characterized by longitudinal segments of wide diameter in fluid connection to one or more longitudinal segments of narrower diameter and whose functionality is affected by all longitudinal segments upstream. For purposes of this description, "dependent volume" or "OAR volume" means an OAR whose functionality is affected by the functionality of one or more upstream branching structure OARs. In some embodiments, the branching structures are one or more airway segments of a bronchial tree whose functionality affects the functionality of downstream branches and terminal lung volumes (e.g. alveoli). In an example embodiment, if one segment of the bronchial tree is irreversibly damaged, all downstream airway segments and the volumetric regions of functional lung served by these segments are rendered defunct. In other embodiments, the OAR is a structure such as the normal lung or liver, where damage to one or more voxels within the OAR adversely impacts the functionality of at least a portion of the OAR. Additionally, in other examples, other OARs such as the brain, spinal cord, heart, esophagus, brachial plexus, kidney and neck are applicable to the invention.

1. OVERVIEW

A glossary of terms is provided below in Table 1 with a description of various acronyms used herein:

TABLE 1

| Acronym | Description |
|---|---|
| a.u. | Arbitrary units |
| BED | Biologically effective dose |
| BHCT | Breath-hold CT |
| BM | Breathing model |
| CBCT | Cone beam CT |
| CI | Confidence interval |
| CRT | Conformal radiation therapy |
| CT | Computed tomography |
| $CT_{AVG}$ | Maximum intensity projection of the 4DCT |
| $CT_{MIP}$ | Average CT generated by averaging all the 3DCT phases of the 4DCT |
| CTV | Clinical target volume |
| CTVI | CT ventilation imaging |
| DICOM | Digital imaging and communications |
| DIR | Deformable image registration |
| $D_{max}$ | Maximum voxel dose |
| $D_{mean}$ | Average dose |
| DVF(s) | Deformation vector field(s) |
| $D_x$ (such as in $D_{0.01cc}$) | Minimum voxel dose received within x volume |
| EX | Peak-exhalation phase |
| FWAS | Functionally Weighted Airway Sparing |
| GTV | Gross tumor volume |
| HR | Hazard ratio |
| HR | High resolution |
| HU | Hounsfield units |
| IN | Peak-inhalation phase |
| IMRT | Intensity modulated radiation therapy |
| IRB | Institutional review board |
| ITV | Internal target volume |
| Jac | Jacobian |
| LDCT | Low-dose CT |
| LLL | Left lower lobe |
| LUL | Left upper lobe |
| LUT | Look-up table |
| MU | Monitor unit |
| MRI | Magnetic resonance imaging |
| NSCLC | Non-small cell lung cancer |
| OAR(s) | Organ(s) at risk |
| PET | Positron emission tomography |
| PSO | Particle swarm optimization |
| PTV | Planning target volume |
| RLL | Right lower lobe |
| RML | Right middle lobe |
| RT | Radiation therapy |
| RUL | Right upper lobe |
| SAbR | Stereotactic ablative radiotherapy |
| SBRT | Stereotactic body radiation therapy |
| SPECT | Single Photon Emission Computed Tomography |
| TPS | Treatment planning system |
| VMAT | Volumetric modulated arc therapy |
| $V_x$ (such as in $V_{13}$, V20 and $V_5$) | Volume receiving ≥ x Gray of radiation |

FIG. 1A is a block diagram that illustrates an example system 100 for radiation therapy using voxel based functional measurements of OARs, according to an embodiment. For purposes of illustration, a living subject 190 is depicted, but is not part of the system 100. One or more imaging systems 121 are provided, to scan images of the subject 190 within an imaging systems volume 124 that encompasses part of the subject 190. In an example embodiment, the volume 124 may encompass the entire subject 190. The imaging systems 121 are non-invasive and obtain cross-sectional images that are axially stacked to generate imaging data of the volume 124. In an example embodiment, the imaging system 121 is a first imaging device that obtains first measurements that relate to tissue type inside the volume 124. For example, the first imaging device is an X-ray Computed tomography (CT) scanner, a nuclear magnetic resonance imagery (MRI) scanner or a four-dimensional computed tomography (4DCT), a Single Photon Emission Computed Tomography (SPECT) or Computed Tomography Ventilation Imaging (CTVI) functionality imaging system or a Magnetic Resonance Imaging (MRI) based ventilation/perfusion system. The imaging systems 121 can be operated at different times, to generate different measurements of the tissue type inside the volume 124.

As illustrated in FIG. 1A, a target material 192 indicated by a triangle is identified within the subject 190. In an example embodiment, the target material 192 includes tumor cells. During movement phases of the subject 190, such as during a breathing phase or heartbeats, the target material 192 shifts from a nominal position to a secondary position indicated by the triangle with the broken line. Thus, at any given instance in time, the actual position of the target material 192 may not be the nominal position, FIG. 1A depicts the movement of target material 192 between the nominal position (solid line) and secondary position (dashed line). Additionally, a pair of OARs 194 are positioned within the subject 190. During movement phases of the subject 190, such as during a breathing phase or heartbeats, the OARs 194 shift from a nominal position to a secondary position indicated by the squares with the broken lines. The region of the volume 124 that is not occupied by the target material 192 or the OAR 194 is occupied by tissues in a category called normal tissue.

As illustrated in FIG. 1A, the system 100 includes a radiation source 170 that emits a beam 172 that penetrates the volume 124 over a plurality of volume elements or voxels 122 that are defined within a frame of reference of the radiation source 170. The radiation source 170 transmits the beam 172 to each voxel 122 along the beam with an intensity and shape that is dependent on how many of each voxel 122 along the beam is occupied by the target material 192, the OAR 194 or normal tissue. Combining the effects of multiple beams (their intensities and shapes), the goal is to transmit high dose to the target material 192, and low dose to the normal tissue and the OAR 194. Although FIG. 1A depicts the imaging systems 121 and radiation source 170 in the system 100, the radiation source 170 and imaging systems 121 are not necessarily in one system or apparatus and do not need to work simultaneously. Additionally, images can be captured by the imaging systems 121 before irradiation with the radiation source 170.

During the operation of the system 100, the radiation source 170 moves to different angles around the subject 190, so that the beam 172 is directed at the target material 192 from multiple directions. At some angular positions of the radiation source 170, the beam 172 passes through the OARs 194 to get to the target material 192. As illustrated in FIG. 1A, if the radiation source 170 rotates to a left side of the target material 192, the beam 172 needs to pass through the OARs 194 to get to the target material 192. However, at other angular positions of the radiation source 170, the beam 172 need not pass through the OARs 194 to get to the target material 192. As illustrated in FIG. 1A, when the radiation source 170 rotates to a top side of the target material 192, the beam 172 need not pass through the OARs 194 to get to the target material 192.

Figure 17:
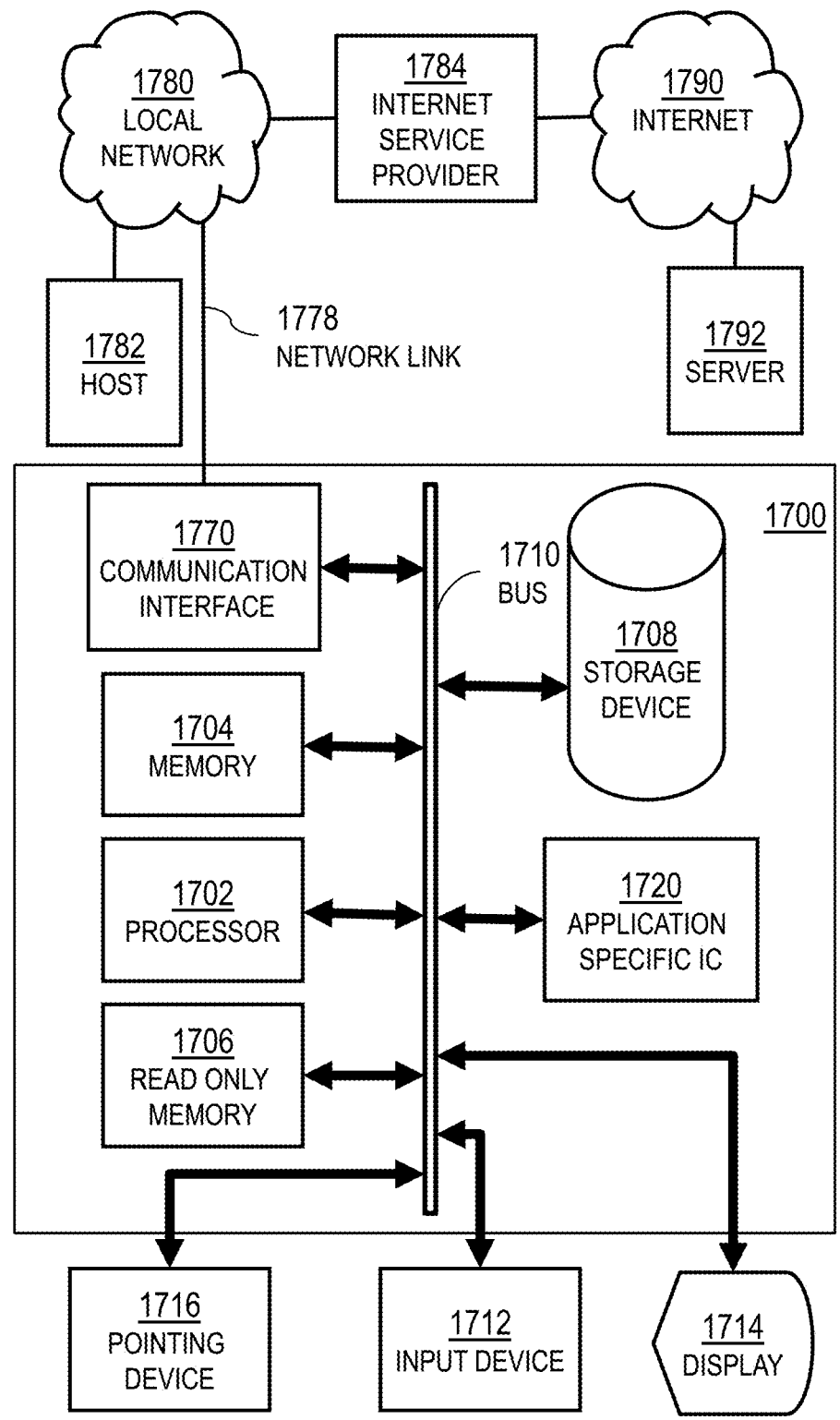
FIG. 17 is a block diagram that illustrates an example computer system upon which an embodiment of the invention may be implemented.
Figure 18:
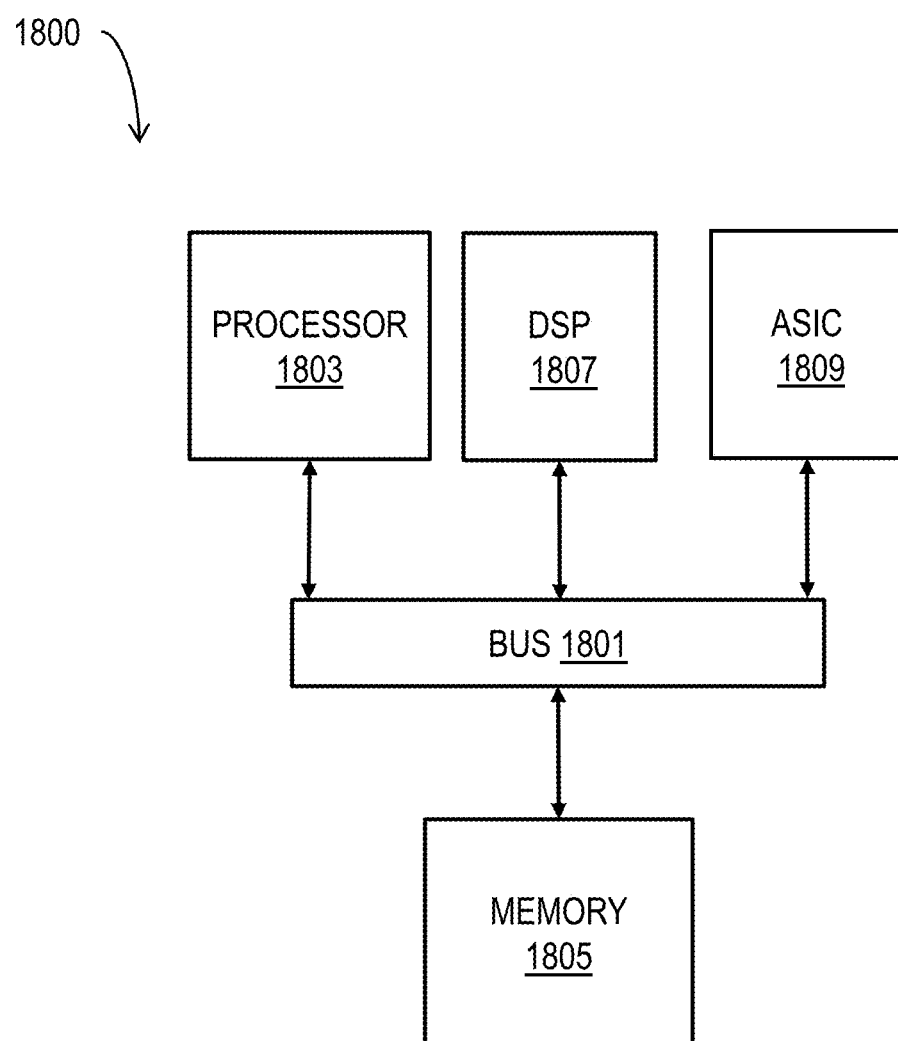
FIG. 18 is a block diagram that illustrates an example chip set upon which an embodiment of the invention may be implemented.

As illustrated in FIG. 1A, a computer system 150 is provided to control the one or more imaging systems 121, to collect imaging data from the one or more imaging systems 121 before or at the time of radiation, to determine the intensity and shape of the beam 172 delivered to each voxel 122 in the volume 124 and to transmit the intensity and shape of the beam 172 for multiple beams to the radiation source 170. The computer system 150 includes a function based radiation control process 140 to perform one or more steps of a method described below with reference to FIGS. 5A through 5C. In various embodiments, the computer system 150 comprises one or more general purpose computer systems or upgraded computer systems that include graphics processing units, as depicted in FIG. 17 or one or more chip sets as depicted in FIG. 18, and instructions to cause the computer or chip set to perform one or more steps of a method described below with reference to FIGS. 5A through 5C.

FIG. 1B is a block diagram that illustrates scan elements in a 2D scan 110, such as one scanned image slice of the volume 124 from the imaging system 121, such as a CT scanner. The two dimensions of the scan 110 are represented by the x direction arrow 102 and the y direction arrow 104. The scan 110 consists of a two dimensional array of 2D scan elements (pixels) 112 each with an associated position. Typically, a 2D scan element position is given by a row number in the x direction and a column number in the y direction of a rectangular array of scan elements. A value at each scan element position represents a measured or computed image intensity that represents a physical property (e.g., X-ray attenuation, or resonance frequency of an MRI scanner) at a corresponding position in at least a portion of the spatial arrangement of the living body. The measured property is called image intensity hereinafter and is treated as a scalar quantity. In some embodiments, two or more properties are measured together at a pixel location and multiple image intensities are obtained that can be collected into a vector quantity, such as spectral intensities in MRSI. Although a particular number and arrangement of equal sized circular scan elements 112 are shown for purposes of illustration, in other embodiments, more elements in the same or different arrangement with the same or different sizes and shapes (e.g. equal sized square scan elements) are included in a 2D scan.

Figure 1C:
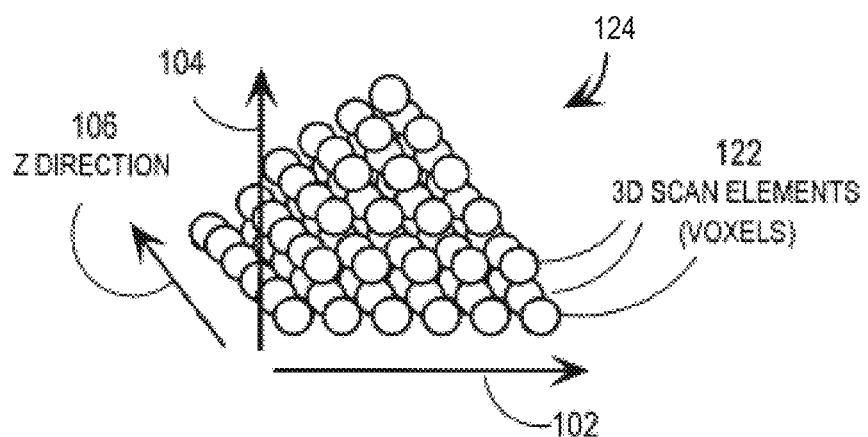
FIG. 1C is a block diagram that illustrates a plurality of example voxels within a fixed frame of reference of the radiation source of FIG. 1A.

FIG. 1C is a block diagram that illustrates the plurality of voxels 122 that are defined in the volume 124 within a fixed frame of reference of the radiation source 170 of FIG. 1A. The fixed frame of reference of the radiation source 170 is defined based on the x-direction 102, y-direction 104 and z-direction 106. Thus, in an example embodiment, a particular voxel 122 within the volume 124 in the frame of reference of the radiation source 170 is assigned a unique x-value, y-value and z-value. As previously discussed, some of the voxels 122 are occupied by target material 192, some of the voxels 122 are occupied by OAR material 194 and the remaining voxels 122 in the volume 124 are occupied by normal tissue. The computer system 150 determines the respective intensity and shape of the beam 172. Although a particular number and arrangement of equal voxel 122 are shown for purposes of illustration, in other embodiments, more voxels 122 in the same or different arrangement with the same or different sizes and shapes (e.g. equal sized cube elements) are included in the frame of reference of the radiation source 170. In an example embodiment, the voxel 122 has a length in a range of 3-5 millimeters, a width in a range of 3-5 millimeters and a depth in a range of 2-3 millimeters.

Figure 1D:
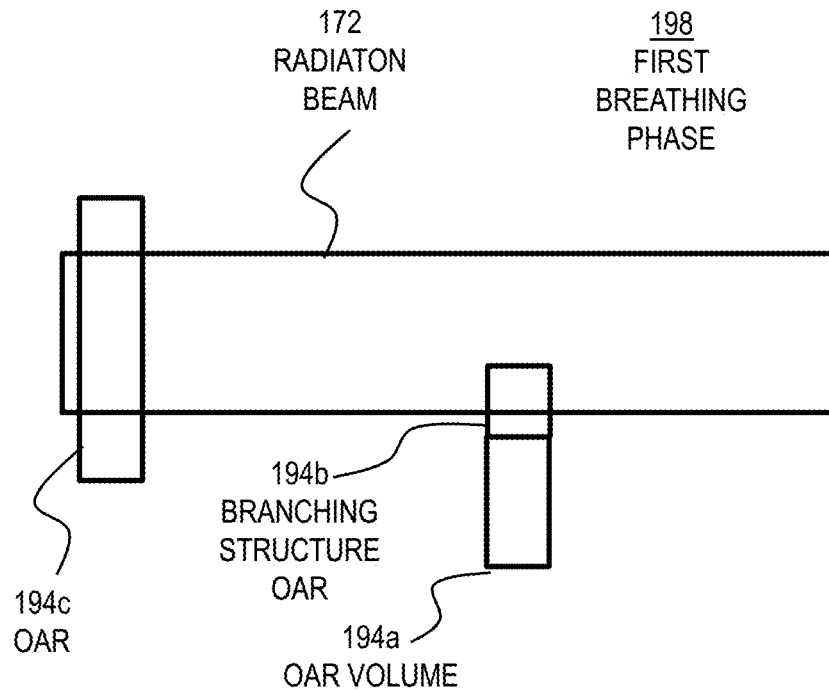
FIG. 1D is a block diagram that illustrates an example OAR exposed to the radiation beam of FIG. 1A during a first phase of a breathing cycle, according to an embodiment.

In some embodiments, the OAR 194 radiated by the radiation source 170 is a branching structure 194b whose functionality may affect the functionality of a dependent OAR 194a or sub-volumes of the OAR 194a. In an embodiment, the branching structure 194b has criteria (e.g. size) that affects whether or not it is radiated by the beam 172 at different phases of a breathing cycle. FIG. 1D is a block diagram that illustrates OARs 194 exposed to the radiation beam 172 of FIG. 1A during a first phase 198 of a breathing cycle, according to an embodiment. In an embodiment, the OAR 194b is a branching structure supporting a dependent OAR volume 194a. In one embodiment, the functionality of the branching structure 194b affects the functionality of the dependent OAR volume 194a. In an example embodiment, the branching structure 194b is an airway segment of a bronchial tree and the dependent OAR volume 194a is a volume of alveoli downstream of an airway segment (e.g. terminal airway segment) of the bronchial tree. In an embodiment, the branching structure 194b has dimensions that are sufficiently small that the branching structure 194b is capable of moving out of and into the beam 172 during different phases of the breathing cycle. In an example embodiment, branching structures (e.g. airway segments or bronchi) have dimensional ranges including an external diameter between about 3 mm and about 22 mm, with most frequent values from about 3 mm to about 5 mm (corresponding to peripheral bronchi, i.e., 3 or more branching generations); and a length between about 4 mm and about 100 mm, with most frequent values from about 6 mm to about 14 mm. In an example embodiment, the dependent OAR 194a is dependent on the branching structure 194b, even if the branching structure 194b is out of the beam 172.

Figure 1E:
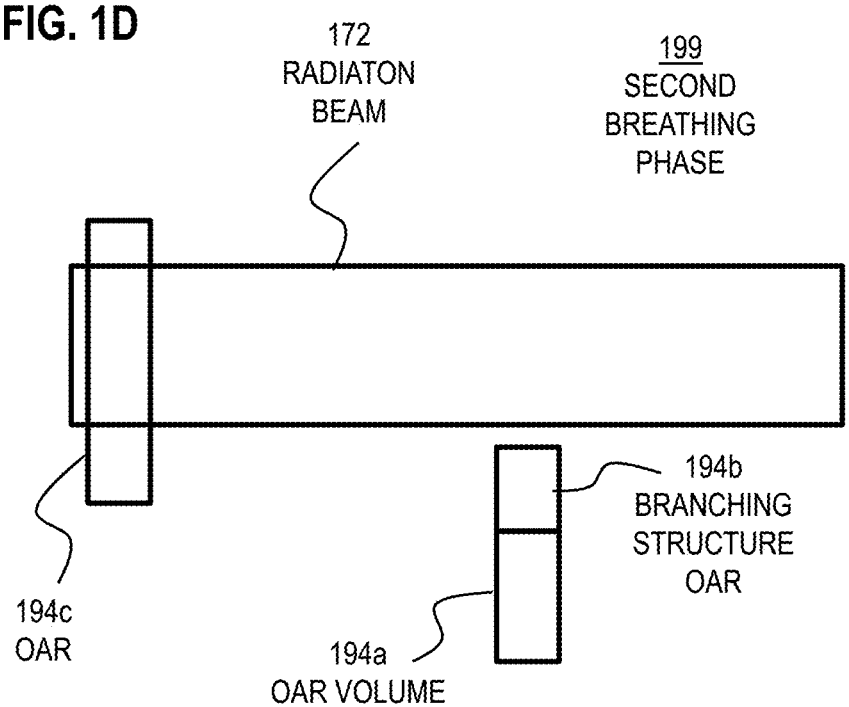
FIG. 1E is a block diagram that illustrates an example OAR not exposed to the radiation beam of FIG. 1A during a second phase of a breathing cycle, according to an embodiment.

FIG. 1E is a block diagram that illustrates the branching structure OAR 194b and dependent OAR volume 194a not exposed to the radiation beam 172 of FIG. 1A during a second phase 199 of a breathing cycle, according to an embodiment. In an embodiment, the branching structure 194b moved out of the beam 172 during the second phase 199 of the breathing cycle. In one embodiment, a second OAR 194c (e.g. heart or different portion of the lung) is positioned within the beam 172 during both phases 198, 199 of the breathing cycle. Since the branching structure 194b is positioned outside the beam 172 during one or more phases of the breathing cycle, the inventors recognized that it would be advantageous to consider the position of the branching structure 194b at each phase of the breathing cycle when optimizing a radiation plan for the subject by reducing or minimizing the exposure of the branching structure 194b to the radiation beam 172. In an example embodiment, such optimization of a radiation plan would consider the dose received by the branching structure 194b at each phase of the breathing cycle rather than conventional methods which blur the positions of the branching structures across a whole breathing cycle.

Figure 1F:
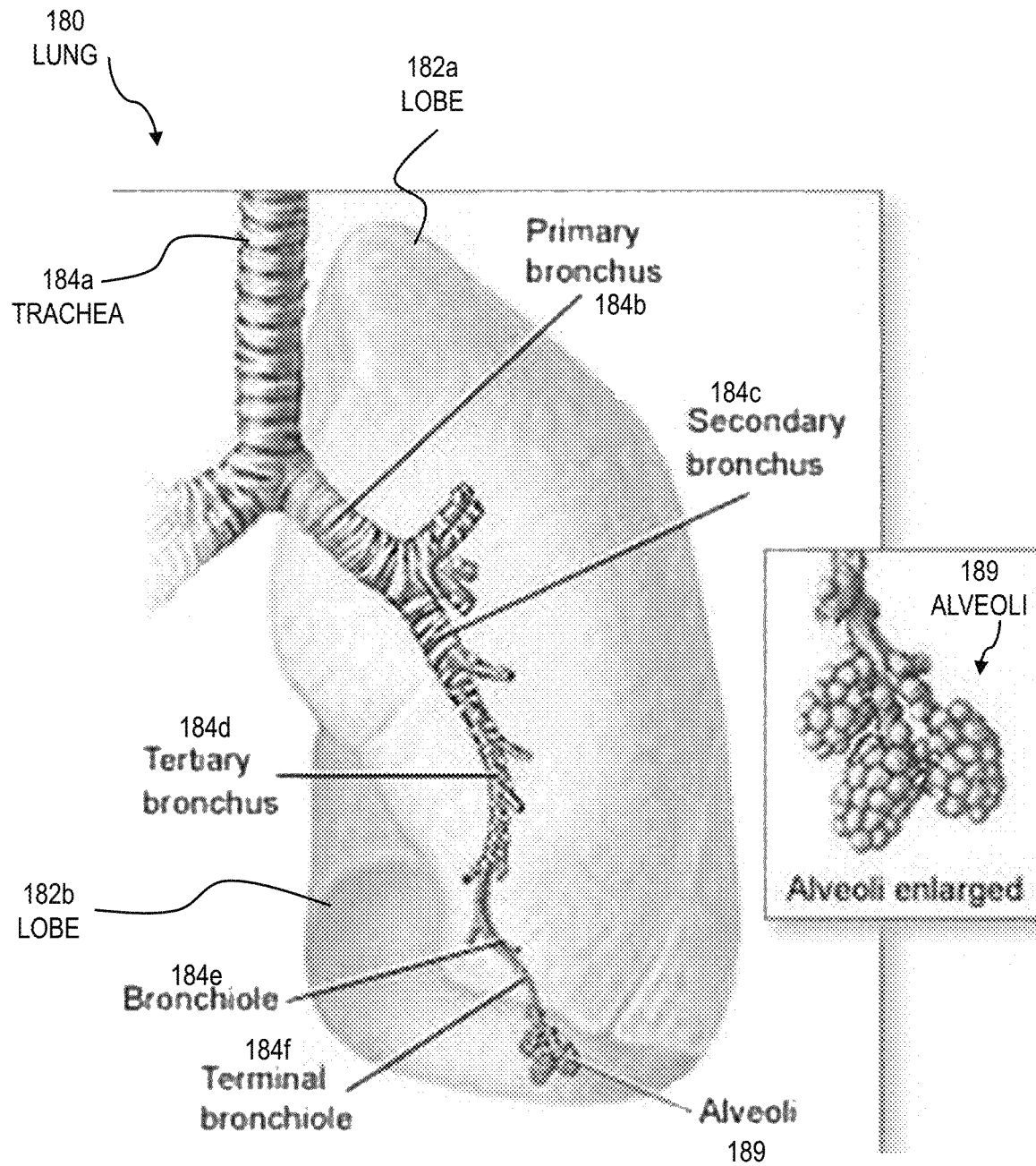
FIG. 1F is an image that illustrates an example of a cross-sectional view of a lung OAR of a subject.

In some embodiments, where the OAR 194 is a lung, the branching structures 194b include airway segments of a bronchial tree of the lung and the dependent OAR volumes 194a include alveoli volumes downstream of and in flow communication with the airway segments. FIG. 1F is an image that illustrates an example of a cross-sectional view of a lung 180 of a subject. In one embodiment, the lung 180 includes a plurality of lobes 182a, 182b. As appreciated by one of ordinary skill in the art, the left lung 180 has two lobes and the right lung (not shown) has three lobes. The bronchial tree defines a plurality of airway segments 184a through 184f including a first airway segment 184a (e.g. trachea), a second airway segment 184b (e.g. primary bronchus), a third airway segment 184c (e.g. secondary bronchus), a fourth airway segment 184d (e.g. tertiary bronchus), a fifth airway segment 184e (e.g. bronchiole) and a sixth or terminal airway segment 184f (e.g. terminal bronchiole). The lung 180 also includes a plurality of dependent volumes 189 (e.g. alveoli) that are connected and downstream of the terminal airway segment 184f. Although six levels (generations) of airway segments in the airway tree are depicted in FIG. 1F, in other embodiments there can be more or less than six levels of airway segments in an airway tree. As shown in FIG. 1F, the dependent volume 189 is downstream of each of the airway segments 184a through 184f. Thus, the functionality of the dependent volume 189 is based on continued functionality of each of these airway segments 184a through 184f (e.g. that none of these airway segments collapse during a radiation treatment plan) to ensure continued airflow to and from the dependent volume 189.

Figure 2A:
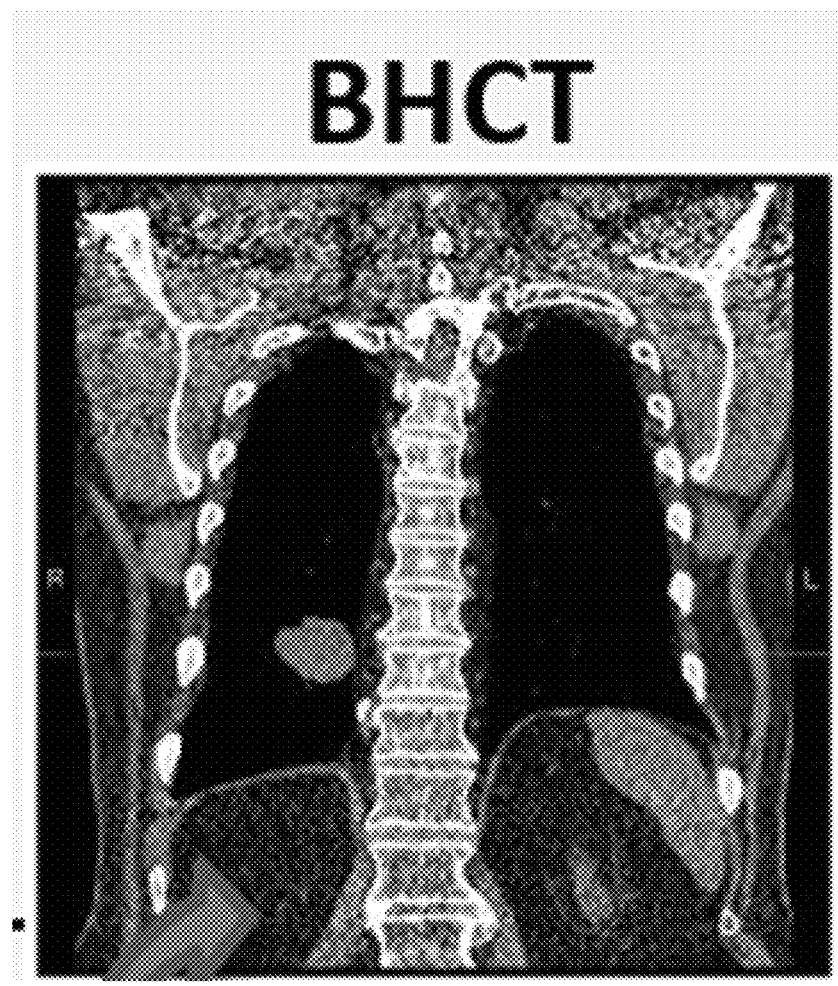
FIG. 2A is an image that illustrates an example of a scanned image to identify tissue type in a subject, such as a scanned image from a CT scanner, according to an embodiment.
Figure 2B:
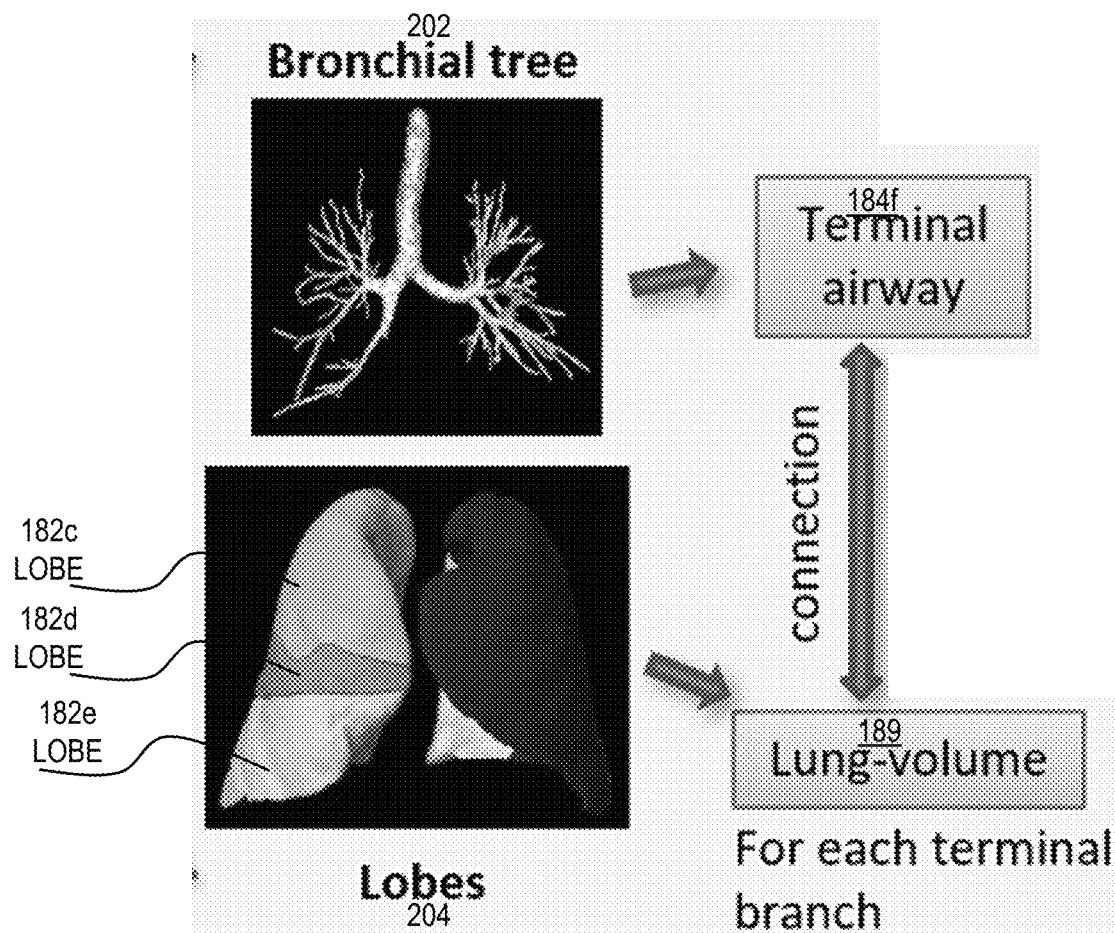
FIG. 2B are images that illustrate an example of a bronchial tree and lobes based on segmentation of the scanned image of FIG. 2A, according to an embodiment.

In some embodiments, where the OAR 194 is a branching structure OAR 194b and/or a dependent OAR volumes 194a, the OAR 194 is imaged by the imaging system 121 and subsequently segmented into the branching structures 194b and dependent OAR volumes 194a. FIG. 2A is a block diagram that illustrates a scanned image 200 to identify tissue type in the subject 190 from one of the imaging systems 121, such as a CT scanner. In one embodiment, the scanned image 200 is a breath-hold computed tomography (BHCT) image of the subject 190. FIG. 2B is an image that illustrates segmentation of the scanned image 200 into a set of branching structures 194b (e.g. a set of airway segments 184 of the bronchial tree 202) and dependent OAR volumes 194a (e.g. volumes 189) associated with the set of branching structures 194b. In one embodiment, the set of branching structures 194b is a bronchial tree 202 of the lung that defines a set of airway segments 184 and the dependent OAR volumes 194a are a plurality of dependent sub-lobar lung volumes 189 defined by the lobes 204. Although FIGS. 2A and 2B depict segmentation of a scanned image 200 of a lung OAR, in other embodiments the scanned image 200 is of an OAR other than the lung.

In an embodiment, the scanned image 200 is segmented into lobes 204 using software appreciated by one of ordinary skill in the art, such as 3D Slicer® [1], [2]. In one embodiment, the segmentation of the right lung lobes 204 includes segmentation of lobes 182c, 182d, 182e. In other embodiments, segmentation of the left lung lobes includes segmentation of lobes 182a, 182b. In an embodiment, the segmentation further divides the bronchial tree 202 into a set of airway segments 184 (e.g. airway segments 184a through 184f). The set of airway segments 184 is not limited to the scale of the individual airway segments 184a through 184f identified in FIG. 1F and may involve airway segments with greater resolution (e.g. smaller scale) than depicted in FIG. 1F. This segmentation of the bronchial tree 202 into the plurality of airway segments 184 can be provided by any software appreciated by one of ordinary skill in the art [3].

In some embodiments, after segmenting the imaged OAR 194 into the branching structures 194b and the dependent OAR volumes 194a, each branching structure 196b is uniquely identified and each dependent OAR volume 194a is uniquely associated with one or more of the identified branching structures 194b. In an embodiment, the segmentation of the bronchial tree 202 involves assigning a unique identifier to each airway segment 184 (e.g., to each terminal airway segment 184f in FIG. 1F). In another embodiment, the segmentation further segments the lobes 204 into one or more dependent sub-lobar volumes 189 (e.g. volume 189 at the end of the terminal airway segment 184f in FIG. 1F). In an example embodiment, the segmentation of the bronchial tree 202 further involves associating or connecting each dependent sub-lobar volume 189 with one or more airway segments 184. In one example embodiment, each dependent sub-lobar volume 189 is associated with the terminal airway segment 184 (e.g. terminal airway segment 184θ for that dependent sub-lobar volume 189. In another example embodiment, each sub-lobar volume 189 is associated with each upstream airway segment 184 that facilitates airflow to and from that dependent sub-lobar volume 189 (e.g. 184a through 184f for the volume 189 in FIG. 1F). For example, the dependent sub-lobar volumes associated with two (sometimes narrower) branch structures from an upstream (sometimes wider) branching structure are both associated with the upstream branching structure.

Figures 3A, 3B:
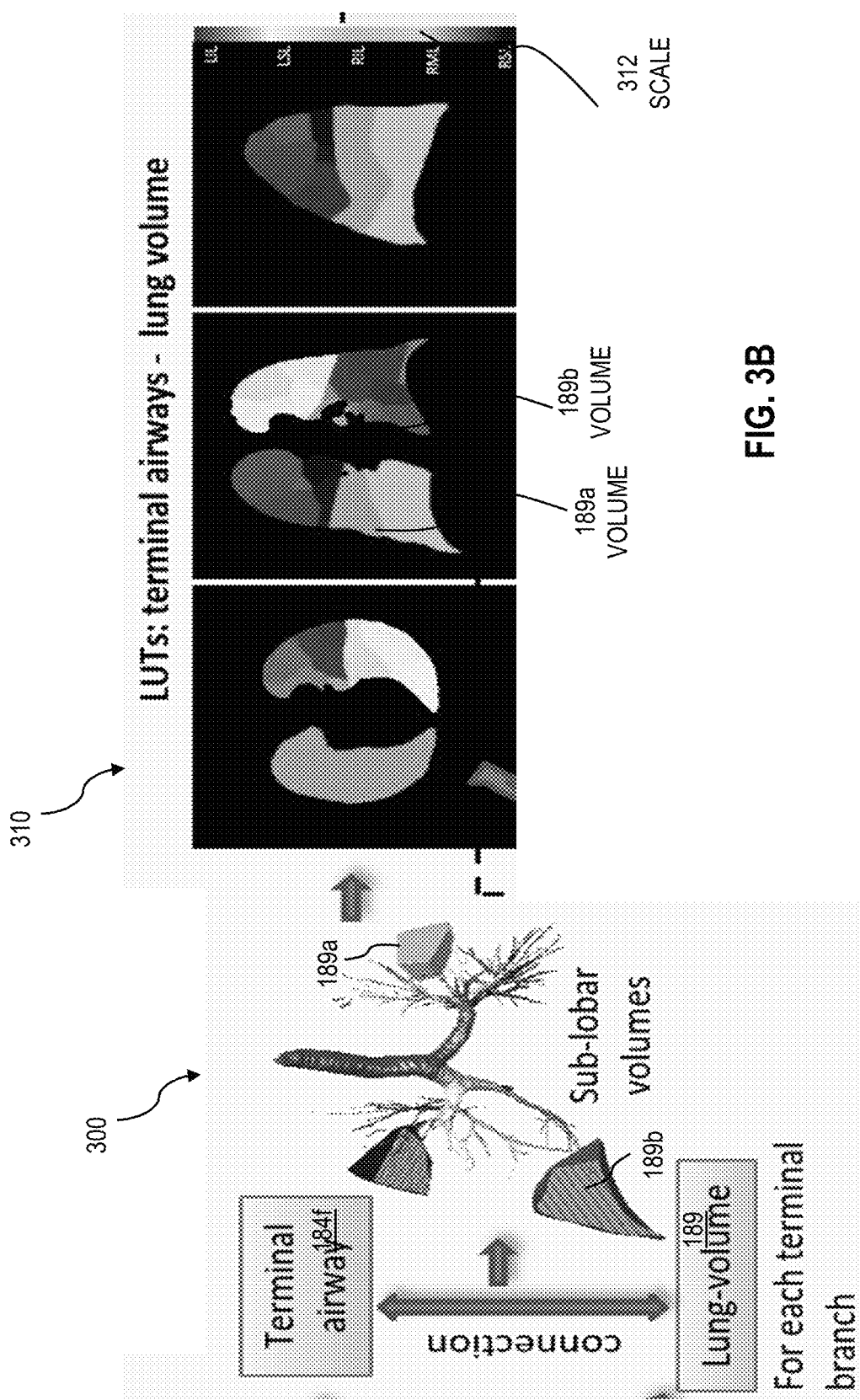
FIG. 3A is an image that illustrates an example of lung volumes connected with terminal airways of the bronchial tree of FIG. 2B, according to an embodiment.
FIG. 3B is an image that illustrates an example of a look-up table (LUT) that identifies the terminal airway associated with each lung volume, according to an embodiment.

FIG. 3A is an image 300 that illustrates an example of dependent sub-lobar volumes 189 connected with terminal airway segments 184 (e.g. terminal airway segment 184f) of the bronchial tree 202 of FIGS. 1F and 2B, according to an embodiment. In one embodiment, the image 300 depicts each dependent sub-lobar volume 189 connected with the respective terminal airway segment 184 (e.g. terminal airway segment 184f) for that dependent lung volume 189. In another embodiment, the image 300 depicts each dependent sub-lobar lung volume 189 connected with each airway segment 184 upstream of the sub-lobar lung volume 189 (e.g. airway segment 184a through 184f for the volume 189 in FIG. 1F).

For purposes of identifying the branching structures 194b associated with each dependent OAR volume 194a, a look-up table (LUT) is provided which identifies the branching structures 194b associated with each dependent OAR volume 194a. FIG. 3B is an image that illustrates an example of a LUT 310 that identifies the branching structure (e.g. terminal airway segment) associated with each dependent OAR volume (e.g. lung volume), according to an embodiment. In an embodiment, each LUT 310 is divided into regions based on the dependent sub-lobar lung volumes 189 and a pixel value of the LUT 310 in each dependent sub-lobar lung volume 189 region identifies the terminal airway segment 184 for that lung volume 189. In one example embodiment, the segmentation of the bronchial tree 202 into a plurality of airway segments 184 involves associating each airway segment 184 with a unique identifier (e.g. number). In this example embodiment, the value of each pixel in the LUT 310 at each dependent sub-lobar lung volume 189 region is based on the unique identifier for the terminal airway segment 184 associated with the dependent sub-lobar lung volume 189. In an example embodiment, where each airway segment 184 has a unique number identifier, the value of the pixel for each dependent sub-lobar lung volume 189 region of the LUT 310 is based on the number identifier for the terminal airway segment 184 of that dependent sub-lobar lung volume 189. In some embodiments, the value of the pixel for each sub-lobar lung volume 189 region is based on a number scale 312 provided with the LUT 310. In an example embodiment, the number of dependent sub-lobar lung volume 189 regions in the LUT 310 correspond with the number of dependent lung sub-lobar volumes 189 capable of being resolved during the segmentation of the scanned image 200.

In some embodiments, the value associated with a branching structure 194b is further adapted to consider a value of a parameter that quantifies a level of dependence of the dependent OAR volumes 194a on that branching structure 194b. In an example embodiment, the value associated with an airway segment is adapted to consider the ventilation capacity of the dependent lung volumes associated with that airway segment. Thus, in this embodiment, airway segments that service dependent lung volumes that undergo greater ventilation are given more weight than airway segments that service less well ventilating lung volumes. FIG. 3C is an image that illustrates an example of tissue measurements of the subject 190 conducted at multiple phases of a breathing cycle. In one embodiment, the tissue measurements are a four-dimensional computed tomography (4DCT) 330 of the subject 190 including a CT image at an exhalation phase, according to an embodiment. FIG. 3D is an image that illustrates an example of CT images of the 4DCT of FIG. 3C at the different phases of the breathing cycle from one of the imaging systems 121, such as a 4DCT-based ventilation/perfusion imaging system or a SPECT-based ventilation/perfusion system or an MRI-based ventilation/perfusion system. In one embodiment, the 4DCT 330 includes a plurality of CT images that are captured at multiple (e.g. 4 to 16, such as 10) phases of a breathing cycle of the subject 190. In an embodiment, the 4DCT 330 includes a peak-exhale phase CT image 332 that is captured at a peak-exhale phase of the breathing cycle and a peak-inhale phase CT image 334 that is captured at a peak-inhale phase of the breathing cycle.

Figure 7A:
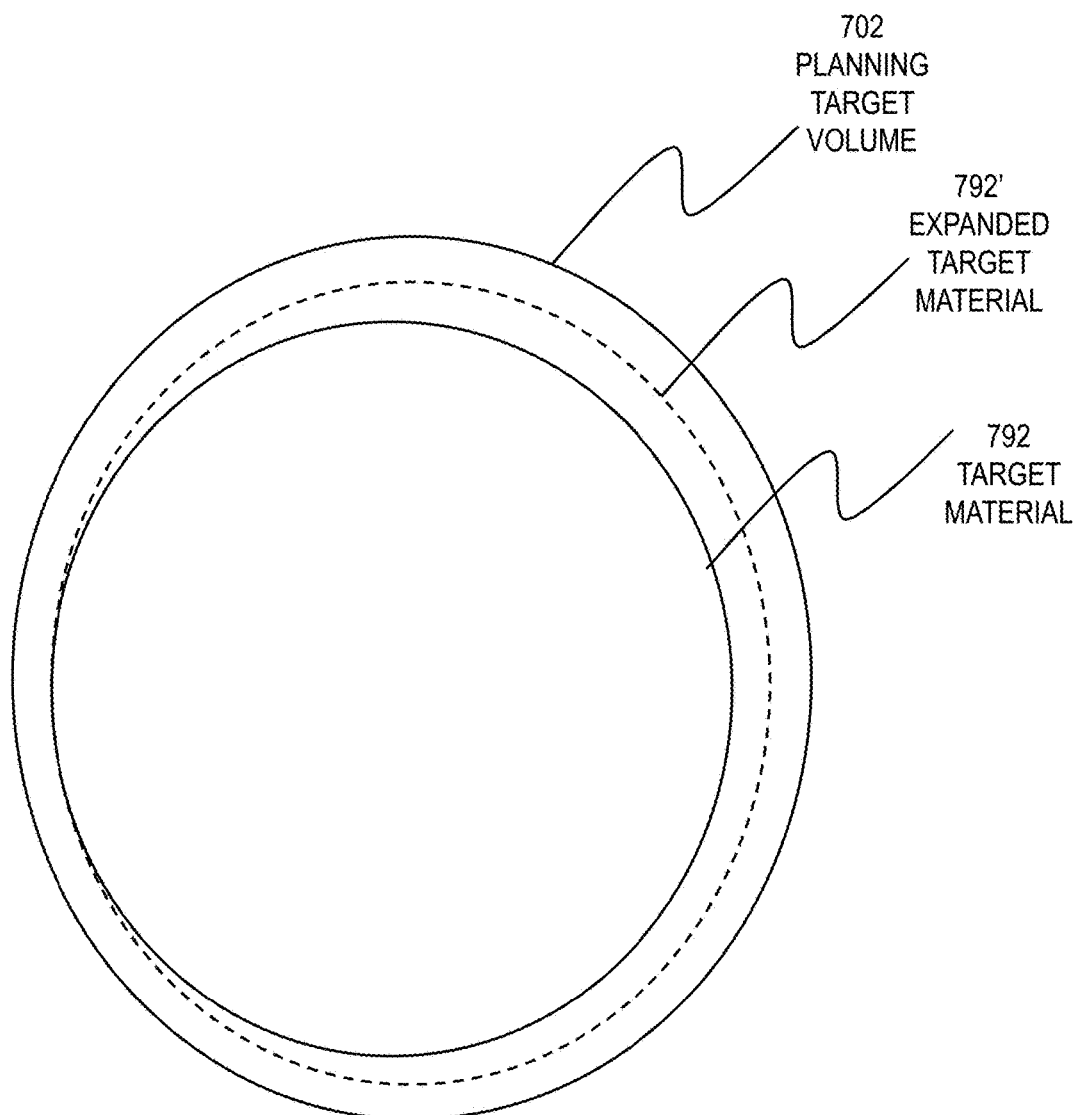
FIG. 7A is a block diagram that illustrates an example of a planning target volume that encloses the target material, according to an embodiment.
Figure 7B:
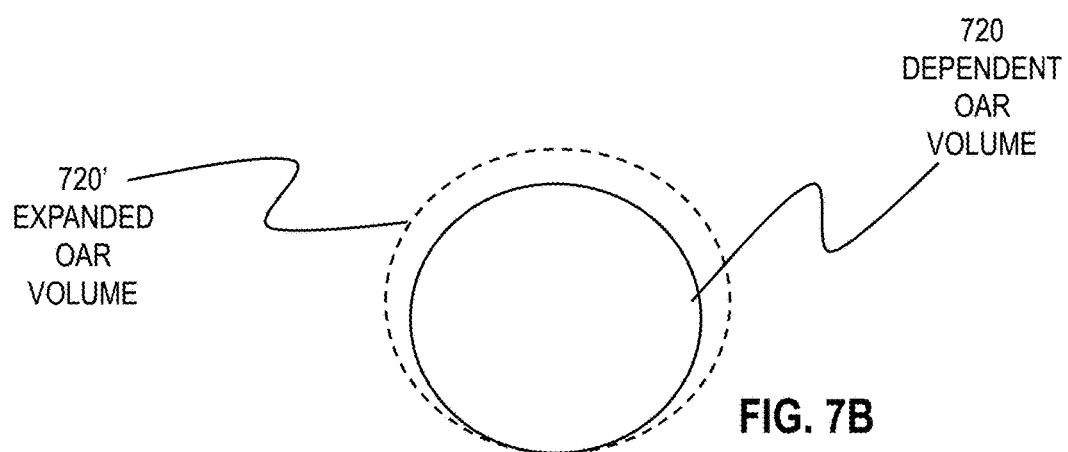
FIG. 7B is a block diagram that illustrates an example of an OAR volume over multiple phases of a breathing cycle, according to an embodiment.

FIG. 3E is an image that illustrates an example of a ventilation map 340 based on the CT images of FIG. 3D at the peak-inhale and peak-exhale phases, according to an embodiment. In one embodiment, a value of each voxel 344 of the ventilation map 340 is determined based on the corresponding voxel value of the peak-exhale phase CT image 332 and the peak-inhale phase CT image 334. In an example embodiment, the value of the ventilation map 340 is higher for those dependent lung volumes 206 that experience large variations over the breathing cycle (e.g. large variation in the volume 189 of FIG. 1F over a breathing cycle). As depicted in FIG. 3E, the value of each voxel 344 is based on a scale 342. In one example embodiment, the value of each voxel 344 in the ventilation map 340 is a CT ventilation imaging (CTVI) hybrid metric that is calculated as follows:

$$CTVI_{hybrid}=HU_{ex}(x)/jac(x,v)-HU_{in}(x) \quad (1)$$

where $HU_{ex}$ is the intensity of the $x^{th}$ voxel in Hounsfield units (HU) in the exhale phase CT image 332; $HU_{in}$ is the intensity of the $x^{th}$ voxel in HU units in the inhale phase CT image 334, x is the index of the voxel, v is a vector that indicates a displacement of the $x^{th}$ voxel from $HU_{in}(x)$ to $HU_{ex}(x)$, and Jac is a Jacobian of the transformation of voxel x displaced by vector v. FIG. 7B depicts an embodiment where the dependent OAR volume 720 expands from a first phase (e.g. peak-exhale phase) to an expanded dependent OAR volume 720' at a second phase (e.g. peak-inhale phase). In one embodiment, the greater the variation in the dependent OAR volume 720, 720' between the two phases, the higher the value of the CTVI metric from equation 1.

In some embodiments, since the voxel intensity values calculated in equation 1 are to be used in conjunction with the data used to generate the LUT 310, the voxel intensity values are translated into the same reference frame (e.g. BHCT image) as the LUT 310 data. In one embodiment, where the LUT 310 is registered to the BHCT image, the data calculated in equation 1 is registered to the BHCT image. In an example embodiment, a deformable image registration (DIR) is performed from the peak-exhale phase image 332 to the BHCT and the resulting deformation vector fields (DVF) are applied to transform the ventilation map 340 to the BHCT image.

Figure 3F:
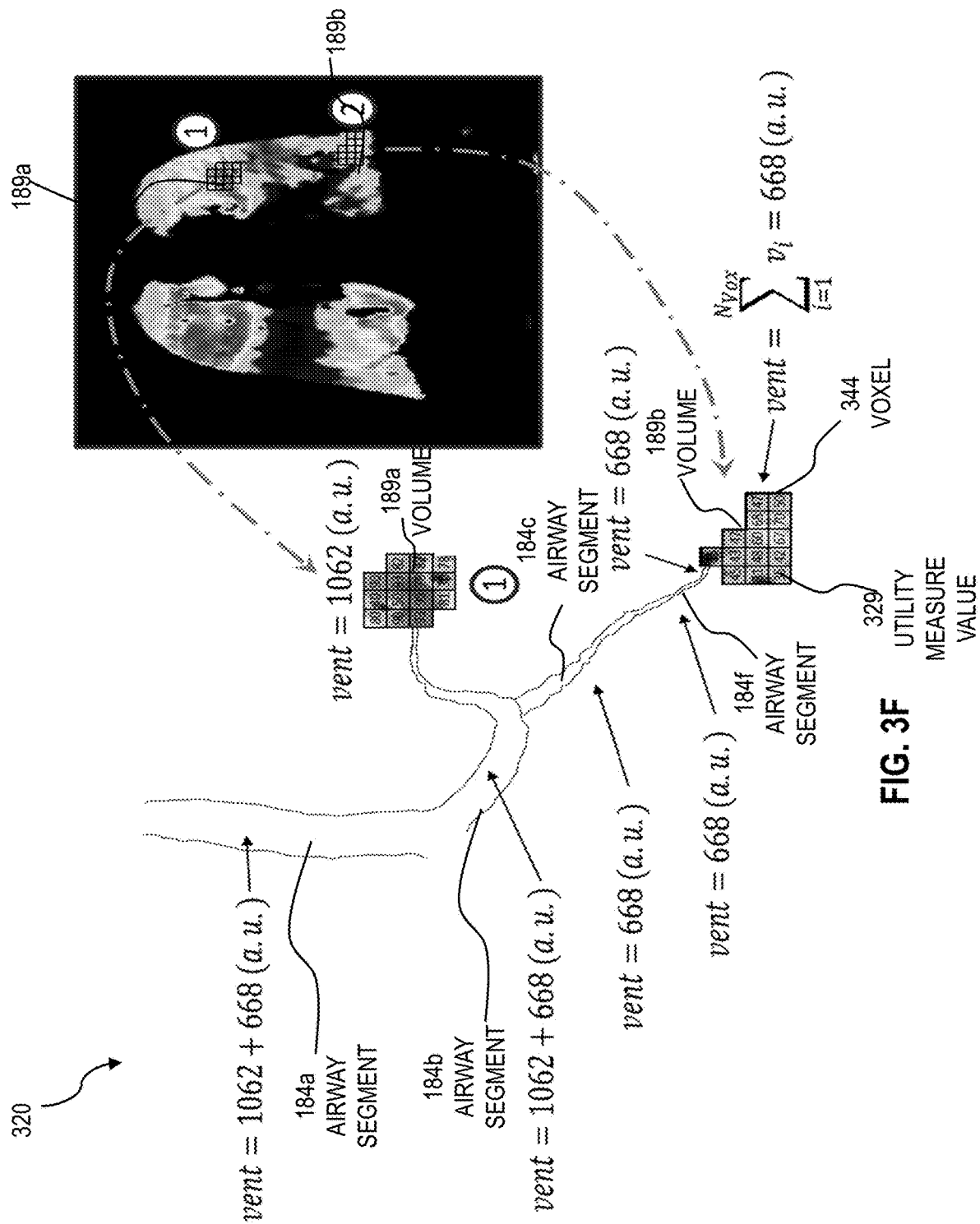
FIG. 3F is an image that illustrates an example of a plurality of lung volumes connected with a respective plurality of airway segments of the bronchial tree of FIG. 2B to determine a cumulative ventilation of each airway segment, according to an embodiment.

In some embodiments, after determining the ventilation of each voxel of the dependent sub-lobar lung volume 189 (e.g. using equation 1), a total ventilation of each sub-lobar lung volume 189 is determined. After determining the total ventilation of each lung volume 189, a cumulative ventilation of each airway segment 184 is determined based on summing the total ventilation of each sub-lobar lung volume 189 downstream of the airway segment 184. FIG. 3F is an image 320 that illustrates an example of a plurality of lung volumes 189a, 189b connected with a respective plurality of airway segments 184 of the bronchial tree of FIG. 2B to determine a cumulative ventilation of each airway segment 184, according to an embodiment. In an embodiment, each dependent sub-lobar lung volume 189 is connected with one or more airway segments 184 using the LUT 310, where the pixel value of each dependent sub-lobar lung volume 189 in the LUT 310 indicates the unique identifier of the airway segment 184 connected with the dependent lung volume 206. In one embodiment, the LUT includes the number ID of the terminal airway segment 184f. Upstream airway segments 184 to the terminal airway segment 184f are identified by using the airways' label names. These labels allow the identification of the parent (upstream airway segments) and the children (downstream airway segments) of each airway segment. In an embodiment, each dependent lung volume 189a, 189b includes a plurality of voxels 344 where each voxel 344 has a value 329 based on a utility measure for that respective voxel 344.

In one embodiment, the utility measure value 329 of each voxel 344 is based on equation 1. In an embodiment, a total ventilation of each sub-lobar lung volume 189 is computed as:

$$\text{vent} = \sum_{i=1}^{N_{vox}} v_i \quad (2)$$

where vent is the total ventilation of each dependent lung volume 189; i is the index of the voxels 344 in each dependent lung volume 189, $N_{vox}$ is the number of voxels 344 in each dependent sub-lobar lung volume 189 and Ai, is the value 329 of the utility measure (e.g. value of equation 1) for each voxel 344. Using equation 2, the total ventilation of the dependent volume 189a in FIG. 3F is calculated as 1062 arbitrary units (a.u.), the total ventilation of the volume 189b in FIG. 3F is calculated as 668 a.u. Each airway segment 184 is then assigned a value based on summing the total ventilation of all dependent lung volumes 189 downstream of the respective airway segment 184. In an embodiment, for the airway segments 184a and 184b, both dependent volumes 189a, 189b are downstream of the airway segments 184a, 184b and thus the cumulative ventilation volume of each airway segment 184a, 184b is a sum of the ventilation of the dependent volumes 189a, 189b (e.g. 1068 a.u.+668 a.u.). In an embodiment, for the airway segments 184c and 184f, only the dependent volume 189b is downstream of the airway segments 184c, 184f and thus the cumulative ventilation of each airway segment 184c, 184f is the ventilation of the dependent volume 189b (e.g. 668 a.u.).

Figure 3G:
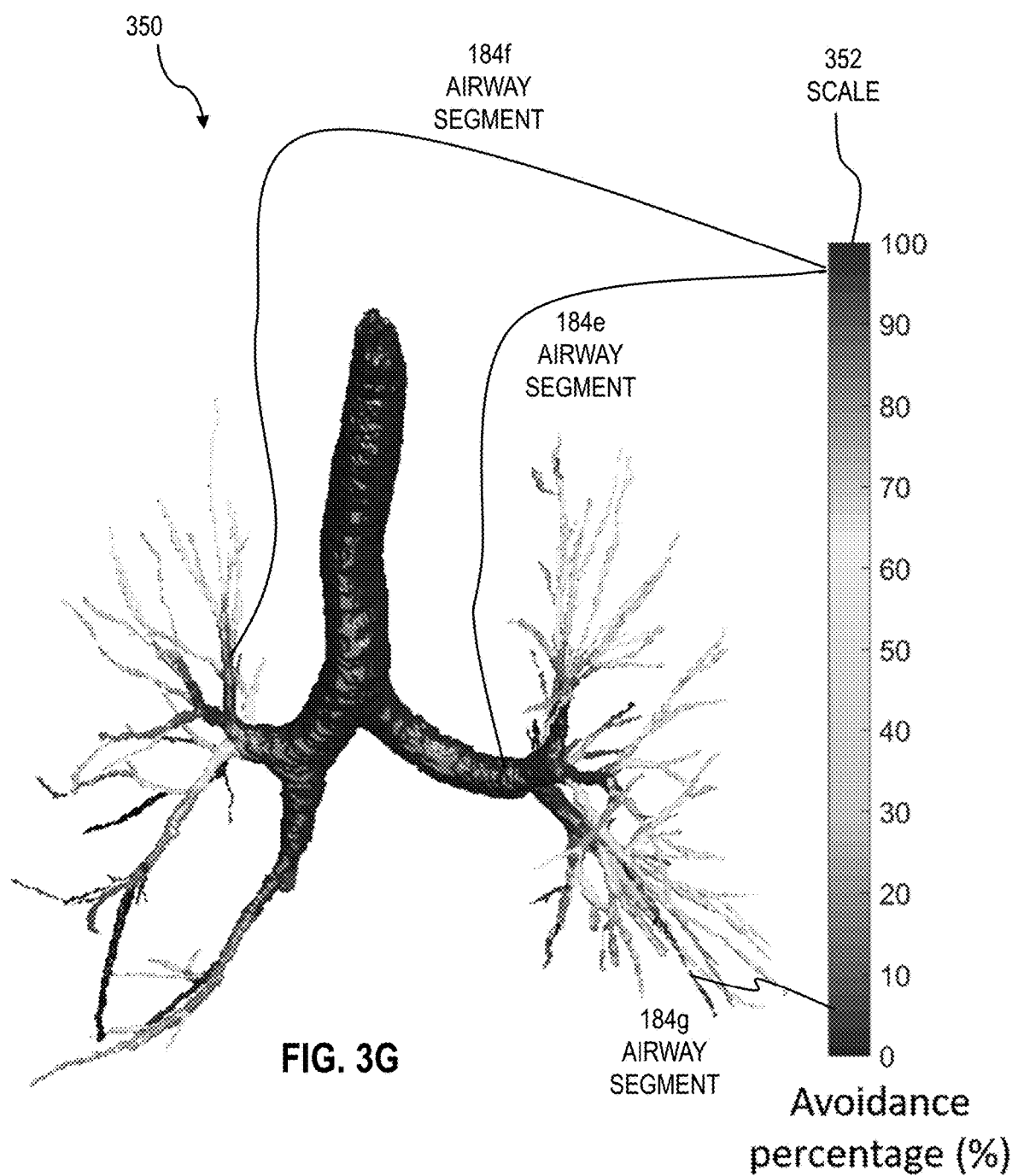
FIG. 3G is an image that illustrates an example of a functionally weighted airway sparing (FWAS) map based on the cumulative ventilation for each airway segment computed in FIG. 3F, according to an embodiment.

After determining the cumulative ventilation volume of each branching structure 194b (e.g. airway segment 184), a value of the cumulative ventilation volume of each branching structure is visually presented in a map (e.g. that is used to scale radiation avoidance in generating a radiation treatment plan). FIG. 3G is an image that illustrates an example of a functionally weighted airway sparing (FWAS) map 350 based on the cumulative ventilation for each airway segment 184 computed in FIG. 3F, according to an embodiment. In an embodiment, a grey scale 352 is provided that indicates a relative value of the cumulative ventilation for the airway segments 184. In an embodiment, the FWAS map 350 indicates that certain airway segments (e.g. airway segments 184e, 184f) have a high cumulative ventilation value whereas other airway segments (e.g. airway segment 184g) has a low cumulative ventilation value.

Figure 4:
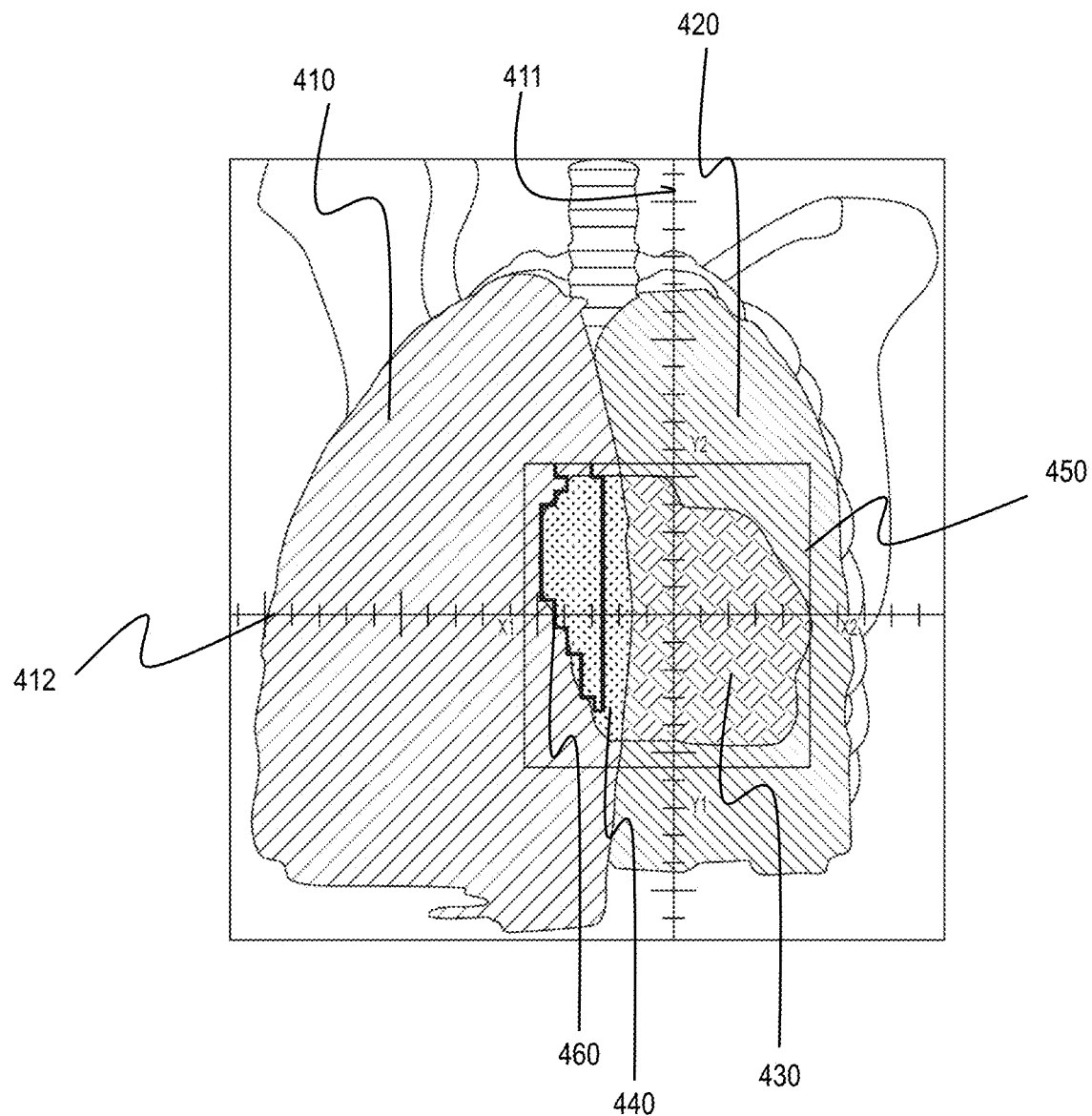
FIG. 4 is a block diagram that illustrates an example OAR and example target material in an example frame of reference of the example radiation source of FIG. 1A, according to an embodiment.

In some embodiments, a shape and intensity of the beam of the radiation device is varied depending on the arrangement of the tissue types within the subject 190 and the orientation of the beam relative to the tissue types. FIG. 4 is a block diagram that illustrates a shape of a beam, an OAR such as lungs 410, 420 and target material 430, 440 in a frame of reference of the radiation source 170 of FIG. 1A, according to an embodiment. The frame of reference of the radiation source 170 includes an x-dimension 412 and a y-dimension 411. The radiation source 170 can radiate a range 450 within the frame of reference, defined between $x_1$ and $x_2$ in the x-dimension 412 and $y_1$ and $y_2$ in the y-dimension 411. A plurality of rectangles (not shown) or multi-leaf collimators are positioned in a head of the radiation source 170 and are selectively positioned to shape the beam 172 in one of a plurality of directions at a selective portion of the range 450 for one of multiple time intervals. As depicted in FIG. 4, the beam 172 is shaped at a portion 460 of the target material 440 in one of a plurality of directions for one of multiple time intervals. After the radiation source 170 is arranged so that the beam 172 is shaped in one direction as depicted in FIG. 4, the radiation source 170 may transmit the beam 172 at selective intensities for selective time intervals, before the radiation source 170 is reconfigured to shape the beam 172 in another direction to the target material 430, 440.

As further illustrated in FIG. 4, a first portion of the target material 430 is on a near side of the radiation source 170 and thus the beam 172 passes into the first portion of the target material 430 without passing into the lung 410, and before passing into the lung 420 of the subject. However, a second portion of the target material 440 is positioned on a far side of the left lung 410 and thus the beam 172 needs to pass through the left lung 410 in order to reach the second portion of the target material 440. Thus, when developing the treatment plan for radiotherapy, in order to ensure that the target material 430, 440 receives a sufficient amount of high radiation dose to kill all tumor cells in the target material 430, 440, the lung 410 will necessarily receive some dose of radiation. It would be advantageous to ensure that the portions of the lung 410 which receive this dose of radiation are not high utility areas (e.g. branching structures 194b in the FWAS map of FIG. 3G with a high cumulative ventilation value and/or dependent OAR volumes 194a with a high total ventilation based on equation 2). Avoiding these high utility areas would be advantageous, in order to preserve these high utility areas of the OAR. When the beam 172 is oriented at the target material 430, 440 at a different direction than the direction depicted in FIG. 4, the beam 172 may pass into the second portion of the target material 440 without needing to pass through the lung 410.

Figure 5A:
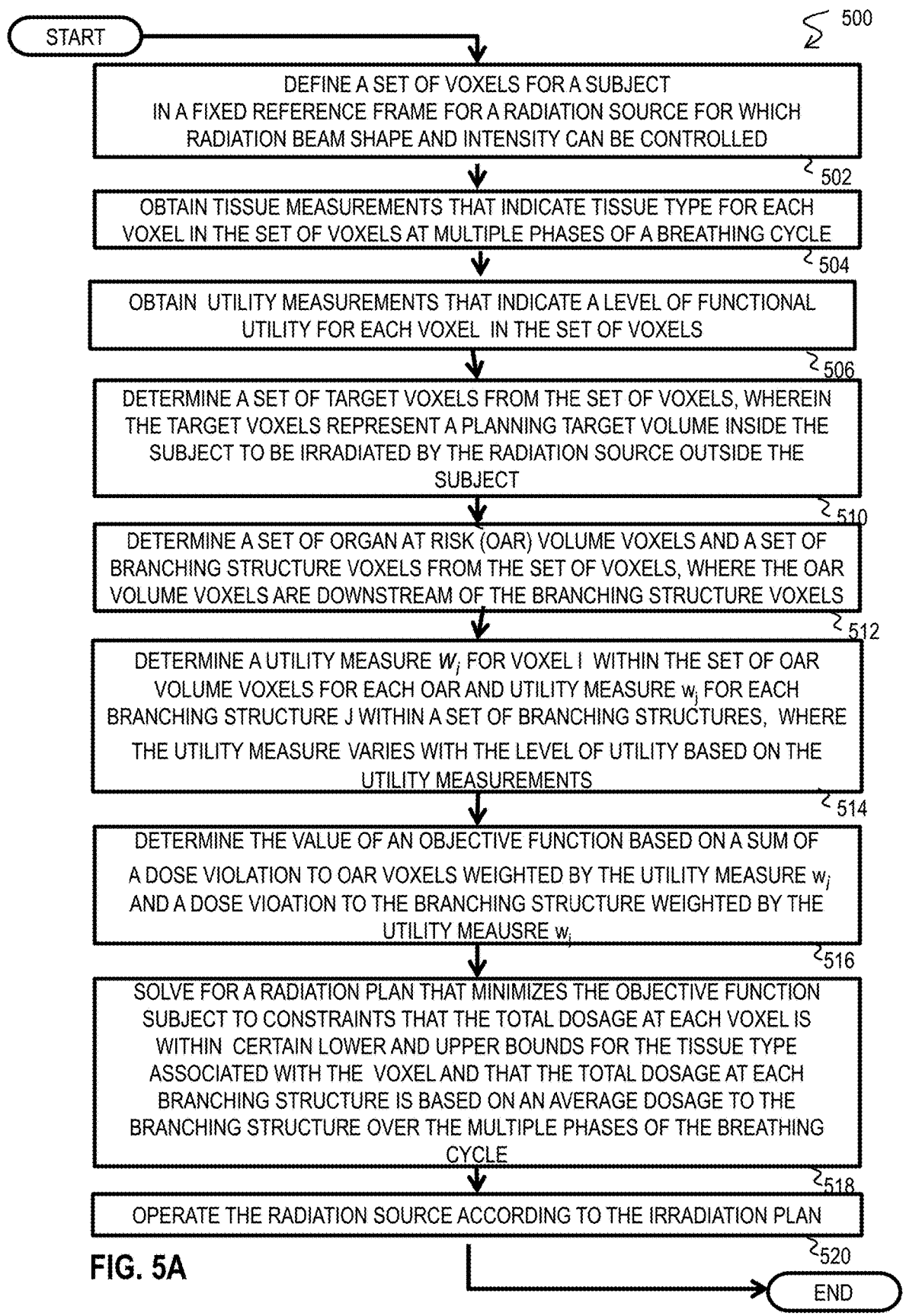
FIGS. 5A through 5C are flow diagrams that illustrate an example of a method for radiation therapy using functional measurements of branching structures, according to an embodiment.
Figure 5B:
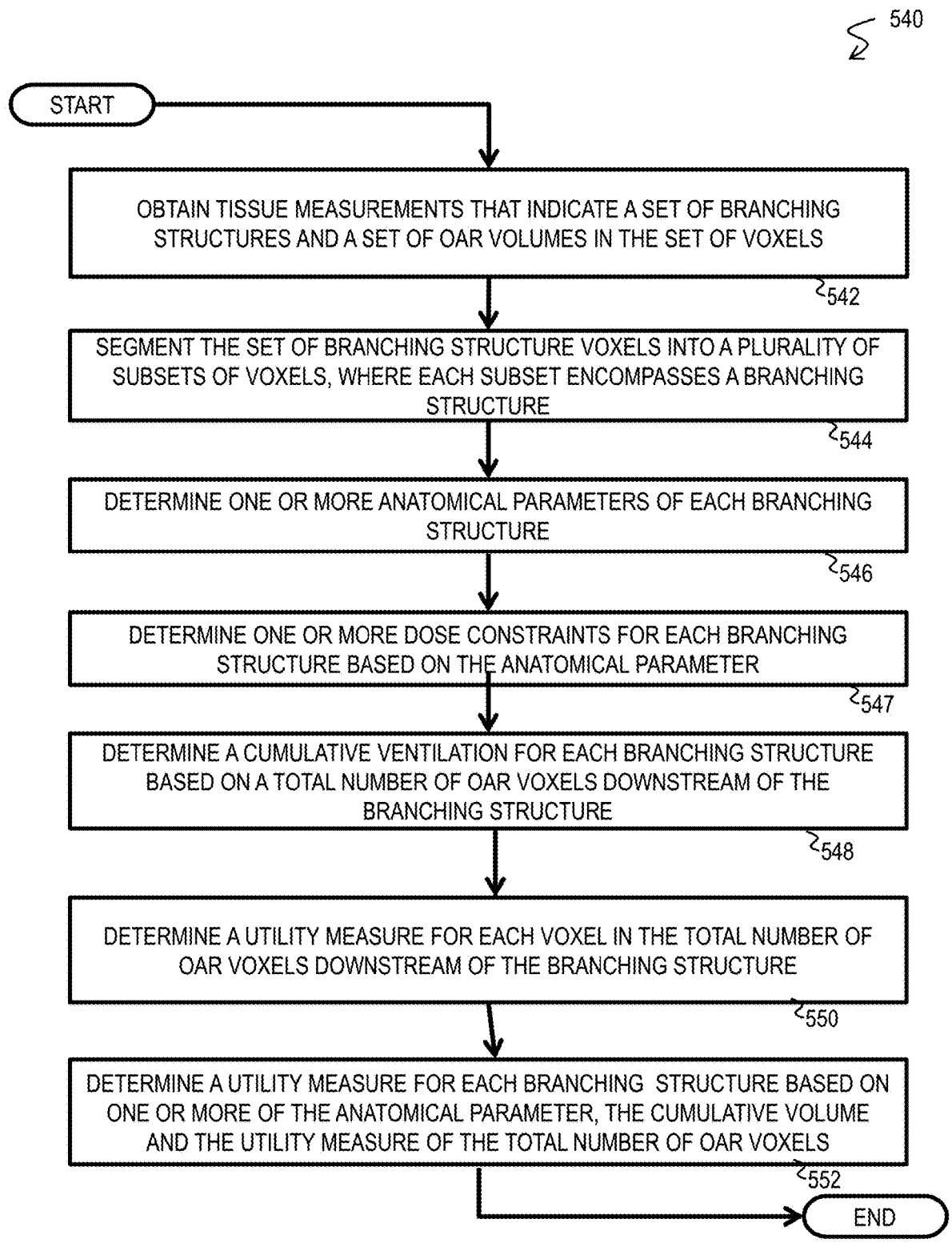
Figure 5C:
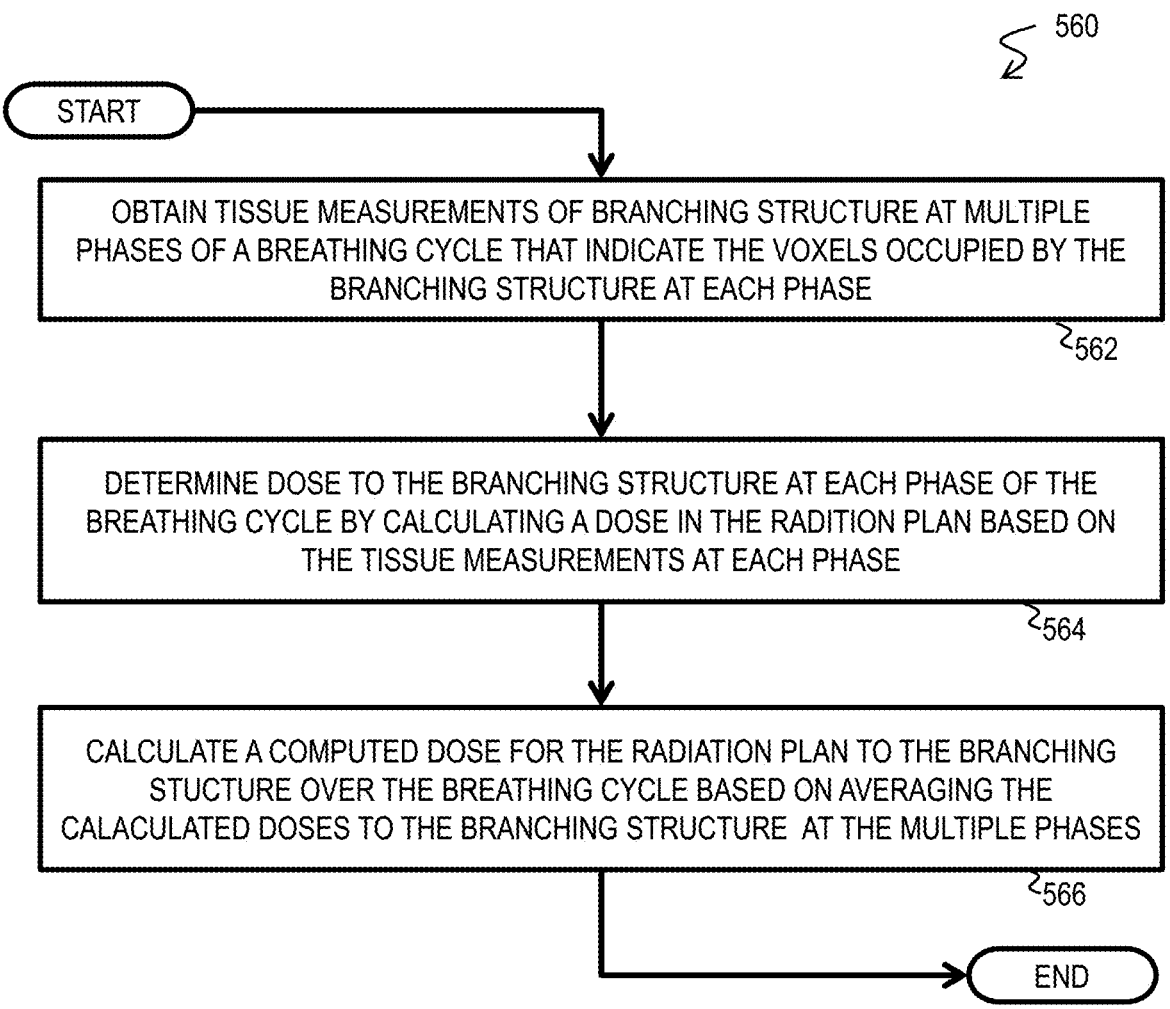

A method for determining a radiation therapy plan is discussed which preserves high utility areas of the OARs. FIGS. 5A through 5C are flow diagrams that illustrates an example of methods 500, 540, 560 for radiation therapy using functional measurements of branching structures of an OAR, according to an embodiment. For example, one or more of the steps of the method 500 and/or method 540 and/or method 560 are applied by process 140 of computer system 150. Although the flow diagrams of FIGS. 5A through 5C are depicted as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

In an initial step of the method, the voxels 122 are defined within the fixed reference frame of the radiation source 170. After starting, in step 502, the plurality of voxels 122 are defined for the subject 190 in the fixed reference frame for the radiation source 170 for which the radiation beam 172 shape and intensity can be controlled. As depicted in FIG. 1C, the voxels 122 are defined by the three-dimensional axes 102, 104, 106 in the fixed reference frame of the radiation source 170. Additionally, the voxels 122 are positioned within the imaging systems volume 124 that encompasses a portion of the subject 190, such that each voxel 122 is a respective volume element within the volume 124. Additionally, as previously discussed, the intensity and shape of the beam 172 can be controlled by the computer system 150.

In step 504, tissue type measurements are obtained that indicate tissue type for each voxel 122 in the volume 124. In an example embodiment, the imaging system 121 is a first imaging device that obtains the tissue measurements that relate to tissue type inside the volume 124. For example, the first imaging device is a CT scanner, an MRI scanner or a 4DCT-based ventilation imaging system. The obtained tissue measurements in step 504 are similar to the scanned image 200 of FIG. 2A which indicates the target 430, 440 tissue type as well as different OAR tissue types, including lung 210, 212 tissue type and spinal cord tissue type. In yet another embodiment, the obtained tissue type measurements in step 504 indicate tissue types within the OAR, such as the branching structure 194b tissue type (e.g. tissue type of the bronchial tree 202 and airway segments 184) and/or OAR volume 194a tissue type (e.g. tissue type of the alveoli volume 189). In an example embodiment, the imaging system 121 obtains cross-sectional tissue type measurements that are axially stacked and processed (including registration, interpolation and averaging in various embodiments) to generate imaging of each voxel 122 within the volume 124. In an example embodiment, step 504 is based on step 562 of the method 560, where the tissue type measurements are performed at multiple phases of a breathing cycle (e.g. about 4 to 16 phases or about 10 phases), to obtain tissue measurements (e.g. 4DCT 330) at each phase of the breathing cycle.

In one embodiment step 504 is based on step 542 of the method 540, where the tissue measurements are obtained that indicate the tissue type of the set of branching structures 194b and/or the dependent OAR volumes 194a among the set of voxels 122 of the volume 124. In an example embodiment, step 542 involves obtaining tissue measurements that indicate the airway segment 184 tissue type and/or the dependent volume 189 tissue type in each voxel 122 among the set of voxels 122 of the volume 124.

In step 506, utility measurements are obtained that indicate a level of functional utility for each voxel 122 in the volume 124. In one embodiment, for the dependent OAR volume 194a tissue type (e.g. dependent volume 189 tissue type), step 506 involves computing a level of functional utility for each voxel 122 in the dependent OAR volume 194a. In an example embodiment, in step 506 the level of functional utility of each voxel 122 in the dependent volume 189 is determined based on the total ventilation of each volume 189 using equation 2. In other embodiments, for each voxel 344 in the dependent volume 189 tissue type, step 506 involves computing the utility measure value 329 for each voxel 122 in the volume 124. In an example embodiment, the utility measure value 329 for each voxel 344 in the dependent volume 189 is based on the value of equation 1 for that particular voxel 344. In some embodiments, step 506 is similar to step 550 of the method 540 which involves determining the utility measure (e.g. value 329) for each voxel 344 in each dependent volume 189 in the volume 124.

In step 506, for the branching structure tissue type, step 506 involves computing a utility measurement for each branching structure in the set of branching structures. In one embodiment, in step 506 for the airway segment 184 tissue type, step 506 involves computing a utility measurement of each airway segment 184. In some embodiments, step 506 is based on one or more of steps 546 and 548 of the method 540. In one embodiment, the utility measurement of the branching structure 194b (e.g. airway segment 184) is based on a radiosensitivity of the branching structure 194b (e.g. airway segment 184) to damage during the radiation therapy. In an example embodiment, the radiosensitivity of the airway segment 184 to damage is based on a probability of collapse of the airway segment 184, that can be expressed as:

$$Pr_{coll} = \frac{1}{1 + e^{-(\alpha_1 + \alpha_2 \times d + \alpha_3 \times D_{max})}} \quad (3)$$

Where $Pr_{coll}$ is the probability of collapse of the airway segment 184, d is a diameter of the airway segment 184, $D_{max}$ is a maximum point dose (e.g. a minimum dose to a voxel within a 0.01 cubic centimeter (cc) volume receiving the highest dose) and $\alpha_1$, $\alpha_2$ and $\alpha_3$ are fitted parameters. Using logistic regression on sample data, these fitted parameters were solved to be $\alpha_1=-3.63$ (unitless), $\alpha_2=-0.26$ (inverse millimeters or $mm^{-1}$) and $\alpha_3=0.07$ (inverse gray or $Gy^{-1}$), respectively. The value of these parameters depends on the population of airway segments used in regression modeling.

In other embodiments, the utility measurement (or protection priority) of each branching structure 194b is determined in step 506 based on a value of an anatomical parameter of the branching structure 194b. In an embodiment, step 546 involves determining a value of an anatomical parameter (e.g. diameter d in equation 3) of each airway segment 184 in the set of airway segments 184. In an example embodiment, the determined value of the anatomical parameter is used to determine a value of the probability of collapse of the airway segment 184 using equation 3 and this probability value is then used to determine the utility measurement (e.g. dependent on radiosensitivity, e.g. based on a radiation dose-response curve) of each airway segment 184. In other embodiments, the value of the utility measurement of each branching structure 194b (e.g. airway segment 184) is based on the value of the anatomical parameter of the branching structure 194b without the radiosensitivity of the branching structure 194b to damage during the radiation therapy.

In another example embodiment, the utility measurement of each airway segment 184 is obtained based on step 548 which determines the cumulative ventilation for each airway segment 184. In an example embodiment, the cumulative ventilation for each airway segment 184 is based on the value of the FWAS map 350 corresponding to the airway segment 184. In the example embodiment, the determined value of the anatomical parameter is used to determine a value of the probability of collapse of the airway segment 184 using equation 3 and this probability value is then used to determine the radiosensitivity (e.g. radiation dose-response curve) of each airway segment 184.

In step 510, a set of target voxels are determined from the plurality of voxels 122 within the volume 124. This step is performed, using the tissue type measurements obtained in step 504 that indicate target tissue type in the volume 124. The set of target voxels are determined, to encompass the target material 192 that is positioned within the subject 190. However, the set of target voxels is necessarily expanded beyond the target material 192, to account for the uncertainty of the subject 190. FIG. 7A is a block diagram that illustrates an example of a planning target volume 702 that encloses the target material 792, according to an embodiment. As illustrated in FIG. 7A, the planning target volume 702 encompasses the target volume 792 defined by initial imaging (solid line) and the expanded target volume 792' in the secondary position (dotted line) resulting from uncertainty. The planning target volume 702 is used to determine the set of target voxels in step 510, to ensure that all of the target material 792 is within the set of target voxels, over all uncertainties. In some embodiments, the uncertainties arise from the movement of the subject 190. In other embodiments, the uncertainties arise from setup of one or more components of the system 100. In an example embodiment, the planning target volume 702 is formed by expanding the target material 192 by a margin in a range of 2 mm-1 cm.

In step 512, a set of OAR voxels are determined from the plurality of voxels 122 within the volume 124. In some embodiments, step 512 involves determining the set of OAR voxels that enclose an OAR other than the lung (e.g. spine, heart, etc.). In other embodiments, step 512 involves determining a set of OAR dependent volume voxels that enclose the OAR dependent volume 194a (e.g. dependent volume 189). In an example embodiment, step 512 involves determining a respective set of OAR dependent volume voxels that enclose each respective OAR dependent volume 194a (e.g. each dependent volume 189).

Additionally, in still other embodiments, step 512 is based on step 544 that involves determining a set of branching structure (e.g. set of airway segment voxels) voxels from the plurality of voxels 122 that enclose the set of branching structure (e.g. airway segments 184) and/or determining a plurality of subsets of the branching structure voxels that enclose a respective branching structure 194b. In an example embodiment, step 512 includes determining a plurality of airway segment voxels that enclose the set of airway segments and/or determining a plurality of subsets of the airway segment voxels that enclose a respective airway segment 184 [3]. This step is performed, using the tissue type measurements obtained in step 504 that indicate OAR tissue type (e.g. dependent volume 189) and the branching structure tissue type (e.g. airway segment 205) in the volume 124. The set of OAR voxels are determined, to encompass the one or more OARs 194 within the volume 124 and/or one or more dependent OAR volumes 194a (e.g. dependent volume 189) within the volume 124. The set of OAR voxels represent the OAR 194 and/or dependent OAR volume 194a inside the subject 190 to be irradiated the least by the radiation source 170 for each of the one or more OARs 194. The subset of branching segment voxels (e.g. airway segment voxels) represents the branching structure 194b (e.g. airway segment 184) inside the subject 190. Those voxels 122 within the volume 124 that are not determined to be target voxels in step 510 or OAR voxels in step 512 or dependent OAR volume voxels in step 512 or branching structure voxels in step 512 are determined to be normal tissue voxels.

In step 514, a utility measure w, for each OAR voxel 122 is determined, based on the utility measurements at each OAR voxel obtained in step 506. In an example embodiment, the value of the utility measure w, for each OAR voxel 122 is used to determine a degree of minimization of the radiation dose for each OAR voxel 122. In another example embodiment, the value of the utility measure w, for each dependent OAR voxel (e.g. volume 189 voxel) is used to determine a degree of minimization of the radiation dose for each dependent OAR volume 194a (e.g. dependent volume 189). In one embodiment, the utility measure w, for each OAR voxel is based on the total ventilation value from equation 2. Since the utility measure w, has a maximum value for those dependent volumes 189 with a high total ventilation value (e.g. based on equation 2), the minimization of the radiation is enhanced for those dependent volumes 189 with a high total ventilation value.

In another embodiment, step 514 involves determining a utility measure $w_j$ for each branching structure 194b (e.g. airway segment 184), based on the utility measurements for each branching structure 194b obtained in step 506. In an example embodiment, in step 514 the value of the utility measure $w_j$ for each branching structure 194b is based on step 552 of the method 540, which determines the utility measure $w_j$ for the branching structure 194b. In one embodiment, step 552 involves determining the utility measure $w_j$ for the airway segment 184 based on one or more of the value of the anatomical parameter of the airway segment 184 (e.g. to determine a radiosensitivity of the airway segment 184 to damage, such as a value of the probability of collapse of the airway segment 184 using equation 3) and/or the cumulative ventilation of the airway segment 205 (from step 548). In an example embodiment, the value of the utility measure $w_j$ for each airway segment 184 is used to determine a degree of priority to lower the radiation dose for each airway segment 184 to below the radiation dose found for susceptibility to damage. Since the utility measure $w_j$ has a high value for those airway segments 184 with a high cumulative ventilation value (e.g. value of the FWAS map in FIG. 3G for each airway segment 184), the minimization of the radiation is enhanced for those airway segments 184 with a high cumulative ventilation value.

In some embodiments, an objective function is determined, which is subsequently used to optimize the radiation therapy (RT). In step 516, a value of an objective function includes a sum of a computed radiation dose violation (e.g. difference between a delivered dose and dose constraint) for OAR voxels 122 weighted by the utility measure Iv, (from step 514) at the OAR voxels 122 and a computed radiation dose violation (e.g. difference between a delivered dose and dose constraint) for branching structure 194b voxels (e.g. airway segment 184 voxels) weighted by the utility measure $w_j$ at the branching structure 194b (from step 514). Dose violation is defined as the radiation dose delivered minus the dose constraint or radiation dose considered safe, e.g., $\Delta D_i = (D_i - D_i^c)$. Only positive values (overdosing) are violations. That part of the objective function can be expressed as:

$$\Sigma_{i \in OARs} w_i \times \Delta D_i + \Sigma_{j=1}^{Nairways} w_j \times \Delta D_j \quad (4)$$

Where $w_i$ is the utility measure of the OAR voxel 122 of index i from step 514; $\Delta D_i$ is the dose violation for the OAR voxel 122 of index i, $N_{airways}$ is the number of airway segments 184, $w_j$ is the utility measure of each airway segment 184 with index j from step 514 and $\Delta D_j$ is the dose violation for each airway structure 184 with index j. In an embodiment, the complete objective function sums equation 4 with similarly calculated weighted dose violation terms for target material 192.

To perform step 516, for each voxel 122 in the volume 124, if the voxel 122 encloses OAR tissue (e.g. OAR 194 and/or dependent OAR volume 194a) then the computed dose violation $\Delta D$, is multiplied by $w_i$. Additionally, for each branching structure 194b (e.g. airway segment 184) in the volume 124, the computed dose violation $\Delta D_j$ for the airway segment 184 is multiplied by $w_j$. These contributions are then summed for all OAR voxels 122 and branching structures 194b (e.g. airway segments 184) in the volume 124. As previously discussed in step 514, since the utility measure $w_i$ has an increased value for OAR voxels 122 with a high utility measurement, the computed dose violation $\Delta D$, in equation 4 will have a higher priority of minimization for OAR voxels 122 with high utility measurements, as discussed in step 518 below. Similarly, since the utility measure $w_j$ has an increased value for branching structures 194b (e.g. airway segments 184) with a high utility measurement, the computed dose violation $\Delta D_j$ in equation 4 will have a higher priority of minimization for branching structures 194b (e.g. airway segments 184) with high utility measurements, as discussed in step 518 below.

The function in equation 4 factored OAR tissue type and branching structure tissue type, and needs to be complete as an objective function by also considering target tissue type. In an example embodiment, an objective function is defined to include the computed dose violation for the target tissue voxels within the volume 124, which can be expressed as:

$$F = \Sigma_{i \in OARs} w_i \times \Delta D_i + \Sigma_{j=1}^{Nairways} w_j \times \Delta D_j + \Sigma_{k \in PTV} \Delta D_k \quad (5)$$

Where $\Delta D_k$ is the dose violation to the target voxel 122 of index k. In some embodiments, dose violation for the target tissue type (e.g. PTV) is defined as the radiation dose prescribed (or considered desirable) minus the radiation dose delivered. In some embodiments, only positive values are counted as violations. In an embodiment, the general understanding is that higher doses to PTV voxels are not disadvantageous. Therefore, in some embodiments, there is no need to consider it a violation if a PTV voxel receives higher than prescribed radiation dose. However, in other embodiments, a threshold is set for such higher doses (e.g., 120% of the prescribed dose) including one more set of dose violations for PTV where dose violation is defined as the radiation dose delivered minus the threshold radiation (e.g., 120% of the prescribed dose). $\Sigma_{k \in PTV} \Delta D_k$ in equation 5 sums up all dose violations explained. In one embodiment, the utility measure for branching structure 194b and dependent OAR 194a were calculated based using functionality of the plurality of the voxels while utility measure for the other OAR 194c was approximated based on its conventionally used protection priority.

In some embodiments, the objective function is used to optimize the radiation therapy (RT). In step 518, a radiation plan is solved that minimizes the objective function defined above in equation 5 subject to constraints that the total dosage at each voxel 122 is not violating certain lower and upper bounds for the tissue type associated with the voxel 122 taking into account one or more uncertainty scenarios caused by subject 190 movement phases. These constraints are expressed as:

$$F = \sum_{i \in OARs} w_i \times (D_i - D_i^c)^2 \times f_i + \qquad (6)$$

$$\sum_{j=1}^{N_{airways}} w_j \times (D_j - D_j^c)^2 \times f_j + \sum_{k \in PTV} (D_k - D_k^c)^2 \times f_k$$

$$f_i(\text{upper dose constraints}) = \begin{cases} 1, & \text{if } D_i > D_i^c \\ 0, & \text{if } D_i \leq D_i^c \end{cases} i \in OARS \qquad (7)$$

$$f_j(\text{upper dose constraints}) = \begin{cases} 1, & \text{if } D_j > D_j^c \\ 0, & \text{if } D_j \leq D_j^c \end{cases} j \in \text{Airways} \qquad (8)$$

$$f_k(\text{upper dose constraints}) = \begin{cases} 1, & \text{if } D_k > D_k^c \\ 0, & \text{if } D_k \leq D_k^c \end{cases} k \in PTV \qquad (9)$$

$$f_k(\text{lower dose constraints}) = \begin{cases} 1, & \text{if } D_k < D_k^c \\ 0, & \text{if } D_k \geq D_k^c \end{cases} k \in PTV \qquad (10)$$

Where $D_i^c$ is the dose constraint for the OAR voxel of index i, $D_j^c$ is the dose constraint for airway segment 205 of index j and $D_k^c$ is the dose constraint for target voxel of index k. Additionally, f is a binary value that is based on whether the dose to each respective tissue is greater than or equal to and less than the dose constraint for that respective tissue.

In an embodiment, the objective function in equation 6 considers overdoses (e.g. where the dose exceeds the dose constraint) for OAR voxels 122 and branching structures 194*b* (e.g. airway segments 184) and does not include underdoses (e.g. where the dose is equal to or less than the dose constraint) for OAR voxels 122 and branching structures 194*b* (e.g. airway segments 184). In another embodiment, the objective function in equation 6 considers both underdoses (e.g. where the dose is less than the dose constraint) and overdoses (e.g. where the dose exceeds the dose constraint) for target tissue voxels 122. An underdose to the target voxels is not desired, in order to kill all tumor cells in the target voxels. Similarly, an overdose to the target voxels is also not desired, as it reduces uniformity of the dose delivered to the target voxels. Additionally, although equations 5 and 6 show the objective function in a linear/quadratic formulation, this is merely one example in which the objective function can be written. In another embodiment, the objective function can be written in any formulation of the planning problem, such as a quadratic objective function.

In some embodiments, the RT plan is determined by solving equations 6 through 10 for the values of $D_i$, $D_j$, $D_k$ over all voxels 122. In an embodiment, the respective dose $D_i$, $D_j$, $D_k$ to each OAR voxel, airway branching structure 194*b* (e.g. airway segment 184) or target tissue voxel are solved for by minimizing the objective function of equation 5 or 6. These dose matrices are calculated beforehand as input to the optimization, as discussed in [4], which is incorporated by reference herein. In one example embodiment, they are exported from a commercial treatment planning system that uses clinically accepted dose calculation algorithms. In one example embodiment, using preconfigured apertures (e.g. beam shapes for beams 172) for the radiation source 170, the corresponding monitor units (e.g. aperture intensity) were optimized using the minimization of equation 6 and the constraints of equations 7 through 10 as disclosed in [5] and [6], which are incorporated by reference herein. The preconfigured apertures are creating after a preliminary optimization process (e.g., in a commercial treatment planning system). Aperture intensity weights scaled the dose deposition matrices corresponding to each aperture.

In an example embodiment, for those voxels 122 of the OAR that have high utility, the value of the utility measure w, is relatively high and thus the overdose (e.g. difference between Di and $D_i^c$) of each beamlet (beam element) directed at the OAR voxel 122 will be relatively low, in order to minimize the overall term $w_i \times (D_i - D_i^c)$ in equation 6 for that voxel 122. In an example embodiment, for those branching structures 194*b* (e.g. airway segments 184) that have high utility, the value of the utility measure $w_j$ is relatively high and thus the overdose (e.g. difference between Dj and $D_j^c$) of each beamlet directed at the airway segment 184 will be relatively low, in order to minimize the overall term $w_j \times (D_j - D_j^c)$ in equation 6 for that airway segment 184.

In some embodiments, step 547 involves determining the dose constraint $D_j^c$ in equation 6, based on the susceptibility to damage of the branching structure 194*b* (e.g. equation 3 for the airway segment 184). In an embodiment, the dose constraint $D_j^c$ to the airway segments 184 is based on a threshold value of the probability of collapse $Pr_{coll}$ in equation 3. The dose constraint $D_j^c$ is then determined by solving equation 3 for $D_{max}$ and using the threshold value (e.g. 0.05 or 5%) for the probably of collapse $Pr_{coll}$:

$$D_j^c = D_{max}(Pr_{coll} = 0.05)$$

$$D_j^c = \frac{-1}{\alpha_3}\left[\ln\left(\frac{1}{Pr_{coll}} - 1\right) + \alpha_1 + \alpha_2 \times d\right]$$

And using the threshold value (e.g. 0.05) for the probability of collapse and the values of the fitted parameters from linear regression:

$$D_j^c = 9.8 + 3.7 \times d \qquad (11)$$

In this embodiment, a linear relationship is established between the dose constraint to each branching structure 194*b* (e.g. airway segment 184) and the diameter of the respective branching structure 194*b* (e.g. airway segment 184). For purposes of the minimization of the objective function, if the probability of collapse of the airway segment 184 is equal to or higher than the threshold value, then the airway segment 184 is considered collapsed and open otherwise. Additionally, if the dose delivered to an airway segment 184 is lower than the dose constraint calculated with equation 11, no collapse is assumed (e.g. the airway segment 184 remains open after treatment with 95% probability). The threshold value (e.g. 0.05) is selected since it was found that this value was a limit to provide realistic dose results. However, the threshold value is not limited to this particular value and in some embodiments can be selected within a range from about 50% to about 100%.

In some embodiments, the method accounts for motion of each tissue type during a breathing cycle, by considering a dose received by each tissue type voxel over multiple phases of the breathing cycle in order to calculate the total dose received at that voxel. In an embodiment, for purposes of minimizing equation 6 using the constraints in equations 7 through 10, the computed dose D to one or more of the OAR tissue type, target tissue type and branching structure tissue type is based on a computed dose to each respective tissue type over multiple phases of a breathing cycle. This advantageously accounts for motion of one or more of the OAR tissue type, target tissue type and airway segment tissue type during the breathing cycle. In one embodiment, the computed dose D is a weighted average of a computed dose to each respective tissue type at multiple phases of the breathing cycle where the weights are defined by calculating average time subject 190 spends at each phase. In another embodiment, equal weights are assigned to all the phases.

Figure 8A:
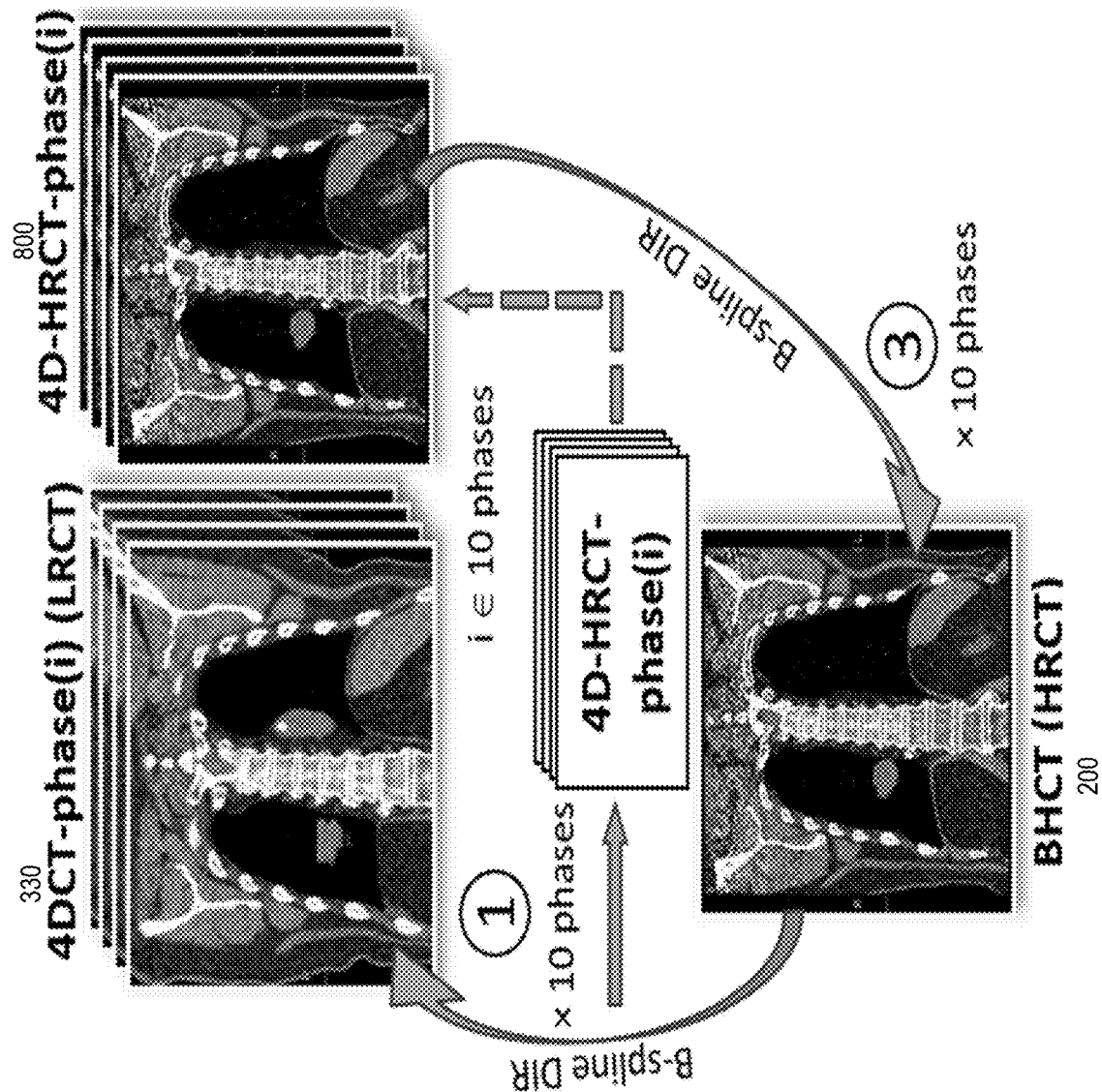
FIG. 8A is an image that illustrates an example of a 4DCT over multiple phases of a breathing cycle, high resolution 4DCT (4D-HRCT) and a breath-hold phase (BHCT) image of a subject, according to an embodiment.

In some embodiments, the tissue type measurements (e.g. step 504) are performed over multiple phases of the breathing cycle. In an embodiment, step 562 of the method 560 involves obtaining tissue measurements of the branching structure 196 (e.g. airway segment 184) at multiple phases of the breathing cycle. FIG. 8A is an image that illustrates an example of a 4DCT 330 of the subject 190 that is obtained over multiple phases (e.g. between about 4 phases to 16 phases or about 10 phases) of a breathing cycle and a BHCT 200 image of the subject, according to an embodiment. In an embodiment, ten DIRs are performed from the BHCT 200 to the ten phases of the 4DCT, to obtain 4D-HRCT 800 of the subject 190.

Figure 8B:
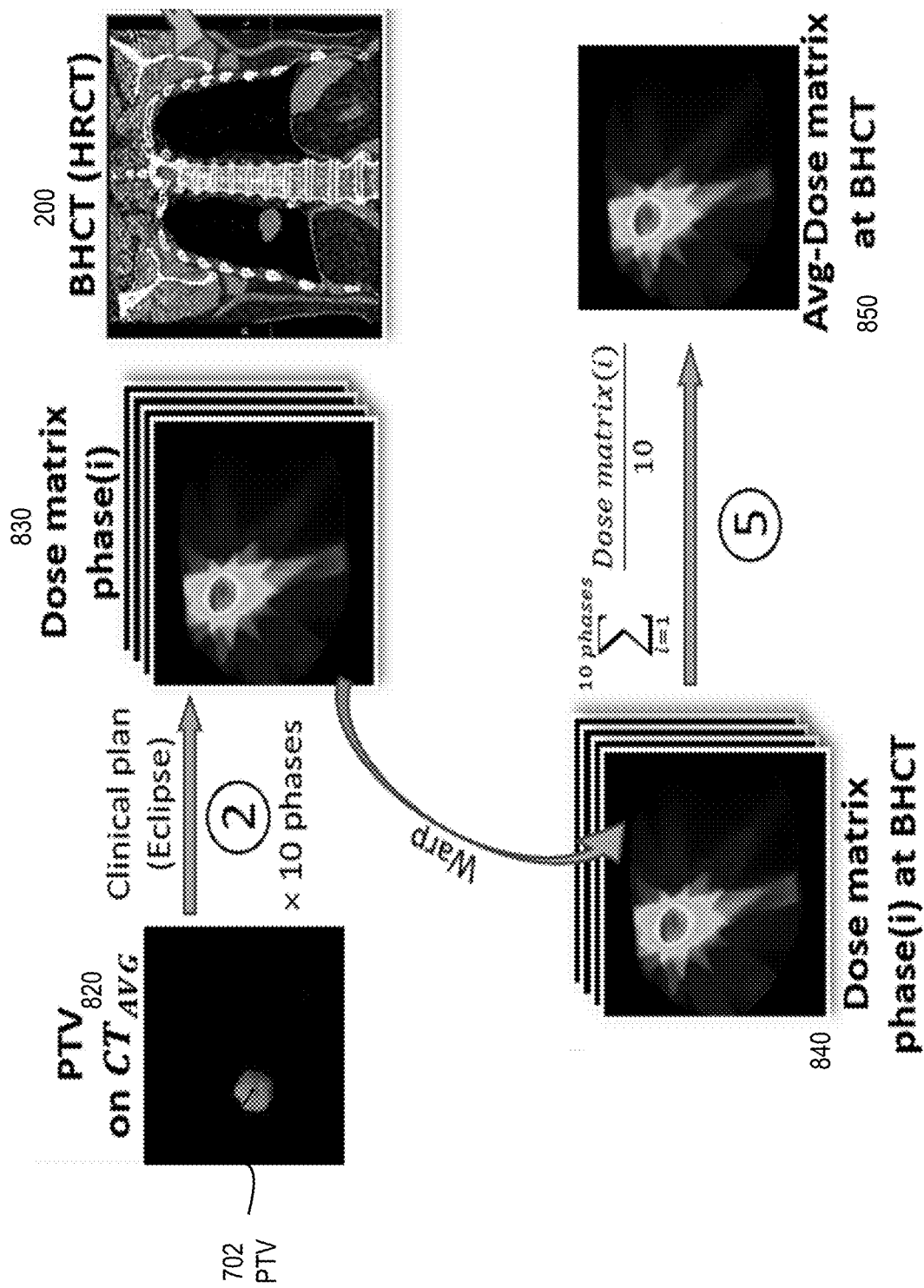
FIG. 8B is an image that illustrates an example of a planning target volume (PTV) and a dose matrix of a radiation plan of each breathing cycle phase based on the PTV and 4DCT of FIG. 8A, according to an embodiment.

In these embodiments, after measuring the tissue type at multiple phases of the breathing cycle, a computed dose to each voxel 122 is determined for each of the multiple phases (e.g. to be used in equation 6). FIG. 8B is a $CT_{avg}$ image 820 that illustrates an example of a PTV 702. As appreciated by one of ordinary skill in the art, the $CT_{avg}$ image 820 is an image where the intensity of each voxel is based on an average value of the voxel for the ten phase images of the 4DCT 330. In an embodiment, step 564 of the method 560 involves determining a dose to the branching structure (e.g. airway segment 184) at each phase of the breathing cycle, by calculating dose in RT plans based on the tissue measurements obtained in step 562 (e.g. 4D-HRCT 800). In an embodiment, the PTV 702 from the $CT_{avg}$ image 820 is used with each of the ten respective 4D-HRCT 800 images of FIG. 8A for each respective phase of the 4D-HRCT 800 to generate a respective RT plan (e.g. by minimizing equation 6). In an embodiment, results are shown in the dose matrix 830 of FIG. 8B, which includes a respective dose matrix for each phase of the 4D-HRCT 800.

Figure 8C:
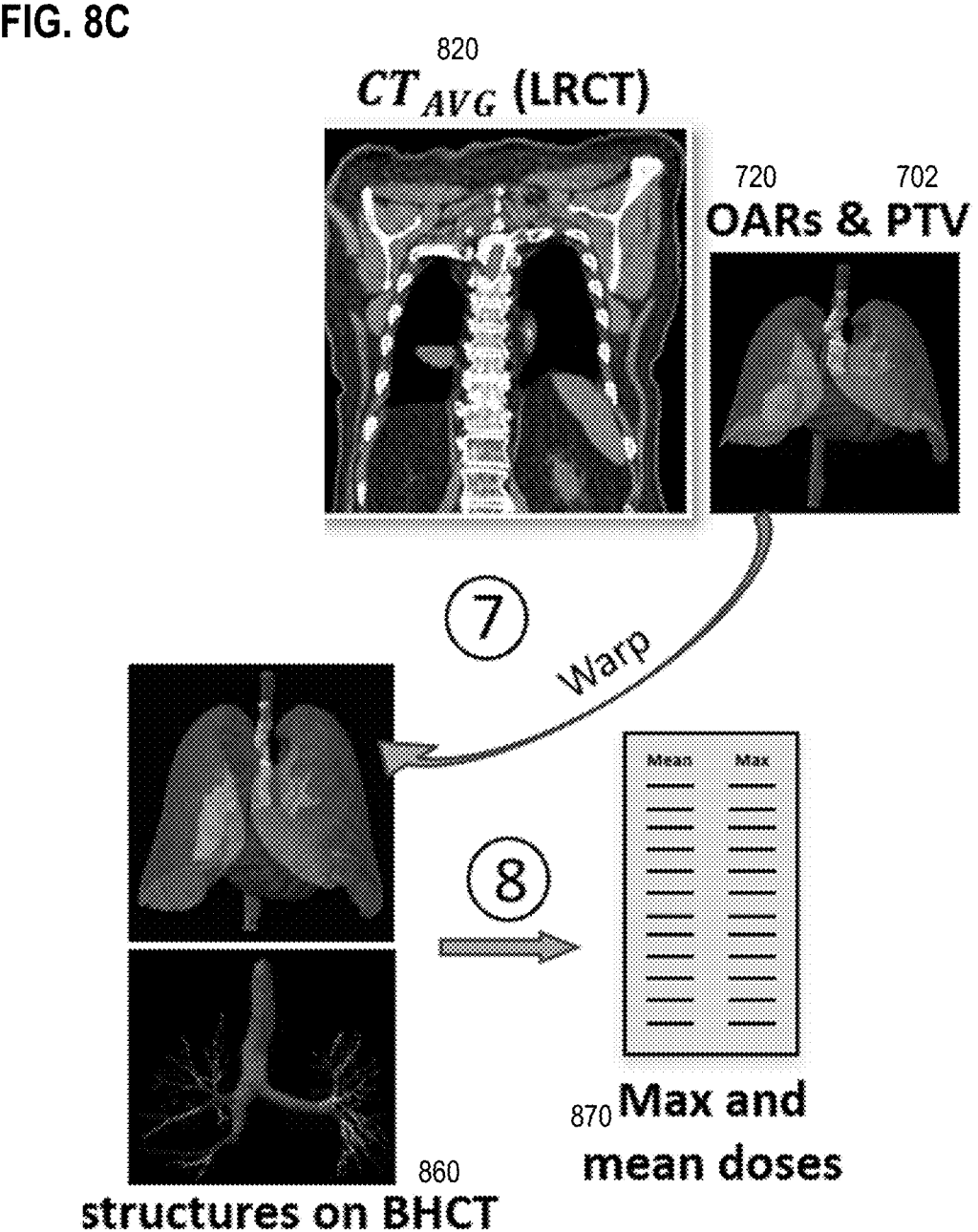
FIG. 8C is an image that illustrates the example registration of OAR and PTV from the low resolution CT (LRCT) to the BHCT image, according to an embodiment.

In some embodiments, after determining the dose to each voxel 122 over the multiple phases, the computed dose D (e.g. in equation 6) is determined for each tissue type that is used to optimize the RT plan. In an embodiment, step 566 of the method 560 includes calculating a computed dose for the radiation treatment plan to the branching structure 194b (e.g. airway segment 184) over the multiple phases of the breathing cycle. In an embodiment, the dose matrix 830 is then registered with a reference image (e.g. BHCT 200) and thus ten DIRs are performed on the dose matrix 830 from the 4D-HRCT to the BHCT 200, resulting in the dose matrix 840 depicted in FIG. 8B. In an embodiment, the dose matrix 840 includes a respective dose matrix for each phase of the 4DCT, where the respective dose matrix is registered with the BHCT 200. In an embodiment, in step 566 an average dose is computed for each tissue type, by averaging the dose matrix 840 for the ten phases for each OAR voxel 122, target voxel 122 and/or airway segment 205. This results in an average dose matrix 850 registered to the BHCT 200. FIG. 8C is an image that illustrates the OARs 720 and PTV 702 in the BHCT image 860, according to an embodiment. In an embodiment, to further include the OAR 720 in the BHCT image 860, an additional DIR is performed from the $CT_{avg}$ image 820, thereby applying DVFs to the OAR 720 and PTV 702. In another embodiment, the average or mean dose ($D_{mean}$) and maximum dose ($D_{max}$) 870 for each OAR voxel 122, target voxel 122 and/or airway segment 184 is calculated using the respective dose matrix 840 for the ten phases. In one example embodiment, in step 518 the computed dose D for one or more of the OAR tissue type, target tissue type and/or airway segment in equation 6 is based on the mean dose ($D_{mean}$) for that particular tissue type. In an example embodiment, the average or mean dose is especially used for branching structures 194b (e.g. airway segments 184) that are sufficiently small so that they vary position relative to the beam 172 (e.g. exit the beam 172 at one or more phases), as discussed with respect to FIGS. 1D and 1E.

In step 520, the radiation source 170 is operated according to the radiation plan solved in step 518. As depicted in FIG. 4, the shape or direction of the beam 172 from the radiation source 170 is controlled by selectively positioning rectangles (e.g. collimator leaves) at various locations within a head of the radiation source 170. The intensity of the beam 172 from the radiation source 170 is adjustable and may be delivered at selective intensities over selective time intervals. In an example embodiment, the control process 140 within the computer system 150 solves for the radiation plan in step 518. In step 520, the computer system 150 transmits signals to the radiation source 170 according to the radiation plan. In an example embodiment, the computer system 150 transmits signals to the radiation source 170 such that the intensity and shape of the beam 172 at each OAR voxel 122 minimizes the radiation dose delivered to high utility volumes 189 and/or such that the intensity and shape of the beam 172 at each airway segment 184 minimizes the radiation dose delivered to high utility airway segments 184. RT plans are generally composed of several beams and the computer system transmits signals to control shape and intensity for all the beams.

2. EXAMPLE EMBODIMENTS

In some embodiments, data from a sample of subjects was used to solve for the values of the fitted parameters ($\alpha 1$, $\alpha_2$ and $\alpha_3$) in equation 3. In an embodiment, the values of the fitted parameters in equation 3 were solved for using logistic regression on sample data. CT images were obtained before and after (e.g. 8 to 14 months after) each subject received a radiation treatment plan. Under institutional review board (IRB) approval, pre (<3 months) and post treatment (median follow-up: 8.5 months) diagnostic quality CT scans (e.g. ≤1 mm-slice thickness) were retrospectively collected from 26 patients treated with lung stereotactic ablative radiotherapy (SAbR) (e.g. 50-60 Gray or Gy in 3-5 fractions). The 26 patients were selected from 150 lung cancer patients who were treated with SAbR between 2012 and 2014. The selection criteria for the study was lung cancer patients treated with SAbR; follow-up CT scan between 8 and 14 months post treatment and image quality of the patient's diagnostic and follow-up CT scan to be high enough so the bronchial tree could be auto segmented down to several levels.

Figure 6A:
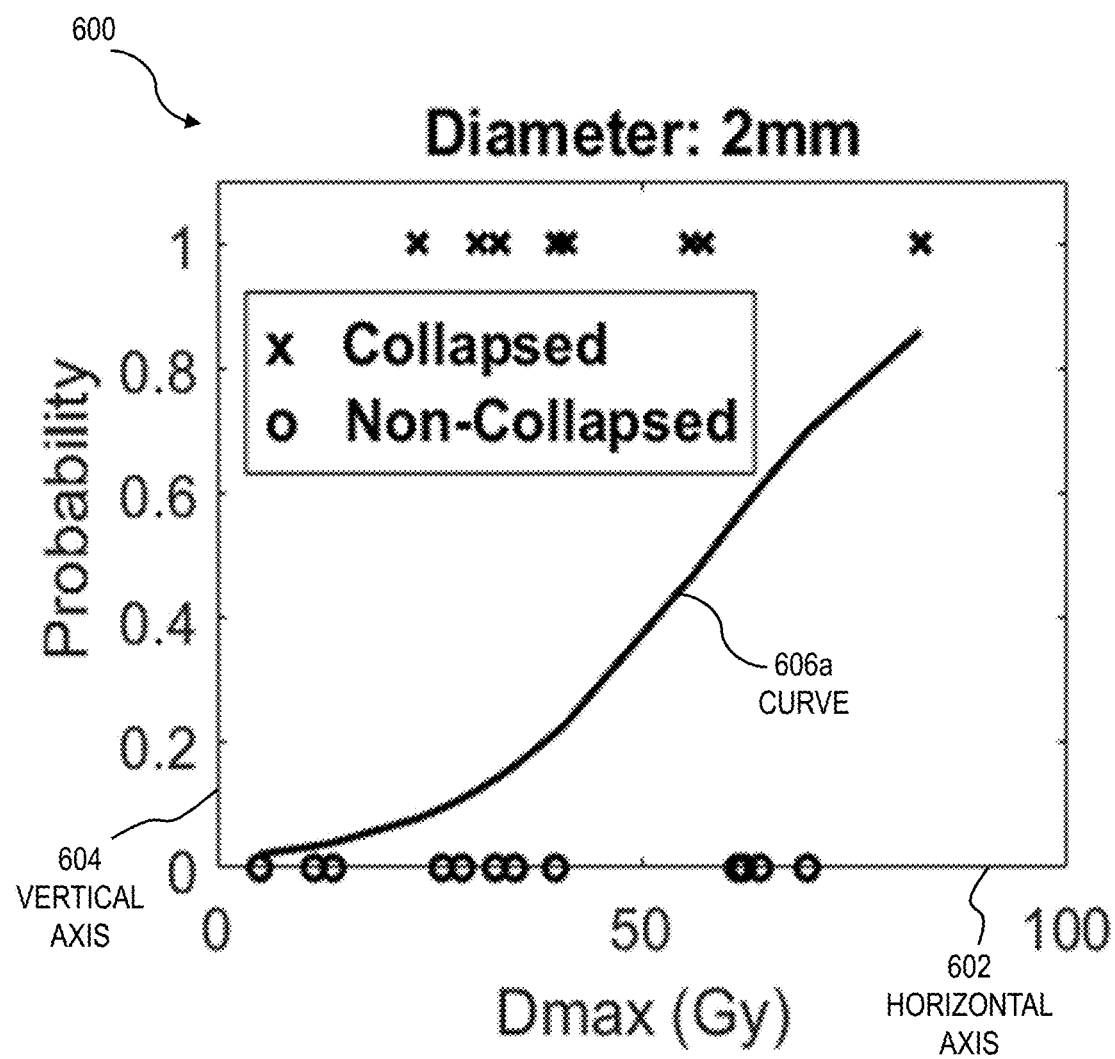
FIGS. 6A through 6I are graphs that illustrate an example of curves that indicate a susceptibility to collapse of airway segments based on maximum dose, for different anatomical parameter values of the airway segments, according to an embodiment.
Figure 6B:
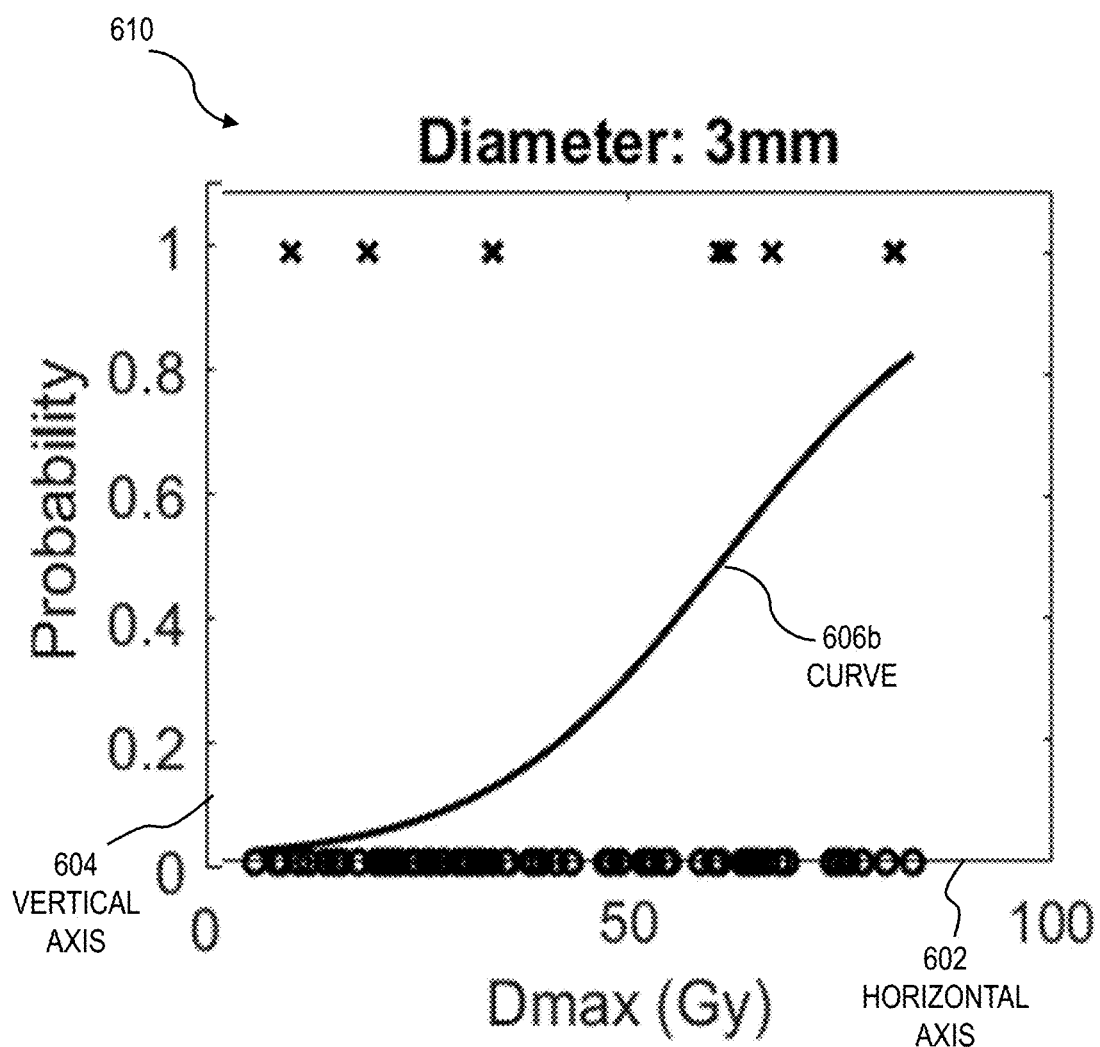
Figure 6C:
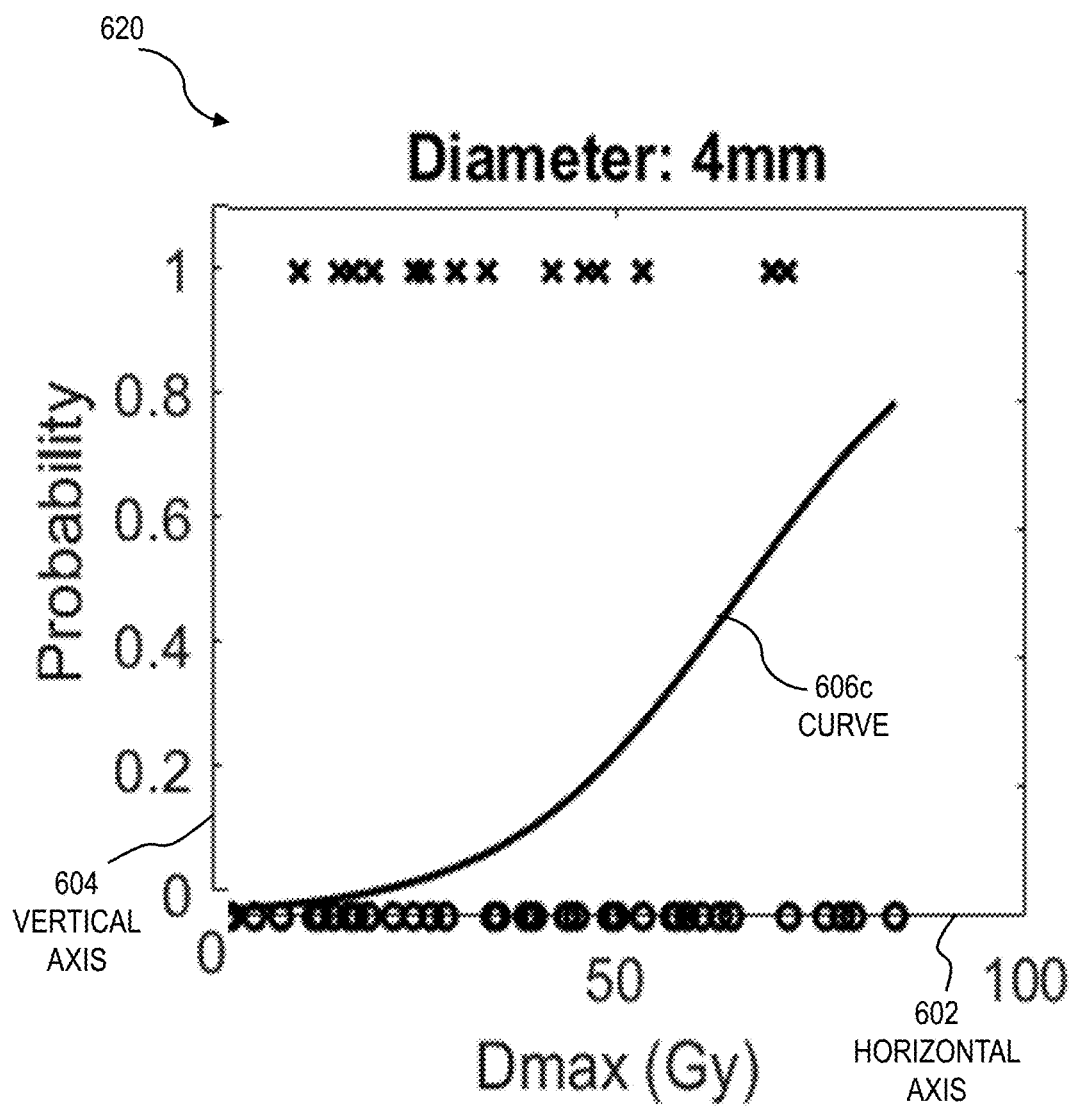
Figure 6D:
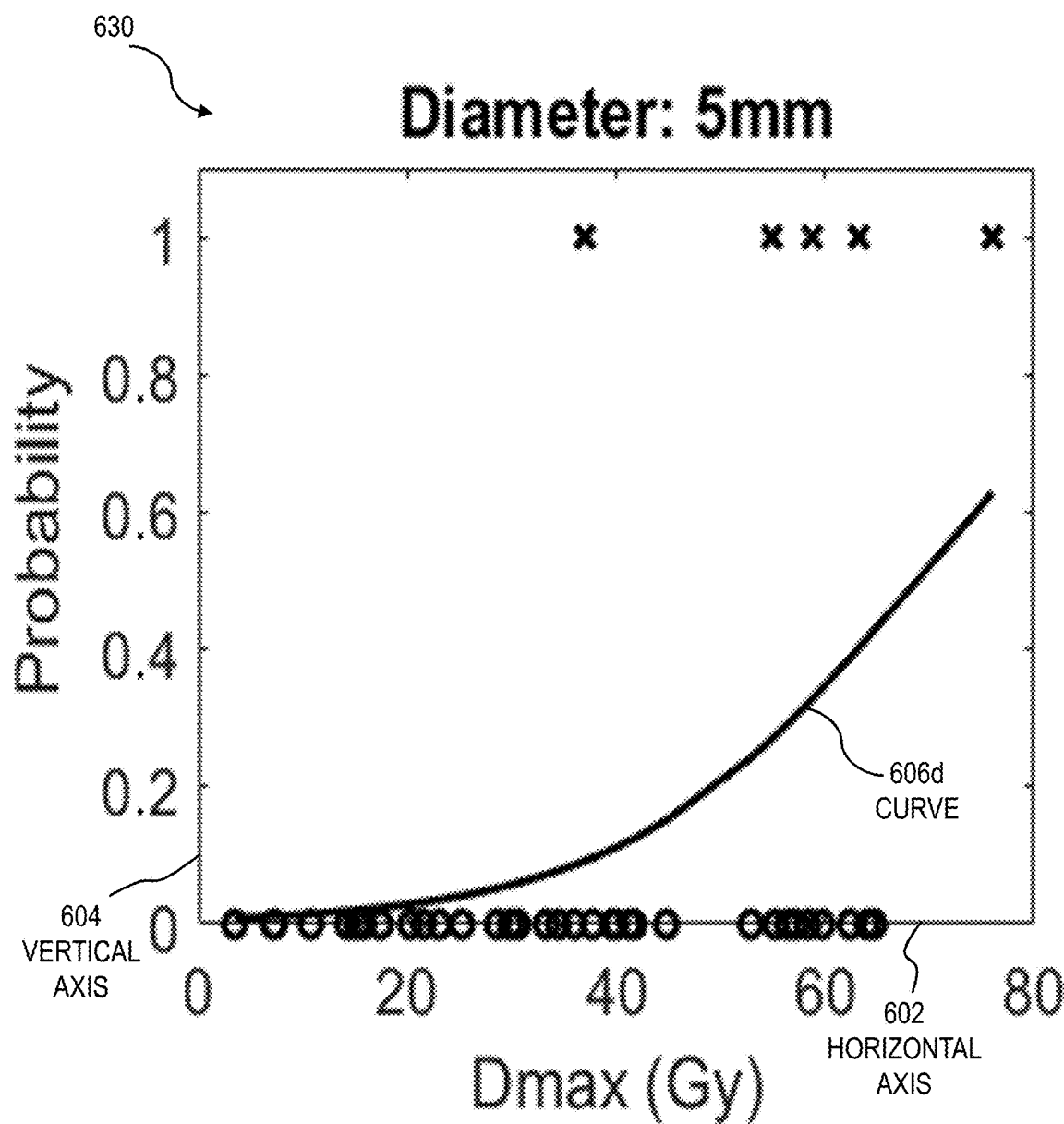
Figure 6E:
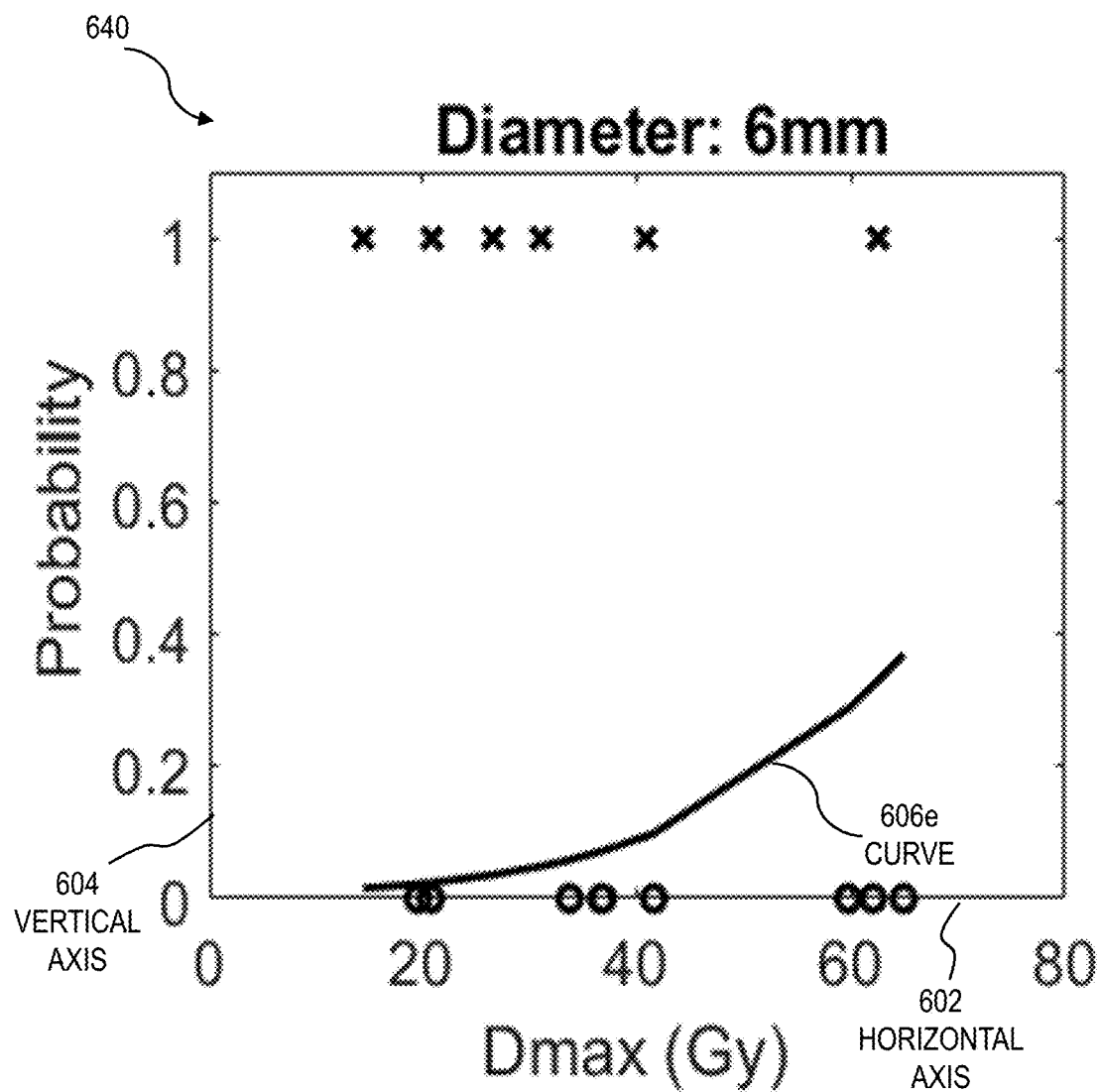
Figure 6F:
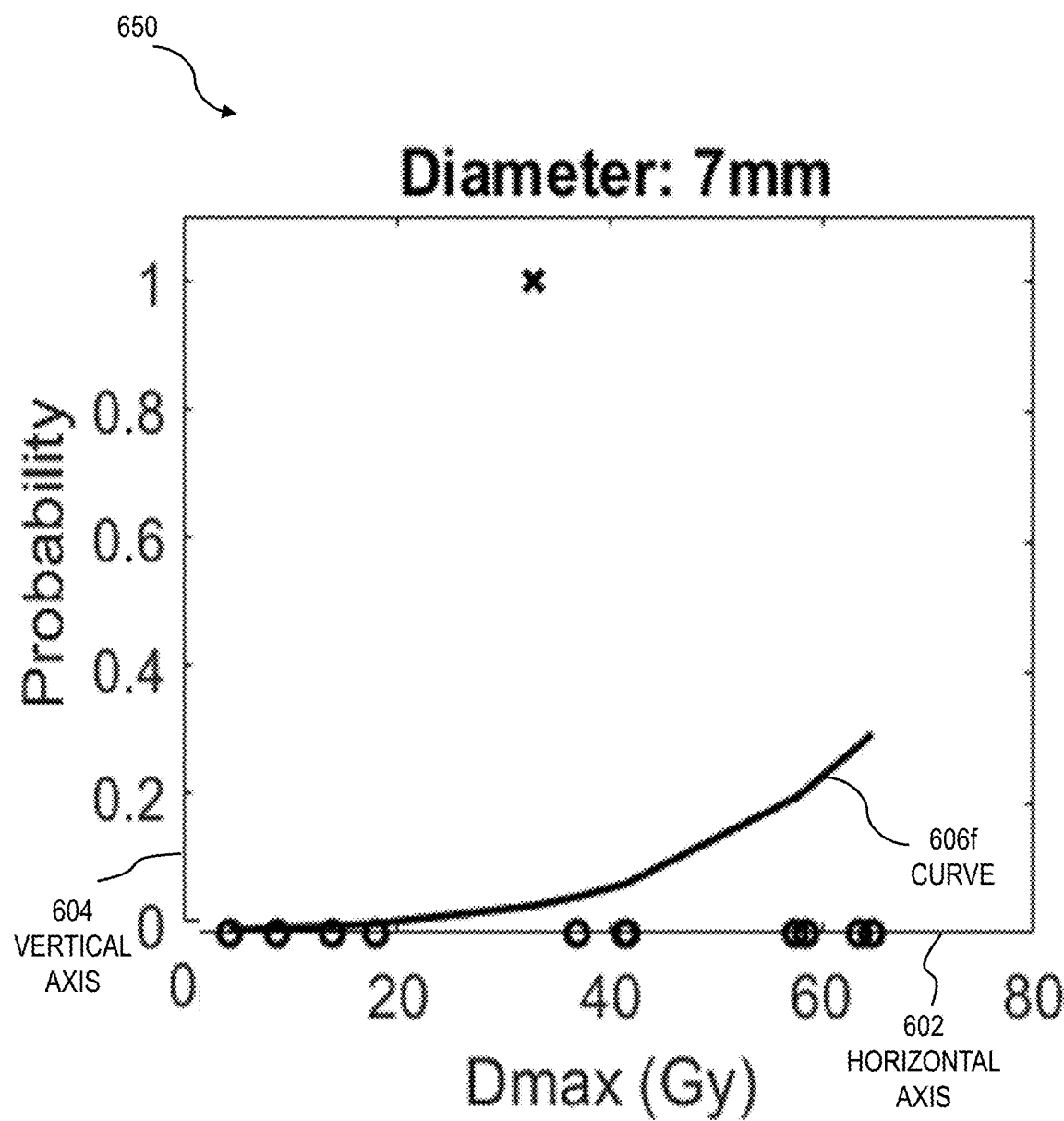
Figure 6G:
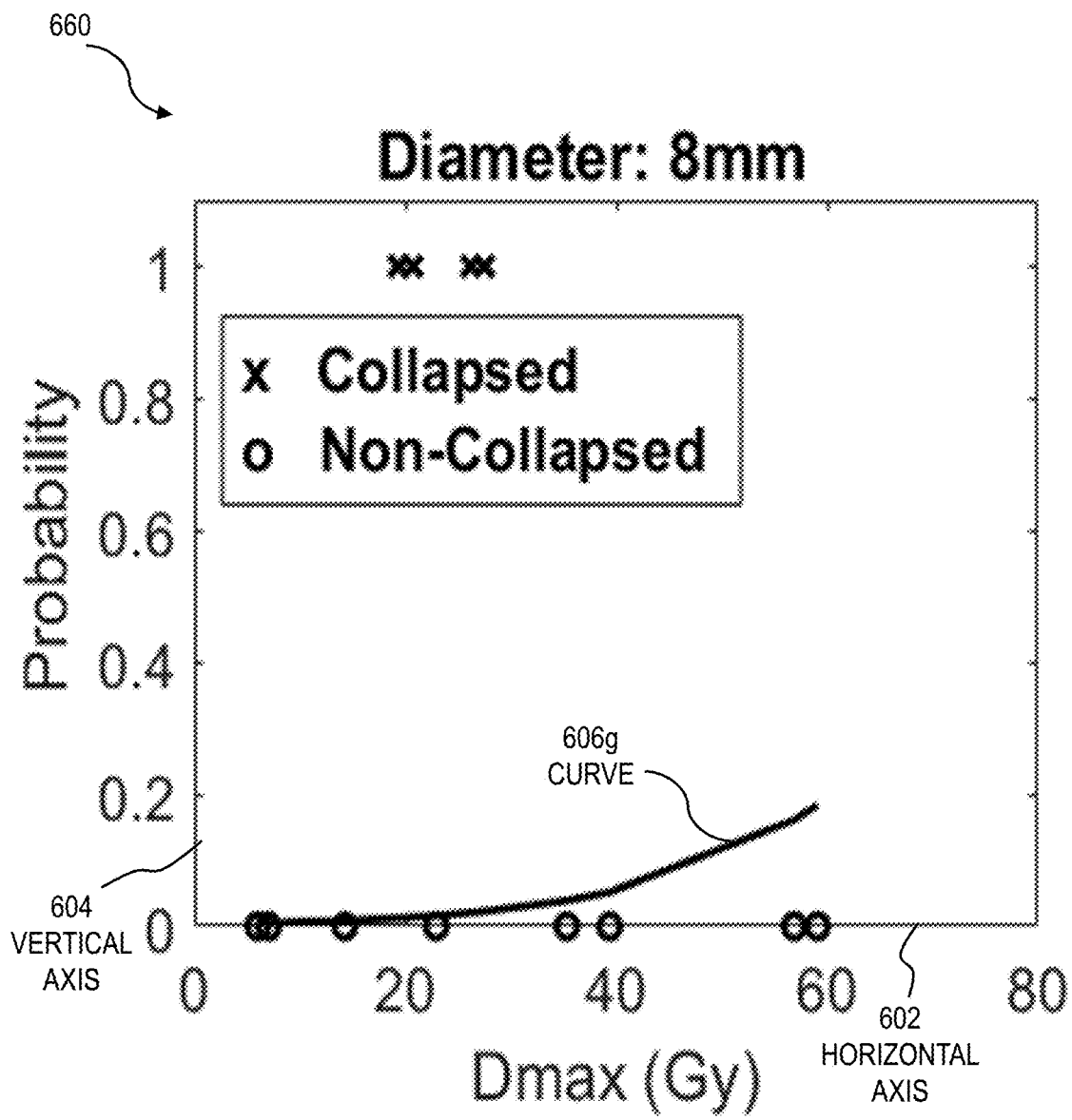
Figure 6H:
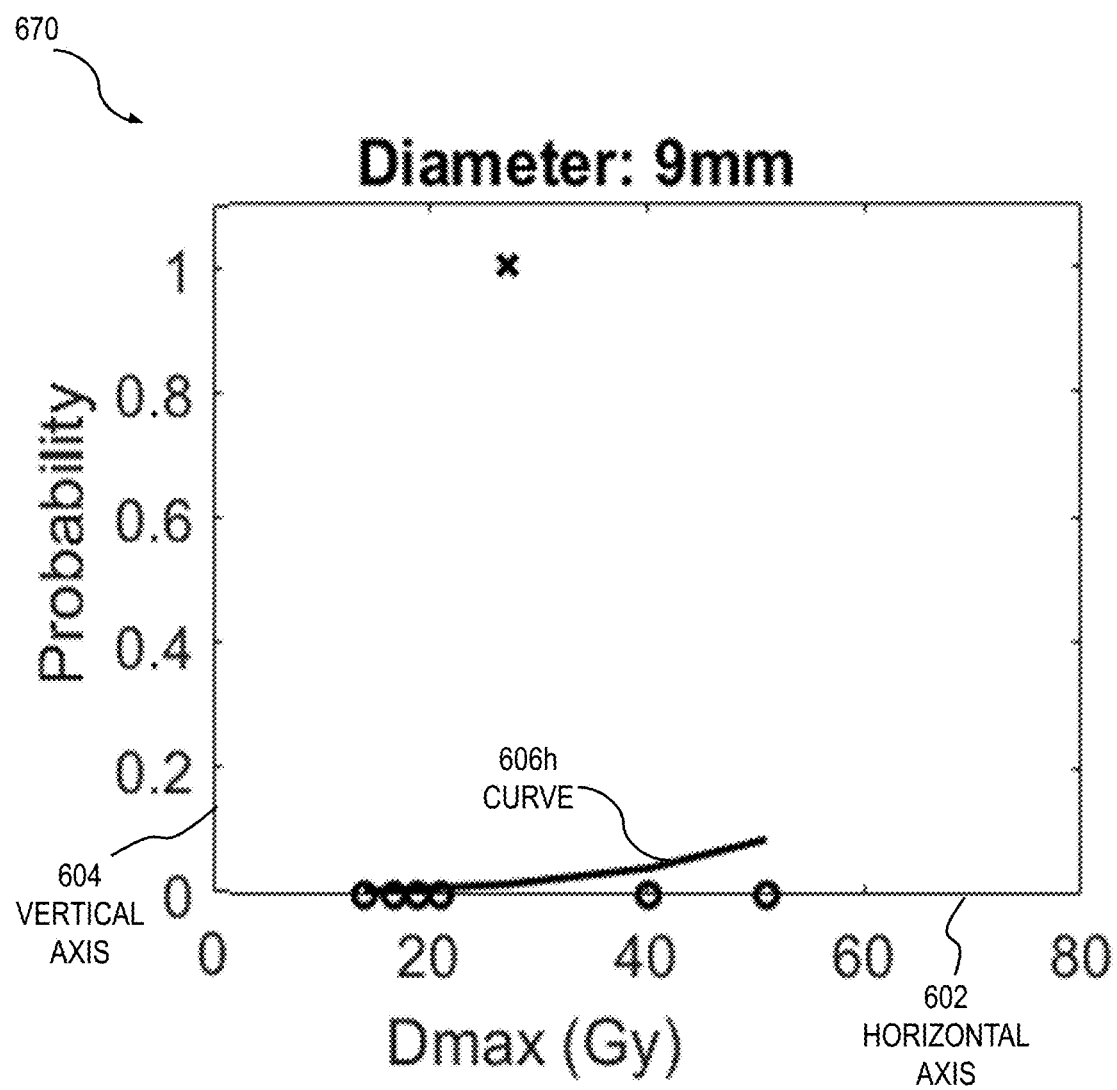
Figure 6I:
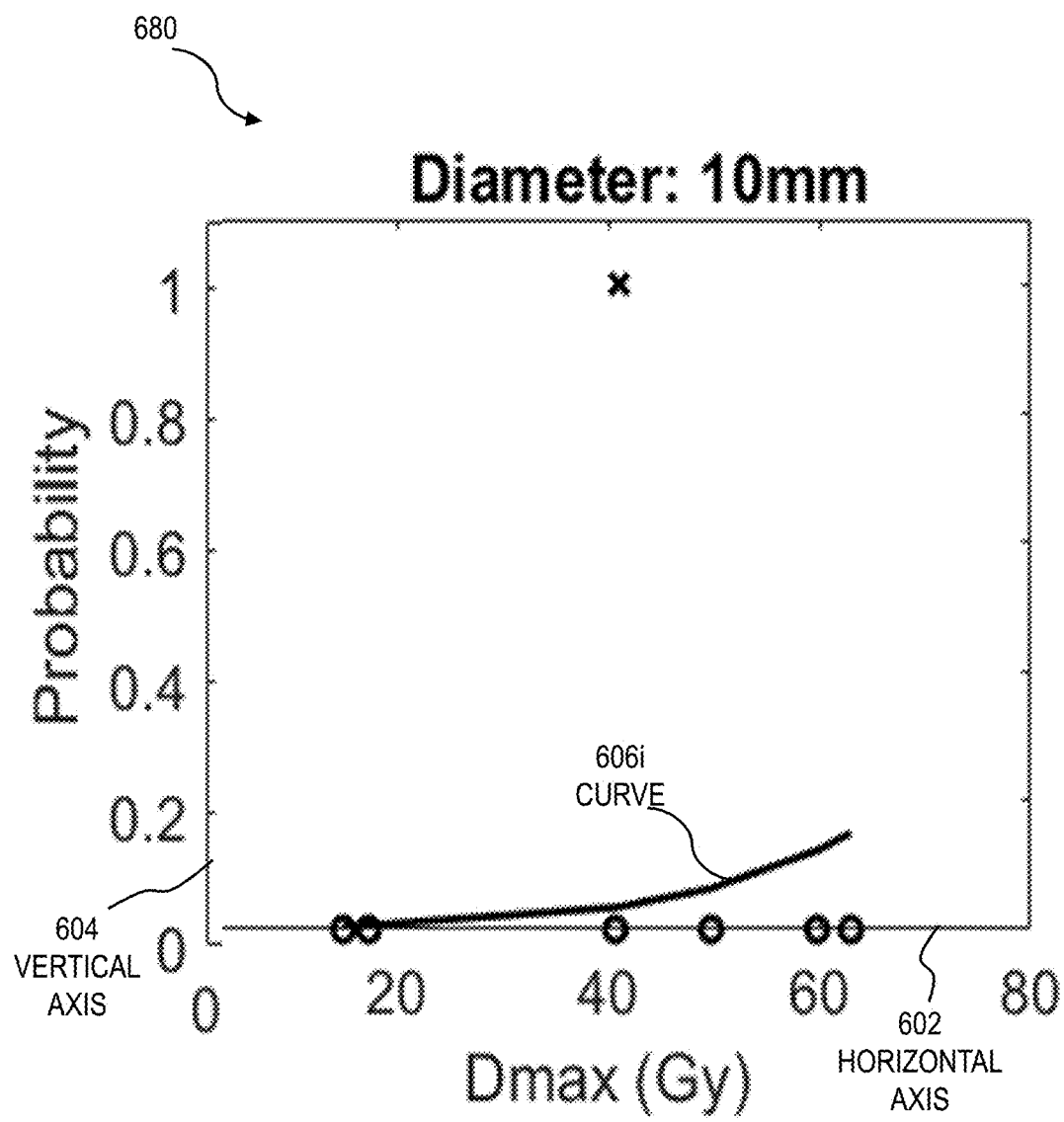

A determination was made, based on comparing the before and after images, whether each airway segment 184 collapsed, as well as the value of the anatomical parameter (e.g. diameter d) of the airway segment 184 and maximum dose ($D_{max}$) received by each airway segment 184. This sample data was then presented in FIGS. 6A through 6I, as "x" (collapsed airway segment) and "o" (non-collapsed airway segment). FIGS. 6A through 6I are graphs 600 that illustrate an example of curves 606 that indicates a susceptibility to collapse of airway segments 184 based on a maximum dose, for different anatomical parameter values of the airway segments, according to an embodiment. The horizontal axis 602 of each graph 600 is maximum dosage received by the airway segment 184 in units of gray (Gy). The vertical axis 604 of each graph 600 is a probability of collapse (unitless). In an embodiment, the curves 606 in each of FIGS. 6A through 6I is based on a best fit to the sample data presented in each graph 600. In one embodiment, curve 606a of FIG. 6A depicts the sample data for airway segments 184 with a diameter of about 2 millimeters (mm) and curve 606a that is based on a best fit with the sample data. FIGS. 6B through 6I similarly depict curves 606b through 606i that are based on a best fit for the sample data for each of the respective integer diameter values of the airway segment 184 from 3 mm through 10 mm. In an example embodiment, the curves 606 of FIGS. 6A through 6I are used to solve for the values of the fitted parameters ($\alpha_1$, $\alpha_2$ and $\alpha_3$) in equation 3 using logistic regression.

Although step 518 discussed one embodiment where the computed dose D in equation 6 is determined by averaging a computed dose received by the respective tissue type at multiple breathing phases, other embodiments of step 518 employ other criteria to determine the computed dose D and account for motion due to the breathing cycle. In one embodiment, the BHCT image 200 is used, where the $CT_{avg}$ 820 image structures and PTV 720 are deformed to the BHCT image 200, after which the radiation plan is computed using equation 6. In still other embodiments, not only the $CT_{avg}$ image 820 structures but also the PTV as defined in the $CT_{avg}$ image 820 is deformed to the BHCT image 200, after which the radiation plan is computed using equation 6. In still other embodiments, the $CT_{avg}$ image 820 is used rather than the BHCT image 200 to compute the radiation plan using equation 6. Since the airway segments 184 were segmented on the BHCT image 200, this embodiment involves performing a DIR from the BHCT 200 to the $CT_{avg}$ image 820 and applies DVFs of this registration to the airway segments 184. In still other embodiments, the CTavg image 820 is used along with a union of the airway segments 1 from the ten phase images of the 4DCT 330 to compute the radiation plan using equation 6.

Figure 9A:
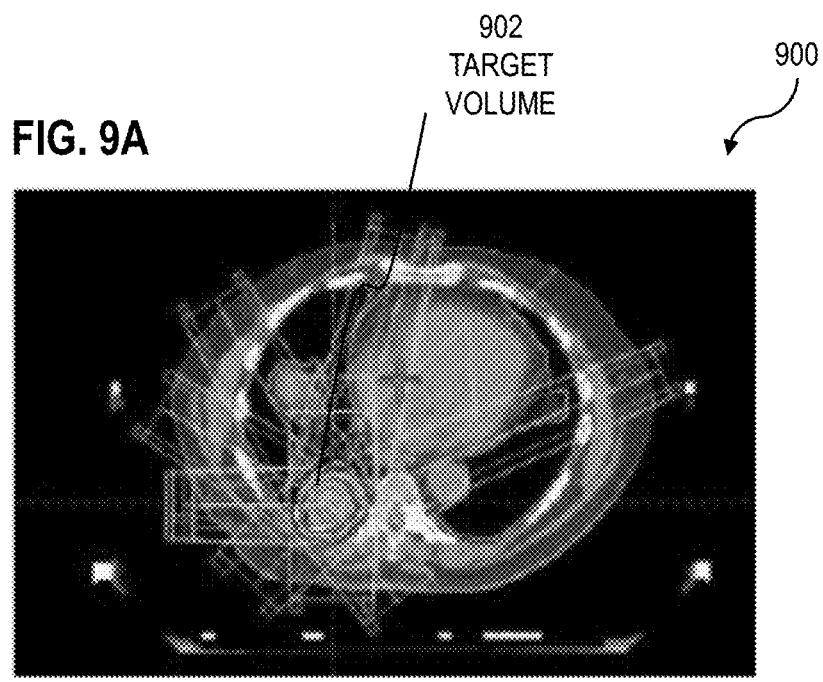
FIGS. 9A through 9C are images that illustrate an example of various views of the target volume and OAR volume within a subject that identifies example contour lines of radiation beams and dose levels, according to an embodiment.
Figures 9B, 9C:

FIGS. 9A through 9C are images 900, 920, 940 that illustrate an example of various views of the target volume 902 and OAR volume within a subject, according to an embodiment. FIG. 10A is an image that illustrates an example of a PTV 702 and OARs 720 within a subject, according to a conventional method. FIGS. 10B and 10C are images that illustrate an example of a PTV and OARs within a subject, according to an embodiment.

Figure 11A:
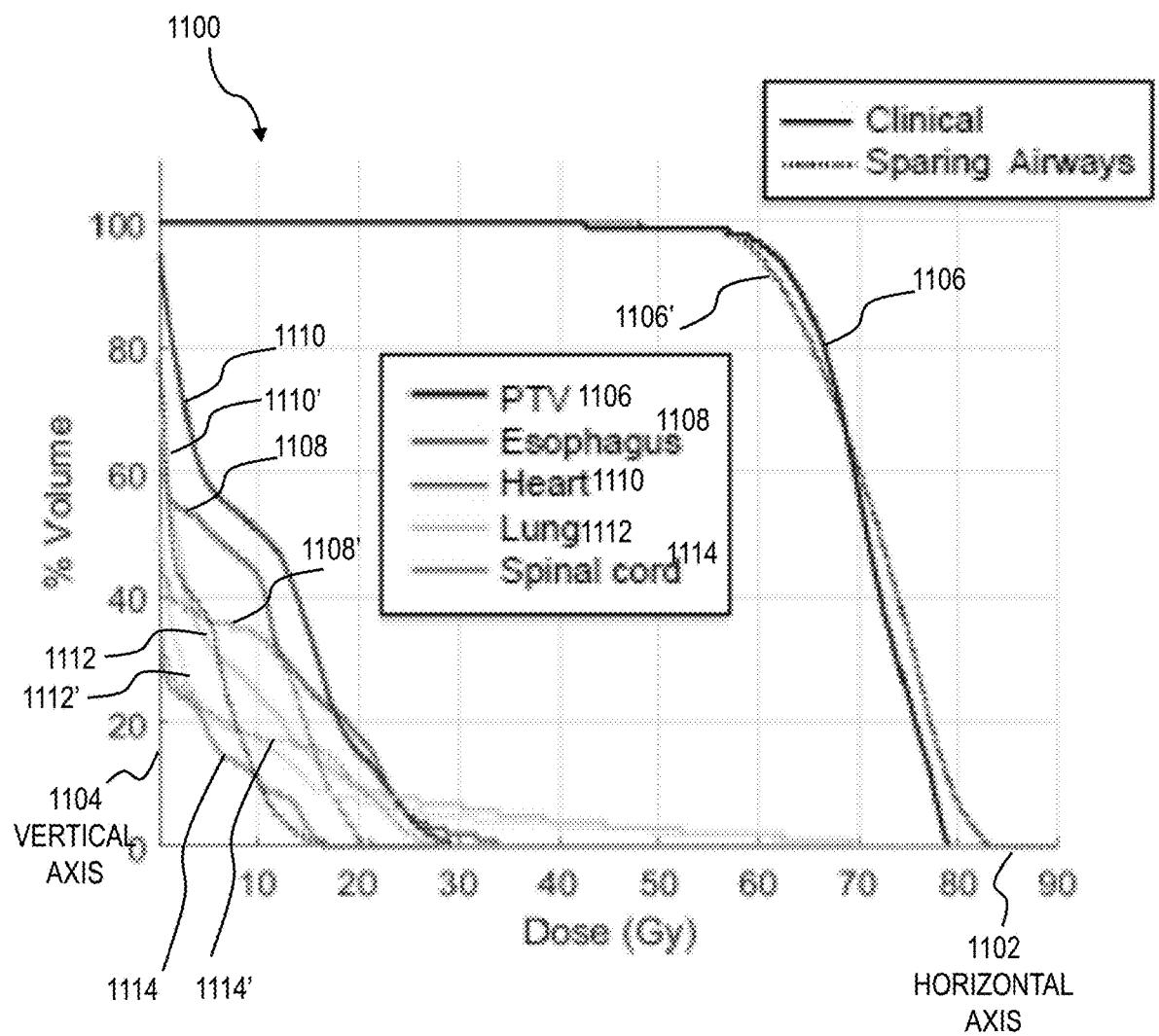
FIG. 11A illustrates an example of a dose-volume histogram (DVH) for PTV and typical OARs in the conventional clinical plan and the plan according to an embodiment for radiation therapy.

In an example embodiment, a dose-volume histogram (DVH) is provided which depicts the ratio of each tissue type that received different ranges of dosage levels. Additionally, the DVH conveniently permits comparison between a conventional plan and the RT plan from step 518, in terms of the dosage levels received by each tissue type. FIG. 11A illustrates an example of a cumulative DVH 1100 of the conventional clinical plan and the plan ("sparing airways" in FIG. 11A) according to an embodiment for radiation therapy. The horizontal axis 1102 is dosage in units of gray (Gy) and the vertical axis 1104 is volume as a percentage (%). As appreciated by one skilled in the art, an (x, y) value on the curves of FIG. 11A indicates a y volume percentage along the axis 1104 of the respective tissue type that receives a dosage equal to or larger than the x value along the axis 1102. In an embodiment, dotted lines indicate a DVH based on the radiation plan of the embodiments of the present invention (labeled as "Sparing Airways"), whereas solid lines indicate a DVH using a conventional clinical radiation plan (labeled as "Clinical"). Thus, curves 1106, 1106' indicate that the target coverage is approximately equal for the radiation plan of the present invention as compared to the conventional plan. Additionally, for each OAR other than the spinal cord, the radiation plan of the present invention resulted in less dosage received by each OAR. Specifically, curves 1112, 1112' indicate that the lung receives significantly less radiation under the radiation plan of the present invention relative to the conventional plan.

Figure 11B:
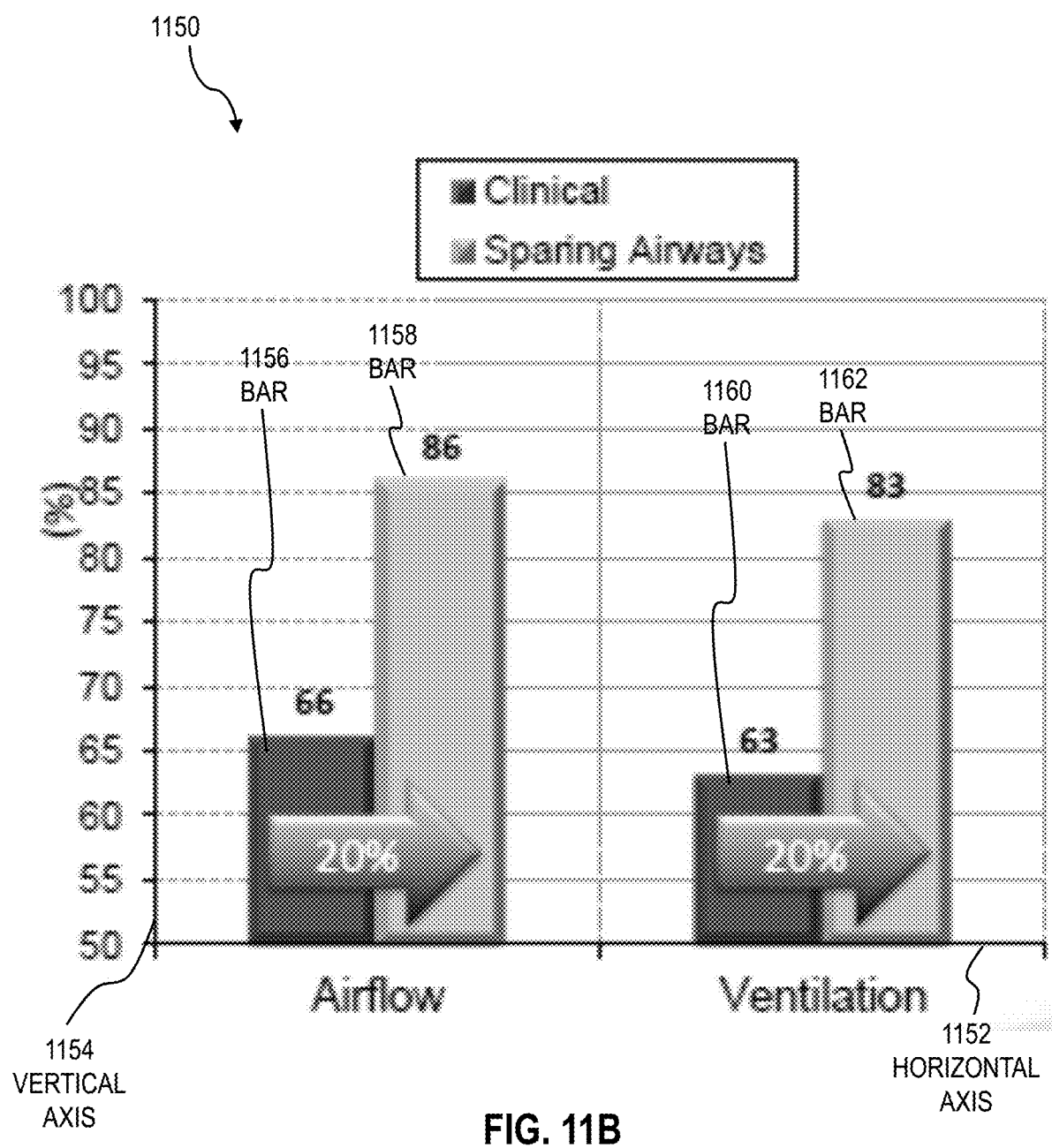
FIG. 11B is a bar chart that illustrates examples of percentages of airflow and ventilation preservation in the conventional clinical plan and plan according to an embodiment for radiation therapy.

In addition to DVHs, a bar chart is provided which further depicts a comparison between the conventional radiation plan and the RT plan from step 518. FIG. 11B is a bar chart 1150 that illustrates examples of percentages of airflow and ventilation preservation in the conventional clinical plan and plan ("sparing airways" in FIG. 11B) according to an embodiment for radiation therapy. For purposes of the bar chart 1150, "airflow" indicates a percentage of the flow of air through the airway paths from the trachea to the terminal airway segments 184 that is preserved by the radiation plan and "ventilation" indicates a percentage of the total ventilation of the volumes 189 (e.g. from equation 2) that are preserved by the radiation plan due to the airflow preservation. The horizontal axis 1152 indicates airflow or ventilation and the vertical axis 1154 is a ratio in percentage. Bars 1156, 1158 indicate the radiation plan according to the present invention preserves a greater ratio (86%) of airflow through the terminal airway segments 184, relative to the conventional plan (66%). Bars 1160, 1162 further indicate the radiation plan according to the present invention preserves a greater ratio (83%) of ventilation at the dependent volumes 189, relative to the conventional plan (63%).

Four subjects (P1, P2, P3, P4 hereafter) were used to assess the performance of the radiation plan according to the present invention relative to the conventional radiation plan. Data regarding the four patients is presented in Table 1 below.

TABLE 1

| P1 | P2 | P3 | P4 |
|---|---|---|---|
| 59-year-old woman | 55-year-old woman | 75-year-old man | 62-year-old man |
| PTV: 112.53 cc | PTV: 11.98 cc | PTV: 96.76 cc | PTV: 19.85 cc |
| (LUL, central, anterior) | (LLL, posterior) | (between RUL and RML, posterior) | (RUL, centre) |
| Prescription: 10 Gy × 5 fractions (11-beam CRT) | This patient has no LUL (surgically removed) | Prescription: 12 Gy × 5 fractions (13-beam CRT) | PTV: 7.76 cc (RLL, posterior) |
| Seg airways: 251 | Prescription: 12 Gy × 5 fractions (CRT) | Seg airways: 239 | Prescription: 18 Gy × 3 fractions (10-beam CRT) for each PTV |
| Seg terminal airways: 127 | Seg airways: 166 | Seg terminal airways: 119 | Seg airways: 203 |
| Seg max generation: 12 | Seg terminal airways: 841 | Seg max generation: 102 | Seg terminal airways: 12 |
| | Seg max generation: 11 | | Seg max generation: 12 |

Where "seg airways" indicates the total number of airway segments 205; "seg terminal airways" indicates the total number of terminal airway segments 205 (e.g. airway segment 184f in FIG. 1F) and "seg max generation" indicates the maximum number of airway levels (generations) between trachea 184a and terminal airways 184f.

In some embodiments, DVHs are generated for each tissue type in each subject in order to compare the conventional radiation plan with the RT plan determined in step 518. FIGS. 12A through 12E are graphs that illustrate example DVHs for PTV and OARs (e.g. heart, lung, spinal cord and esophagus) of the conventional plan and the plan according to an embodiment. In an embodiment, the DVH of FIGS. 12A through 12E are based on a subject (P3) who received a radiation treatment plan according to the present invention. The horizontal axis 1202 is dosage in units of gray (Gy). The vertical axis 1204 is ratio in a percentage. In an embodiment, the curves 1206a, 1208a of FIG. 12A indicate a DVH for the PTV and indicate that the radiation plan according to the present invention and the conventional radiation provided about the same level of coverage of the target volume. In an embodiment, the curves 1206b, 1208b of FIG. 12B indicate a DVH for the heart tissue and indicate that the radiation plan according to the present invention (represented by curve 1208b) delivers less dosage to the heart tissue than the conventional radiation plan (represented by curve 1206b).

Figure 12A:
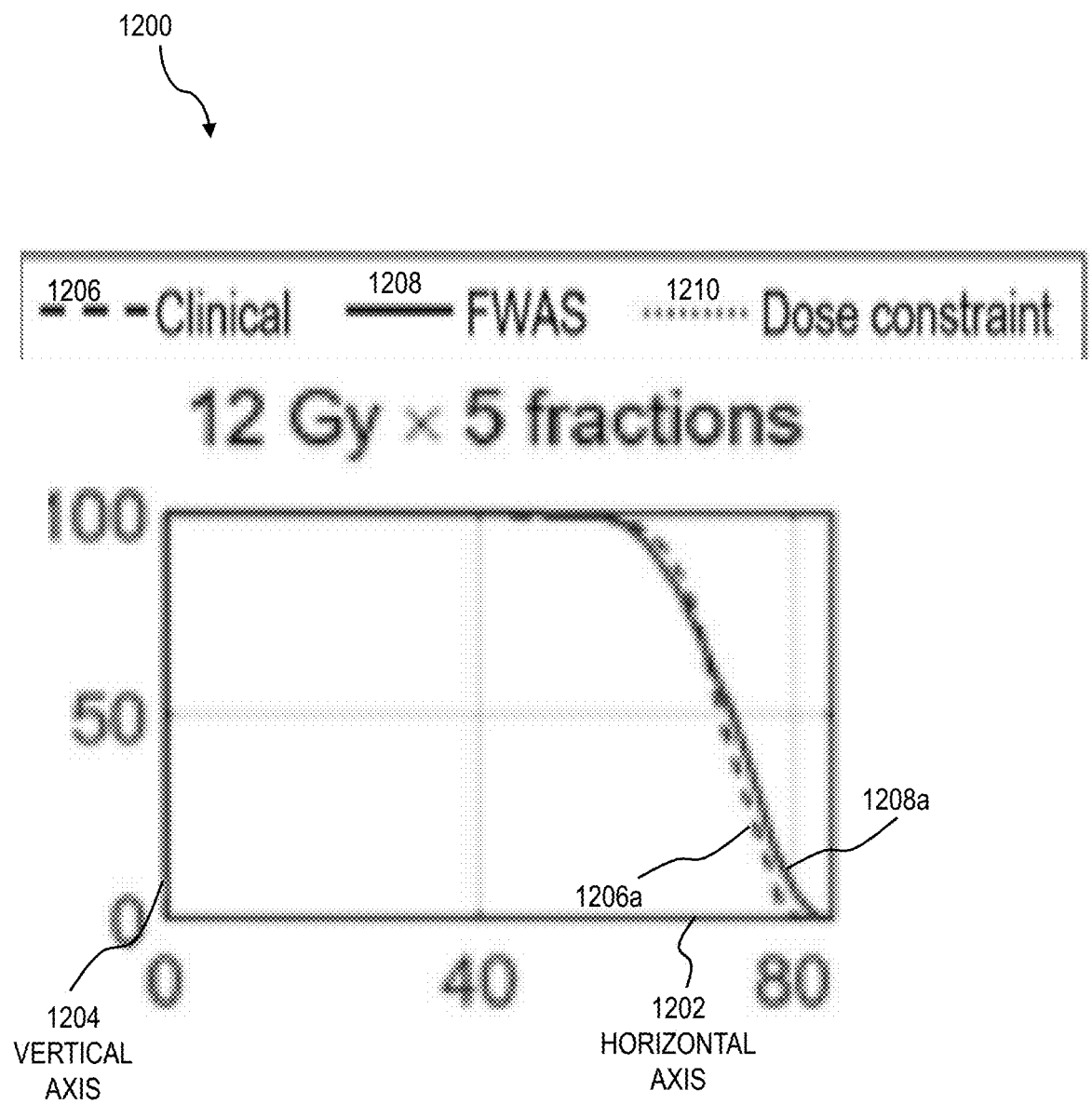
FIGS. 12A through 12E are graphs that illustrate example DVHs for PTV and OARs of the conventional clinical plan and the plan according to an embodiment.
Figure 12B:
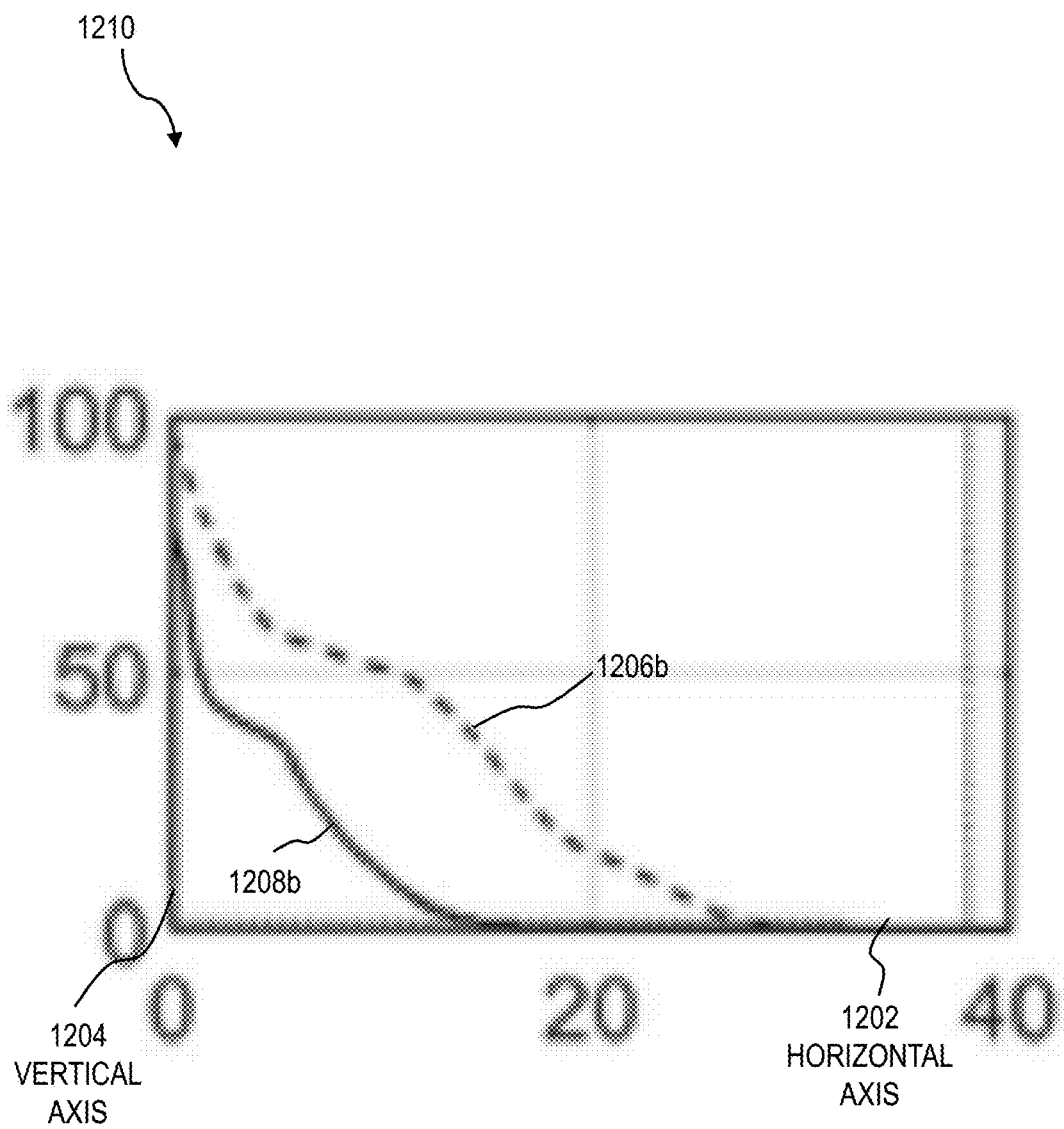
Figure 12C:
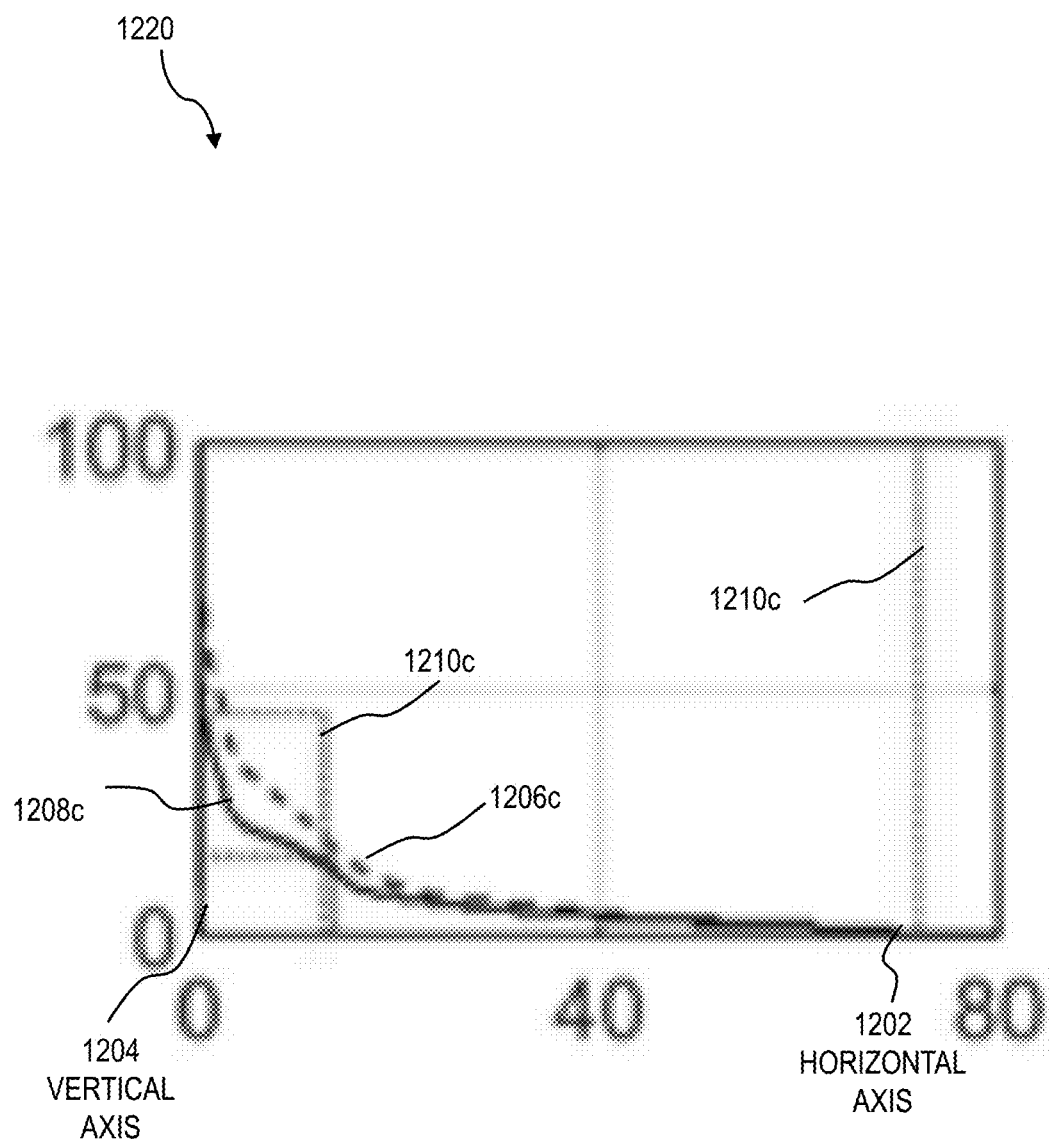
Figure 12D:
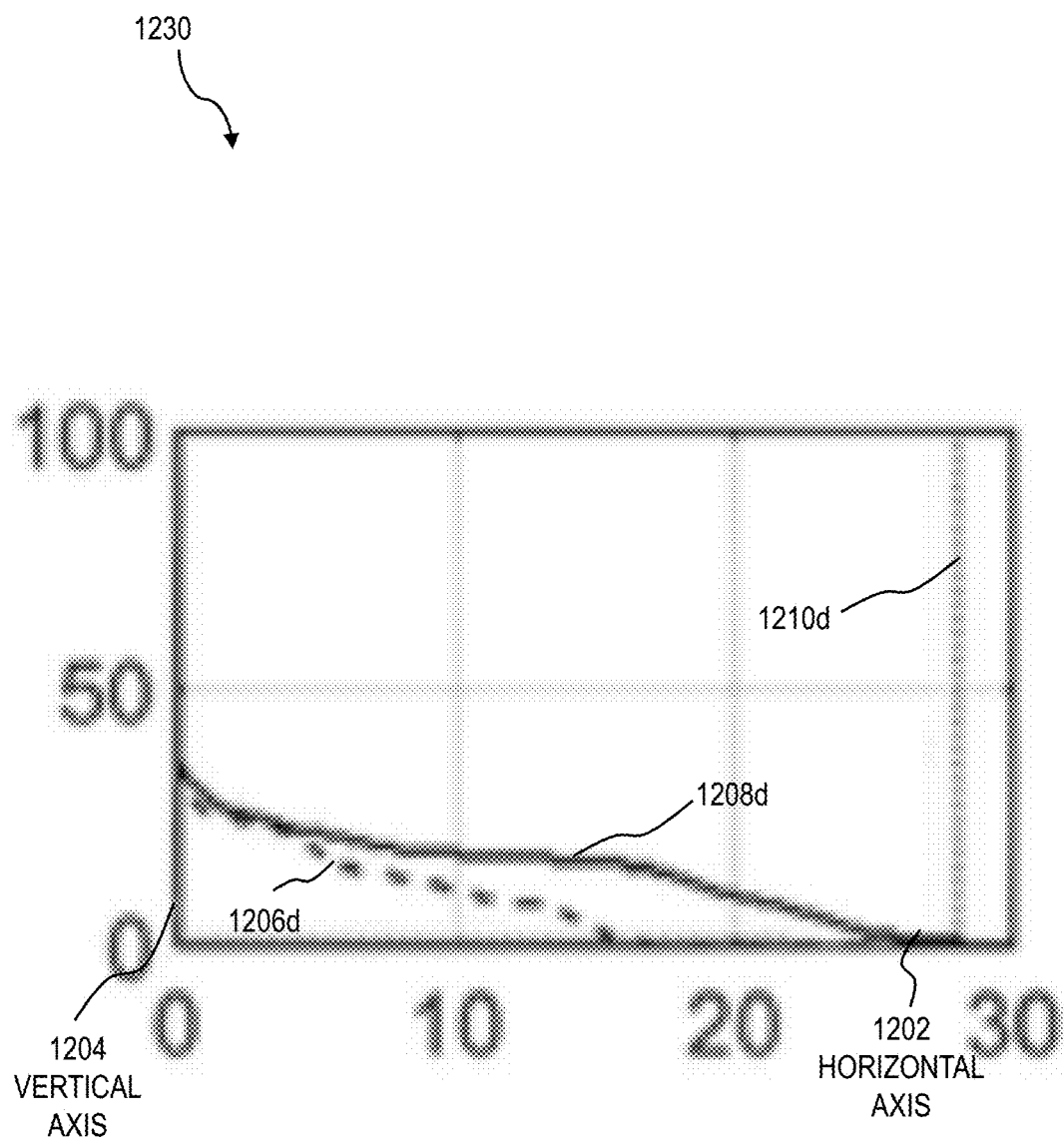
Figure 12E:
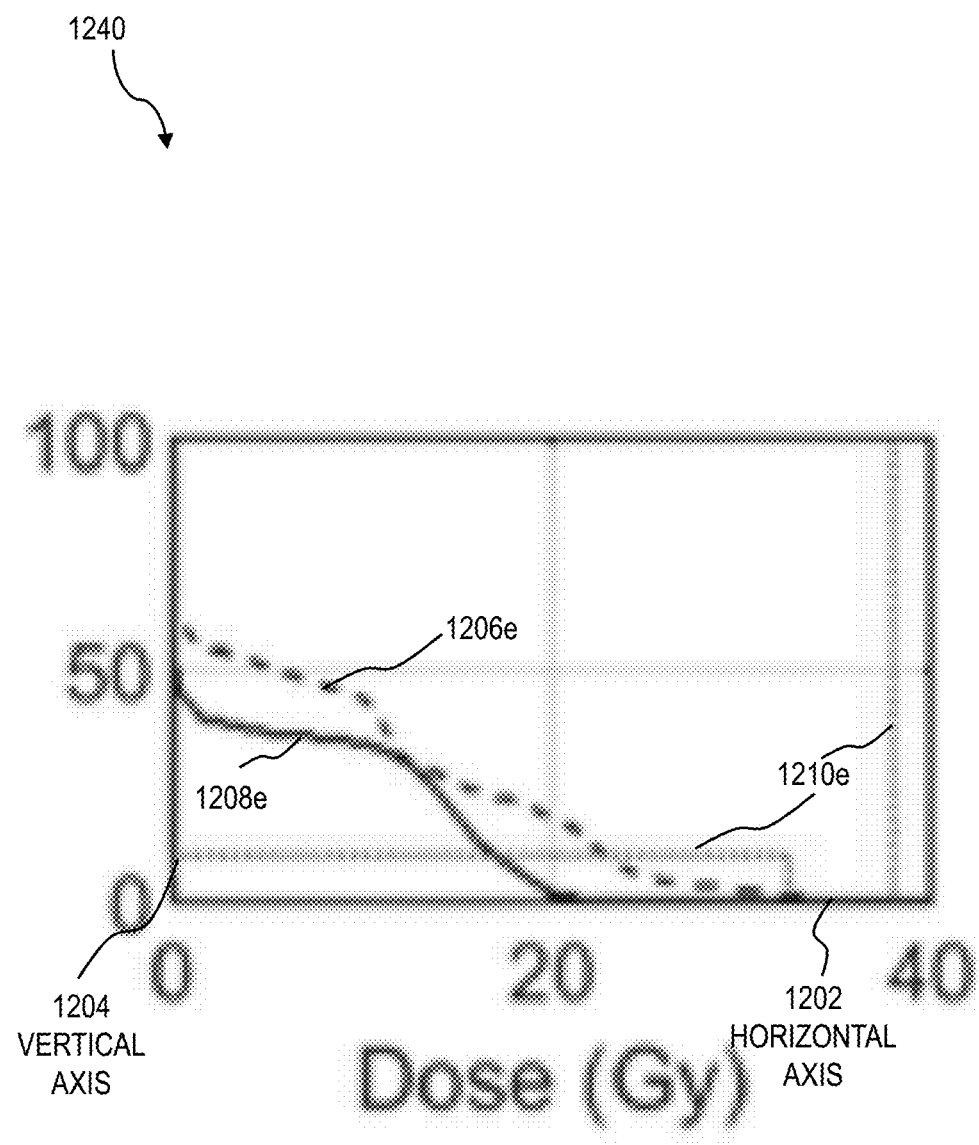

In an embodiment, for P3 (see Table 1 above), the curves 1206c, 1208c of FIG. 12C indicate a DVH for the lung tissue and indicate that the radiation plan according to the present invention (represented by curve 1208c) delivers less dosage to the lung tissue than the conventional radiation plan (represented by curve 1206c). In an embodiment, the curves 1206d, 1208d of FIG. 12D indicate a DVH for the spinal cord tissue and indicate that the radiation plan according to the present invention (represented by curve 1208d) delivers about the same dosage level to the spinal cord tissue as the conventional radiation plan (represented by curve 1206d). In an embodiment, the curves 1206e, 1208e of FIG. 12E indicate a DVH for the esophagus tissue and indicate that the radiation plan according to the present invention (represented by curve 1208e) delivers about the same dosage level to the esophagus tissue as the conventional radiation plan (represented by curve 1206e).

Figure 13A:
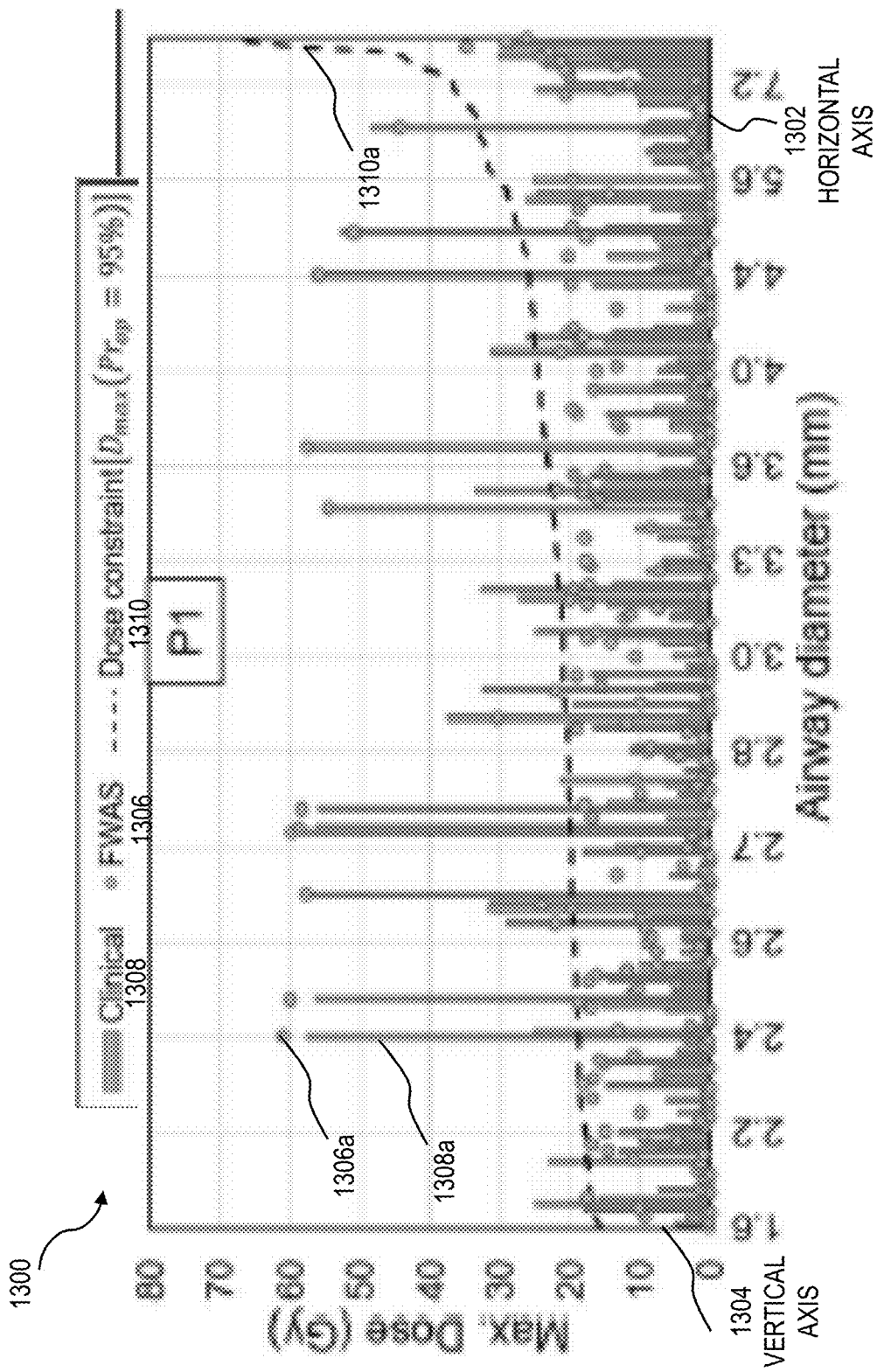
FIGS. 13A through 13D are graphs that illustrate an example of a maximum dose based on airway segment diameter for different subjects using the conventional plan and the plan according to an embodiment.
Figure 13B:
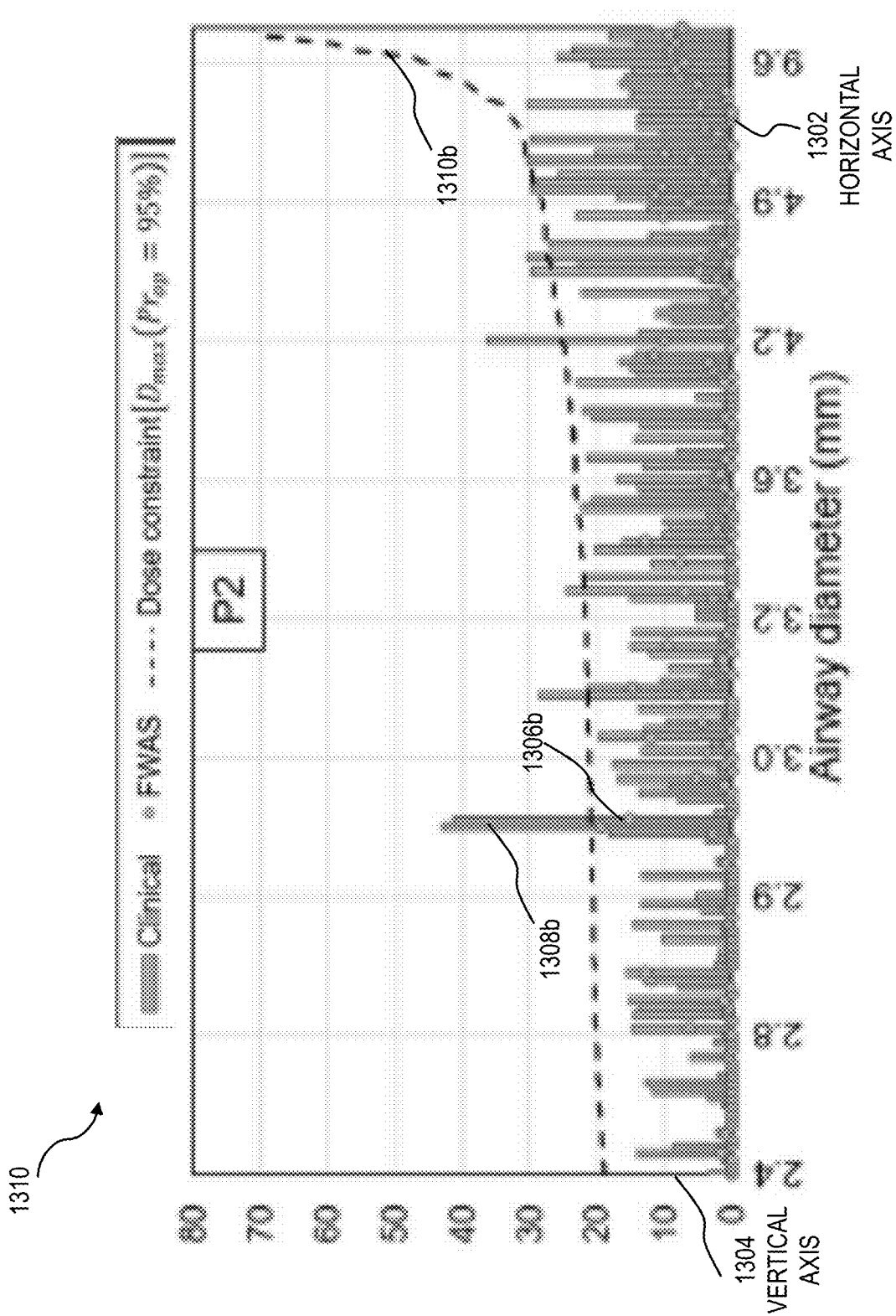
Figure 13C:
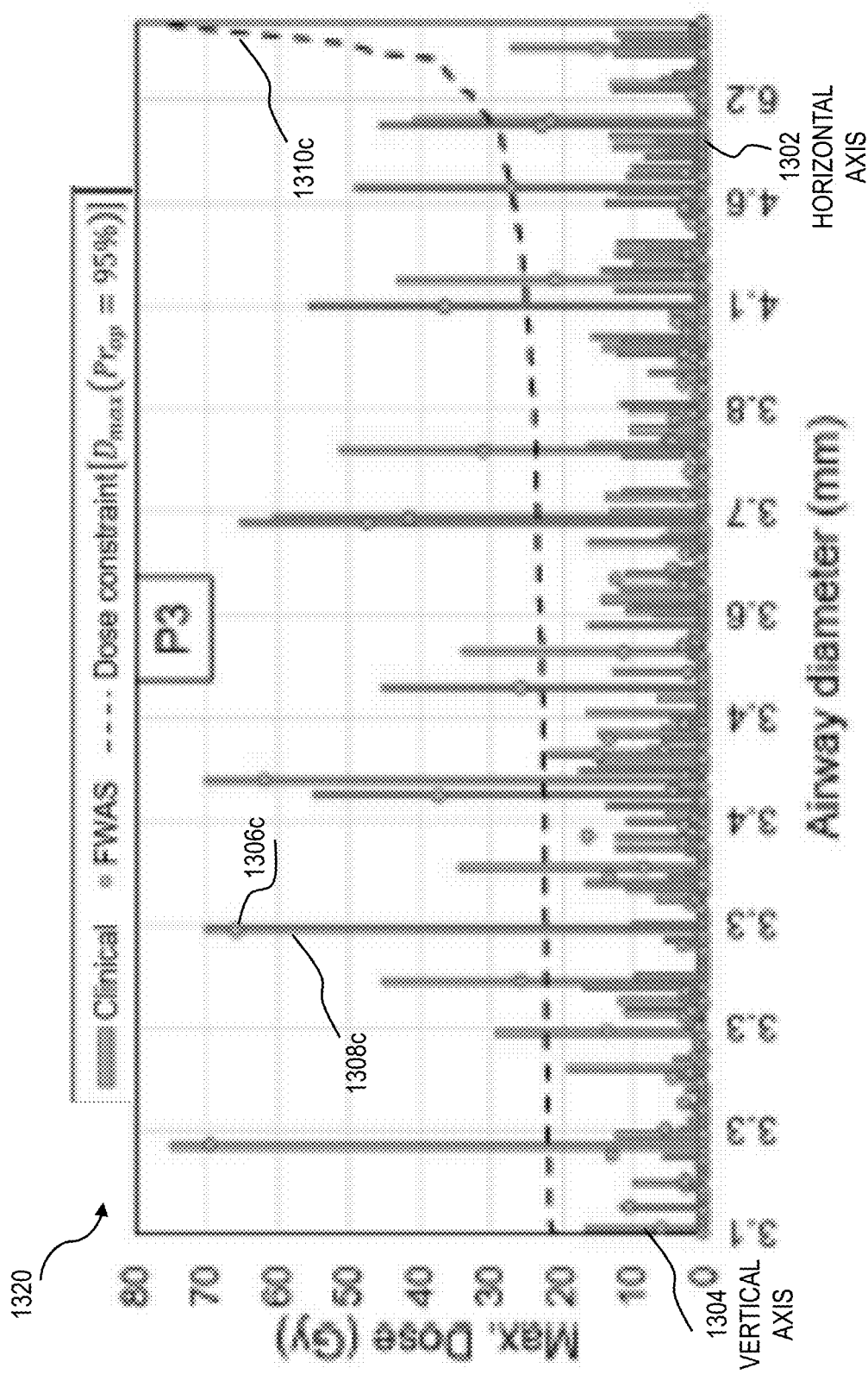
Figure 13D:
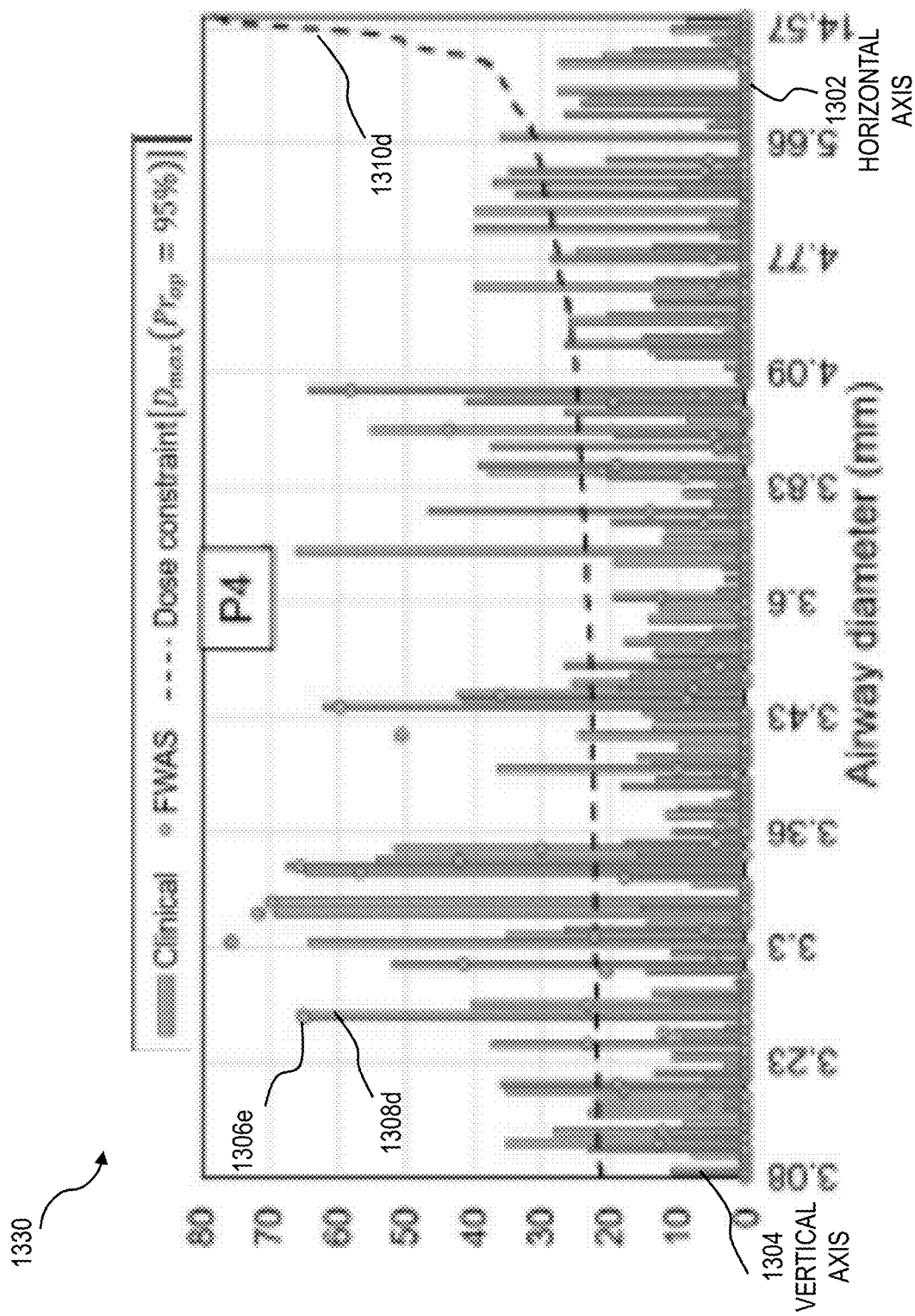
Figure 14A:
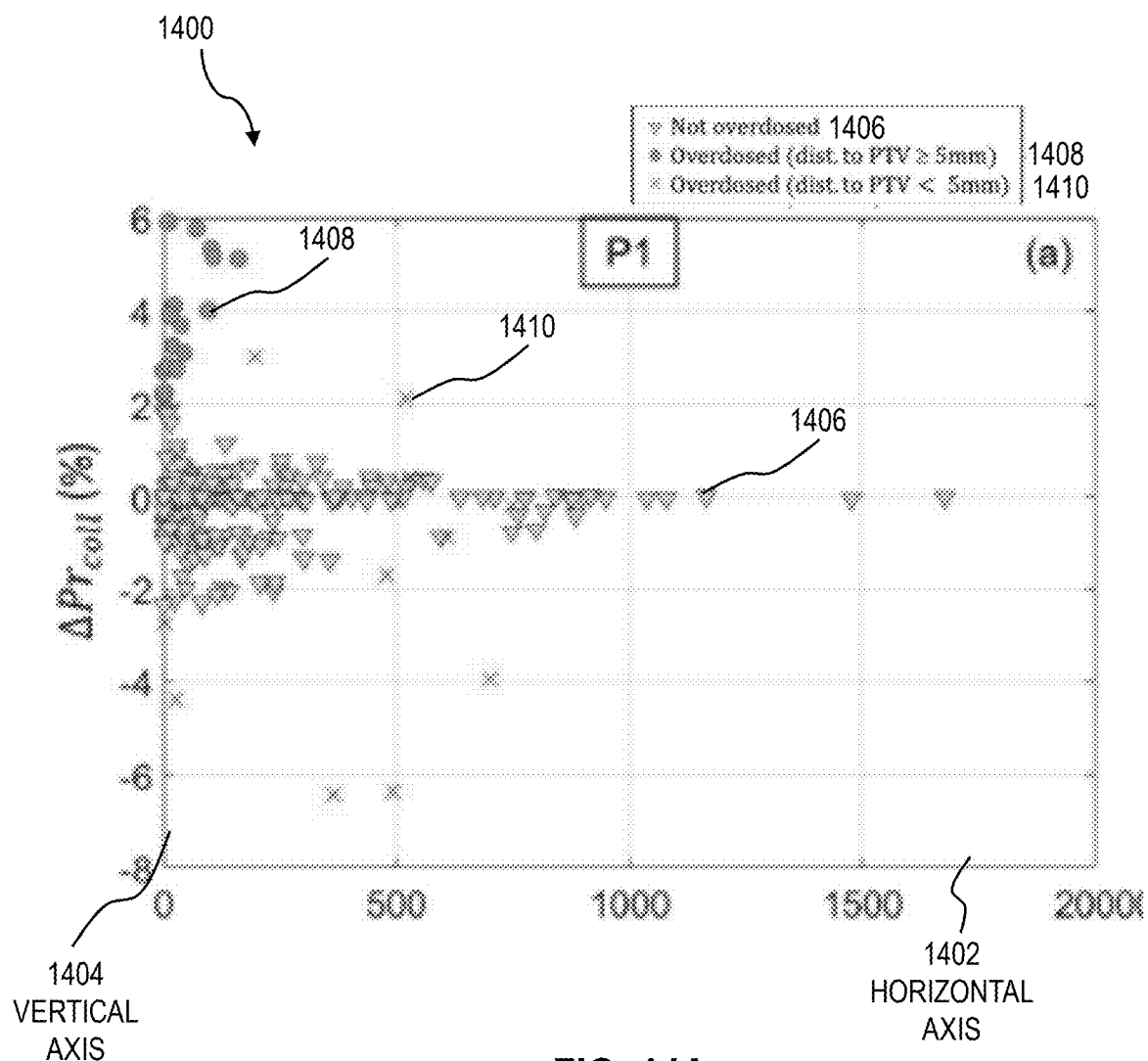
FIGS. 14A through 14E are graphs that illustrate an example of a reduction in airway collapse probability for different subjects using the conventional plan and the plan according to an embodiment.
Figure 14B:
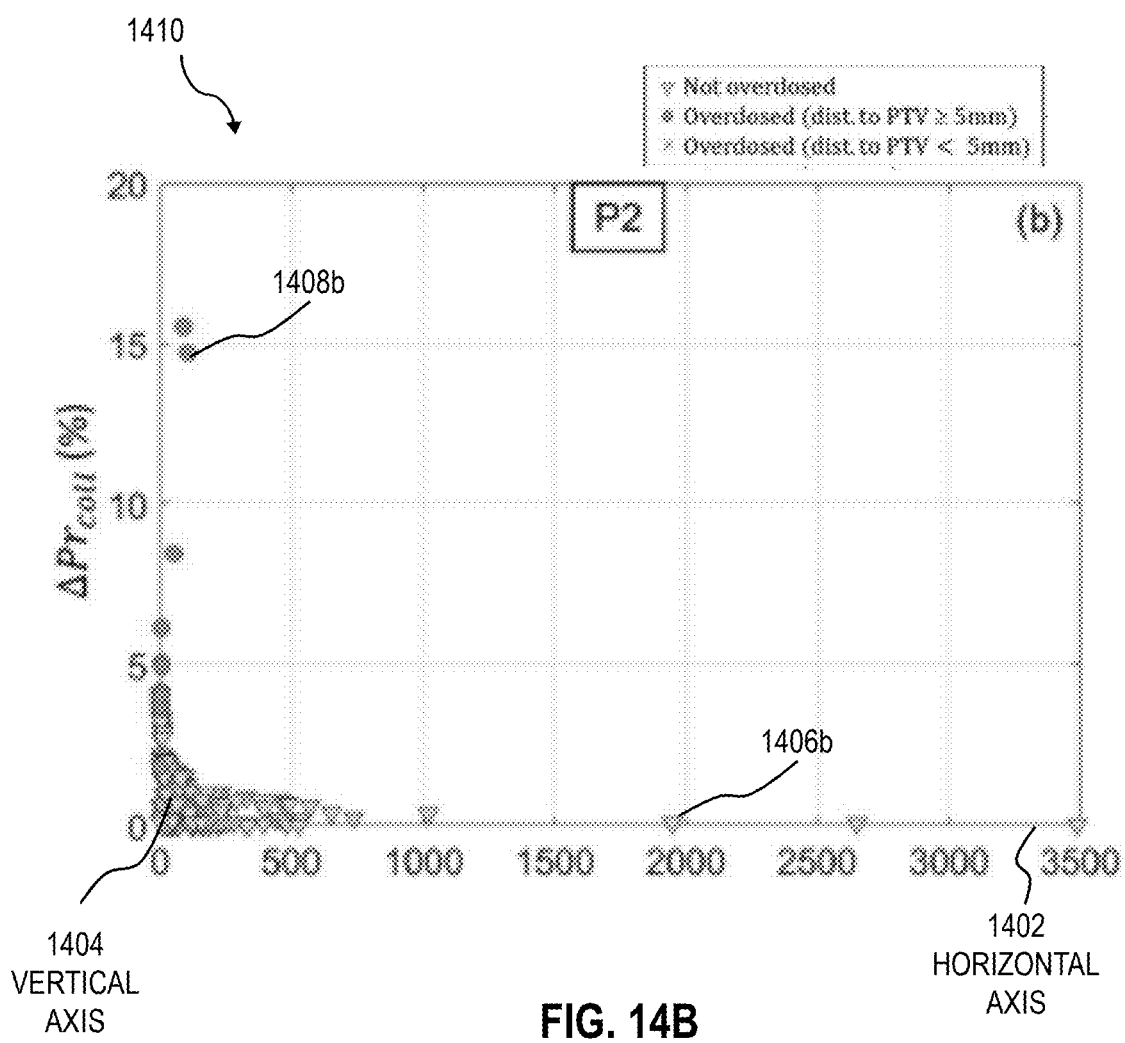
Figure 14C:
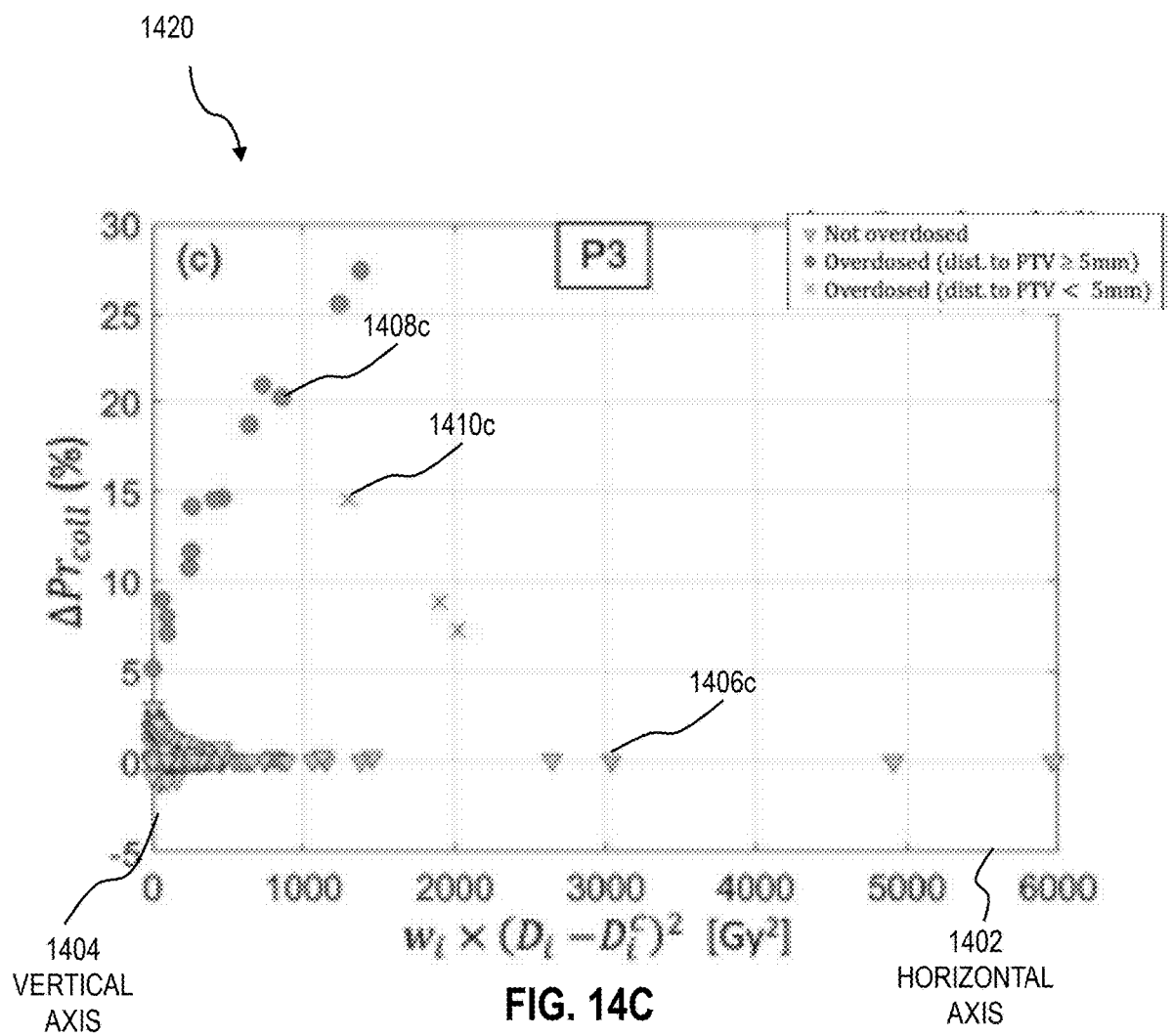
Figure 14D:
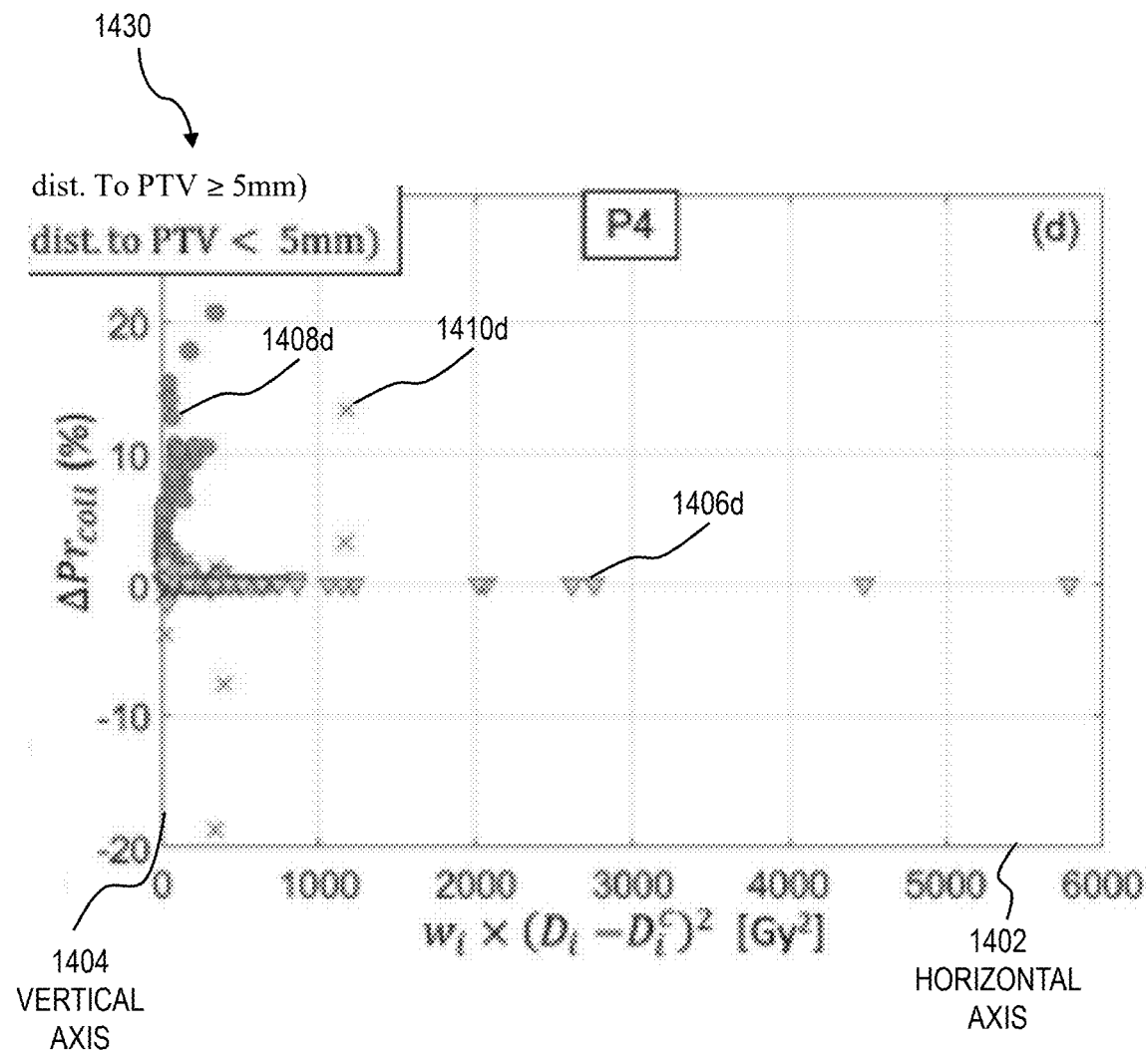
Figure 14E:
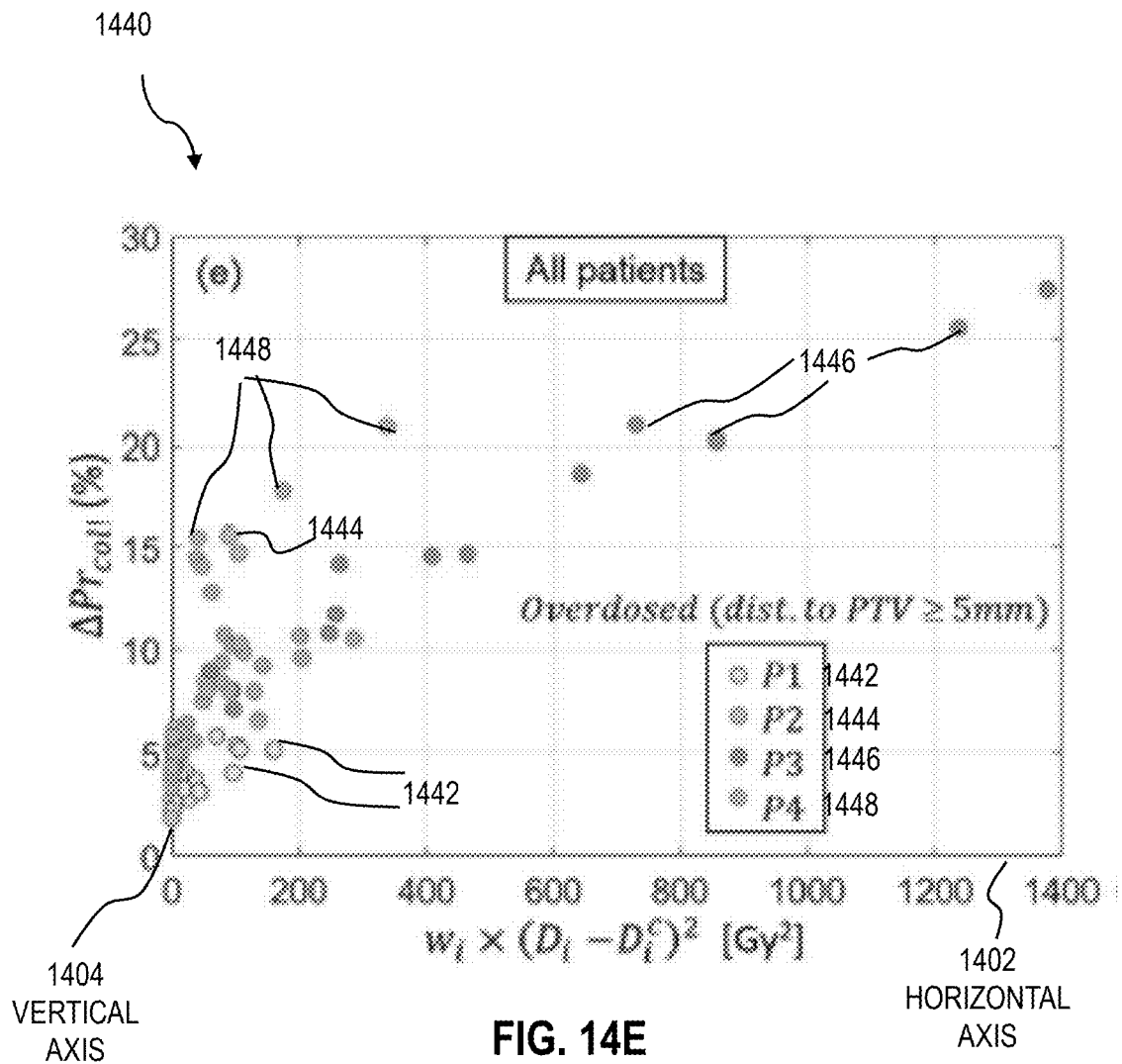
Figure 15A:
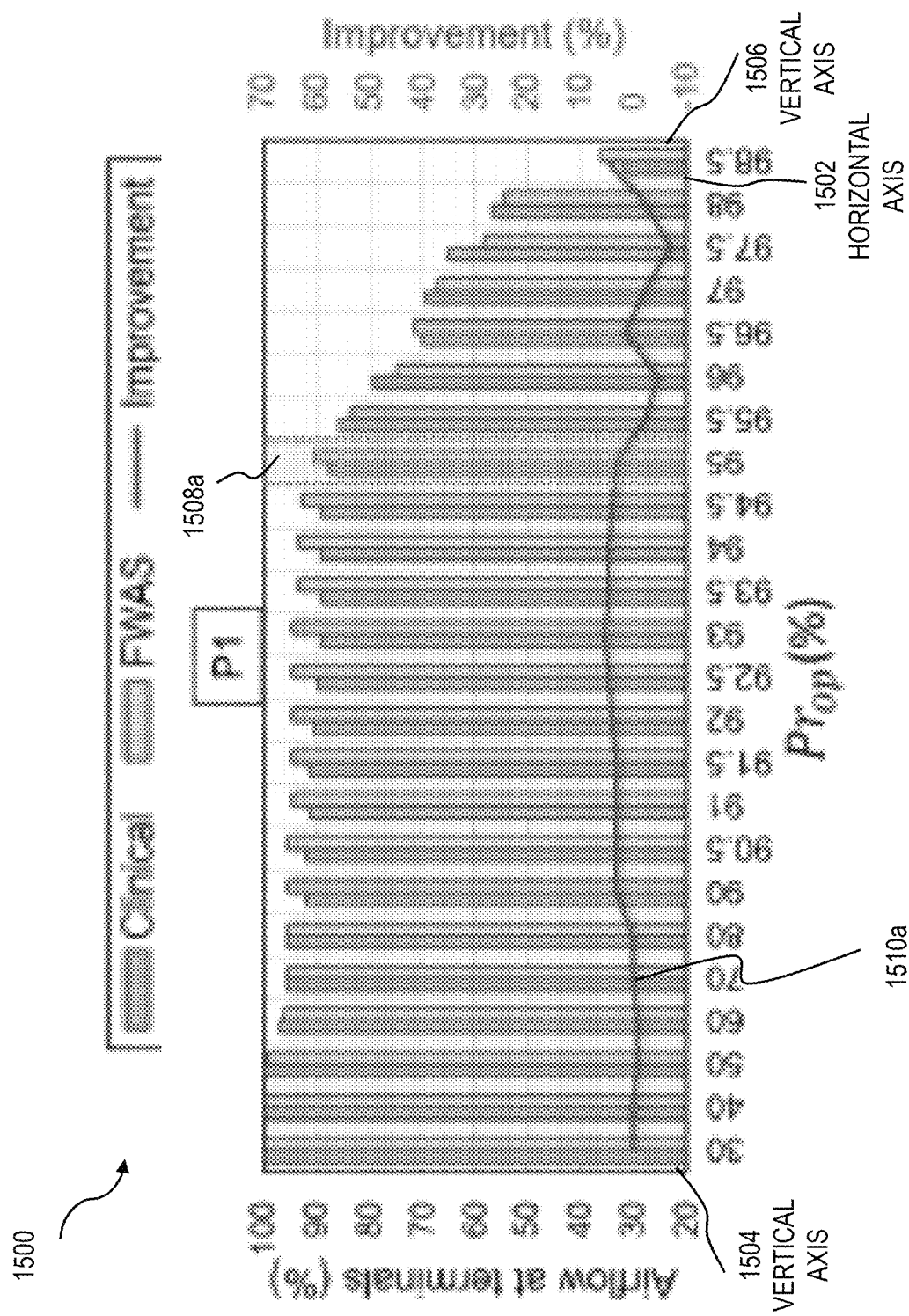
FIGS. 15A through 15D are graphs that illustrate an example of a preservation of airflow at terminal airway segments estimated for several probability levels of no airway collapse for different subjects using the conventional plan and the plan according to an embodiment.
Figure 15B:
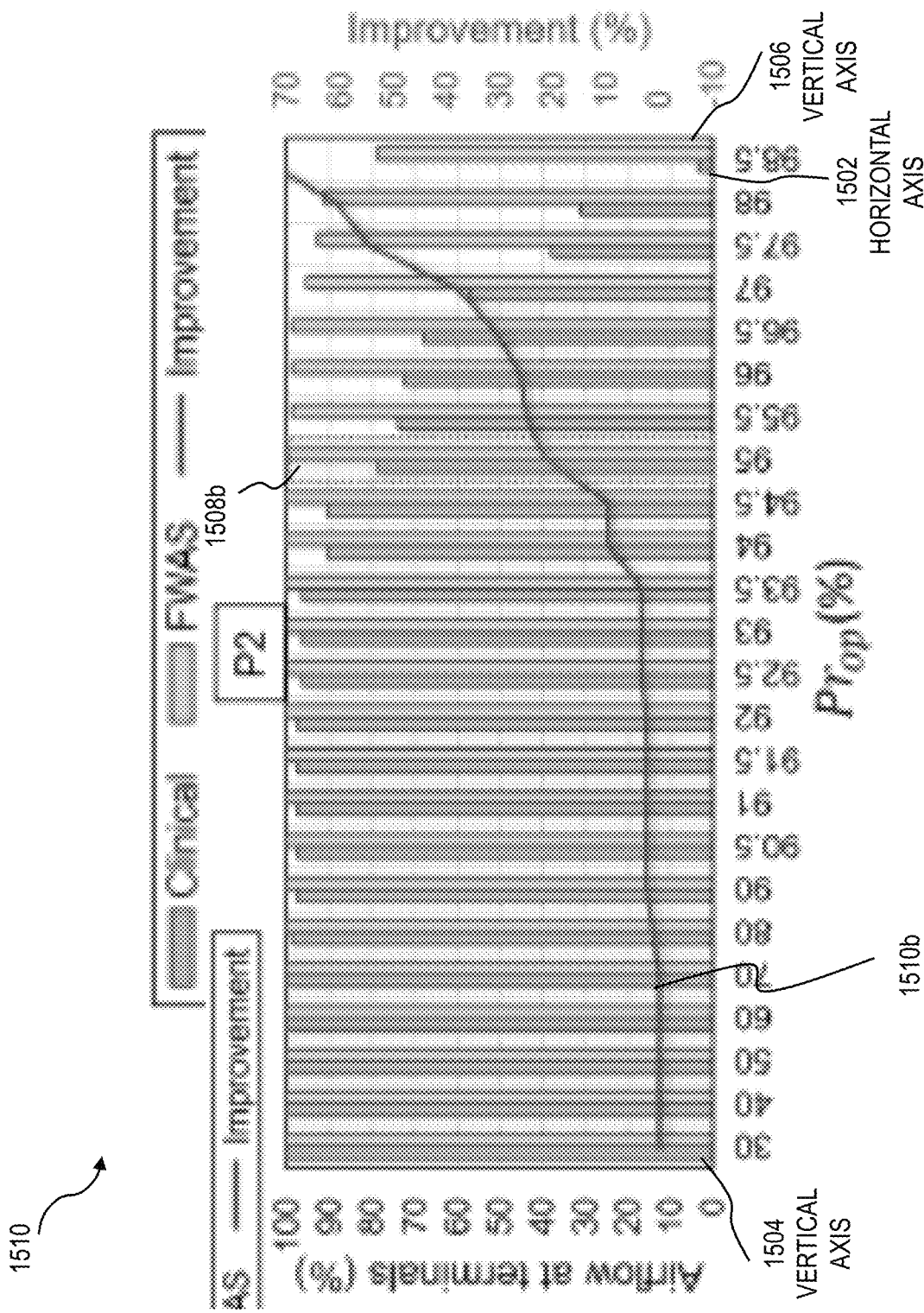
Figure 15C:
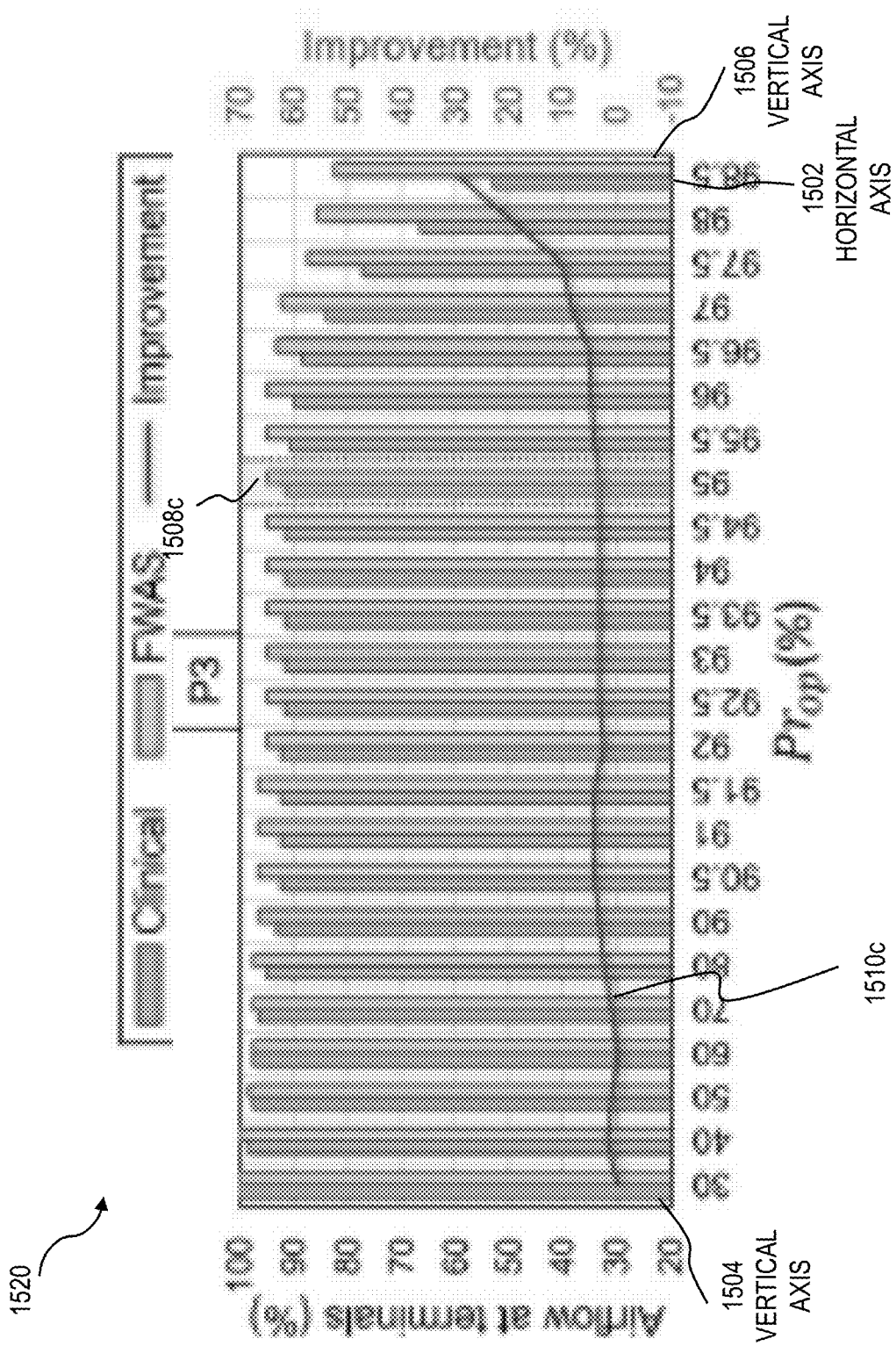
Figure 15D:
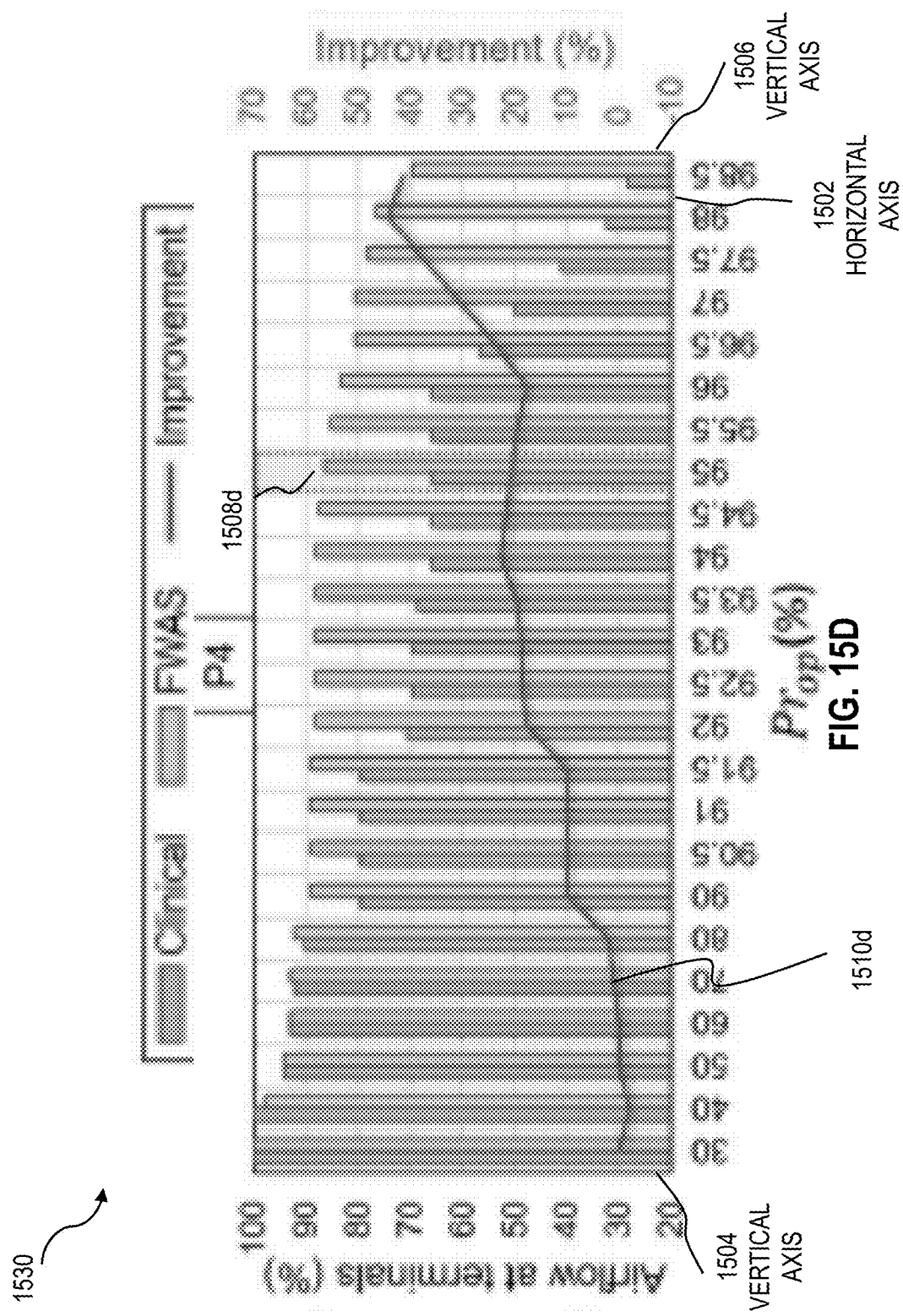
Figure 15E:
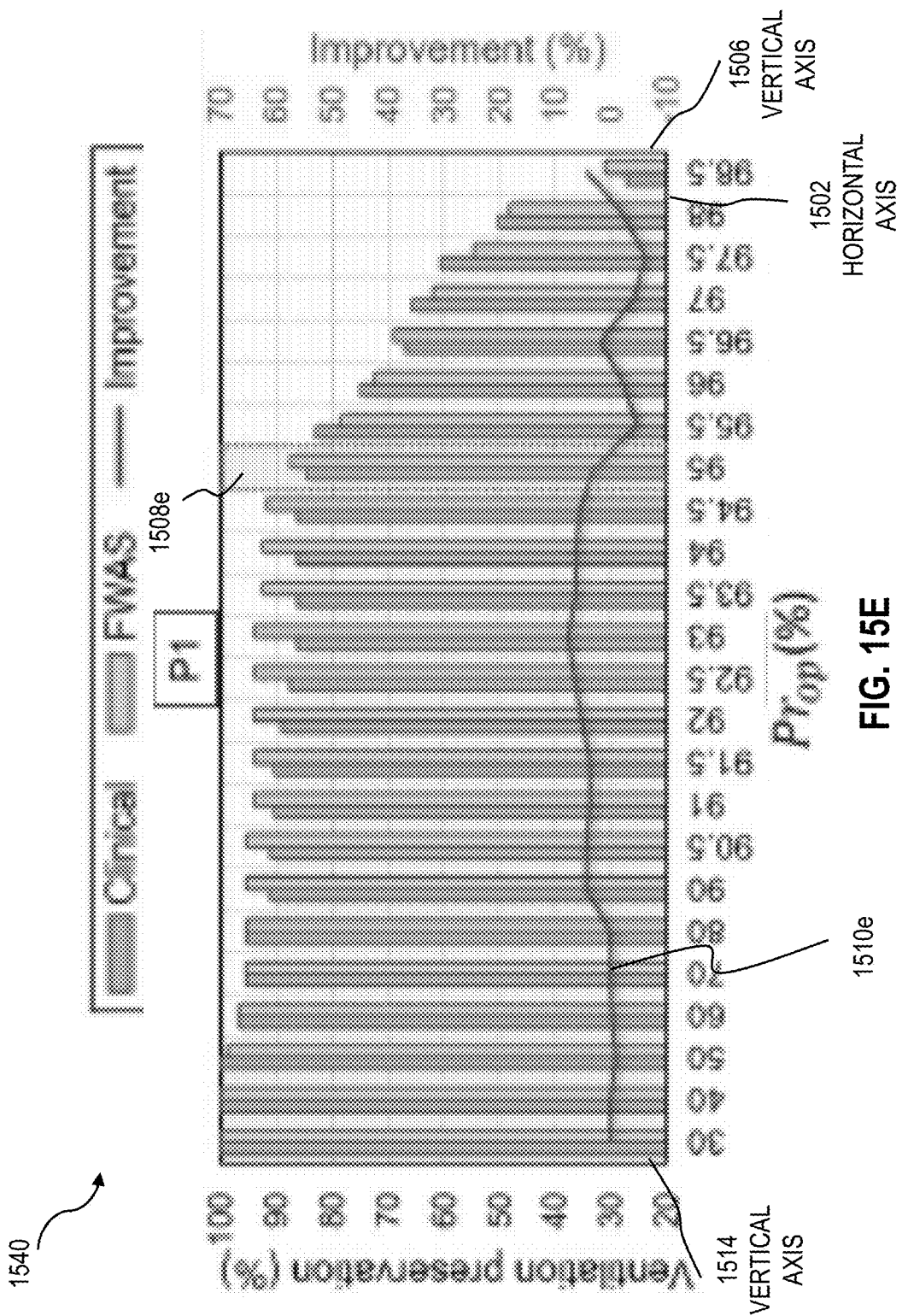
FIGS. 15E through 15H are graphs that illustrate an example of a preservation of ventilation estimated for several probability levels of no airway collapse for different subjects using the conventional plan and the plan according to an embodiment.
Figure 15F:
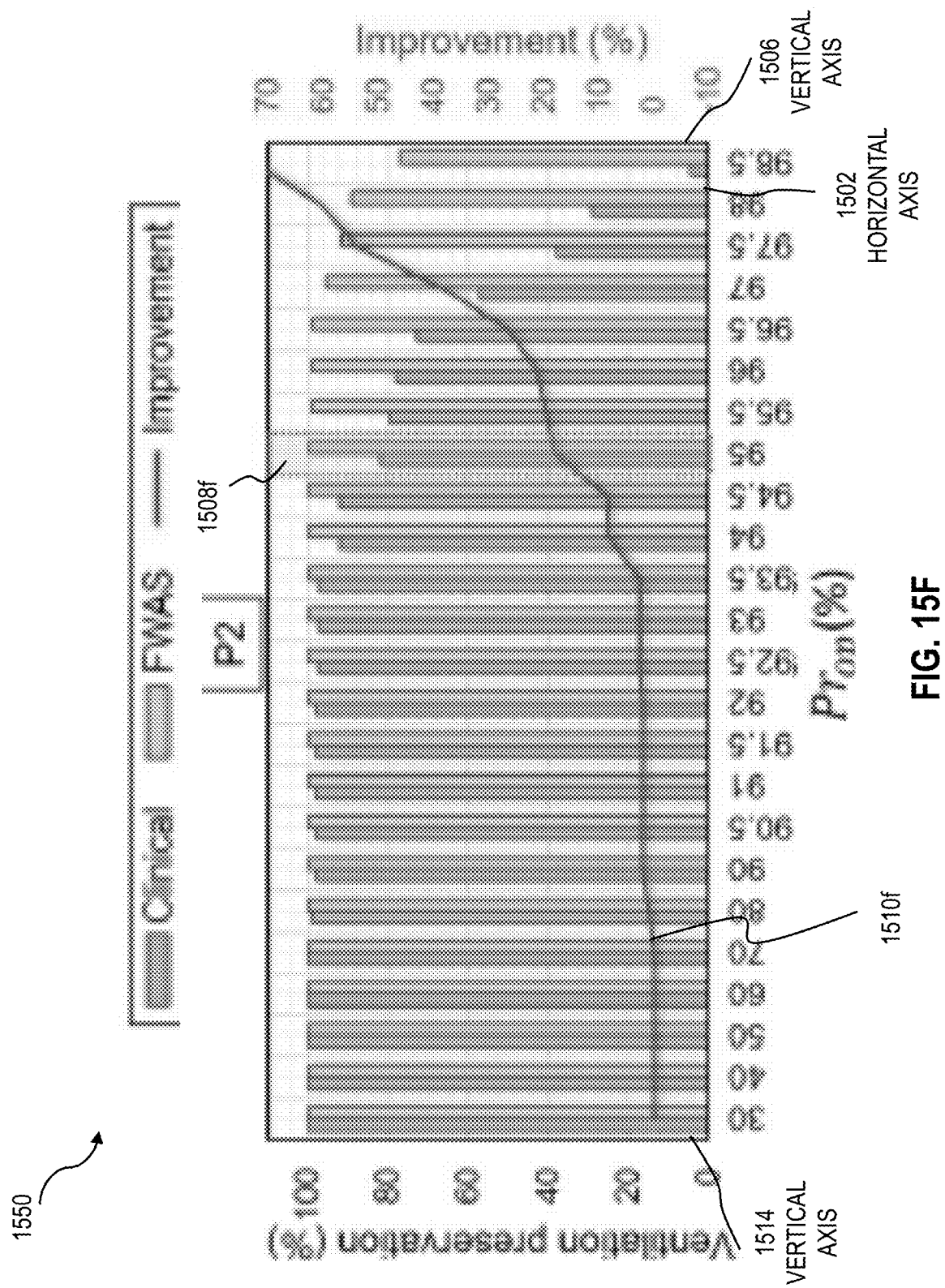
Figure 15G:
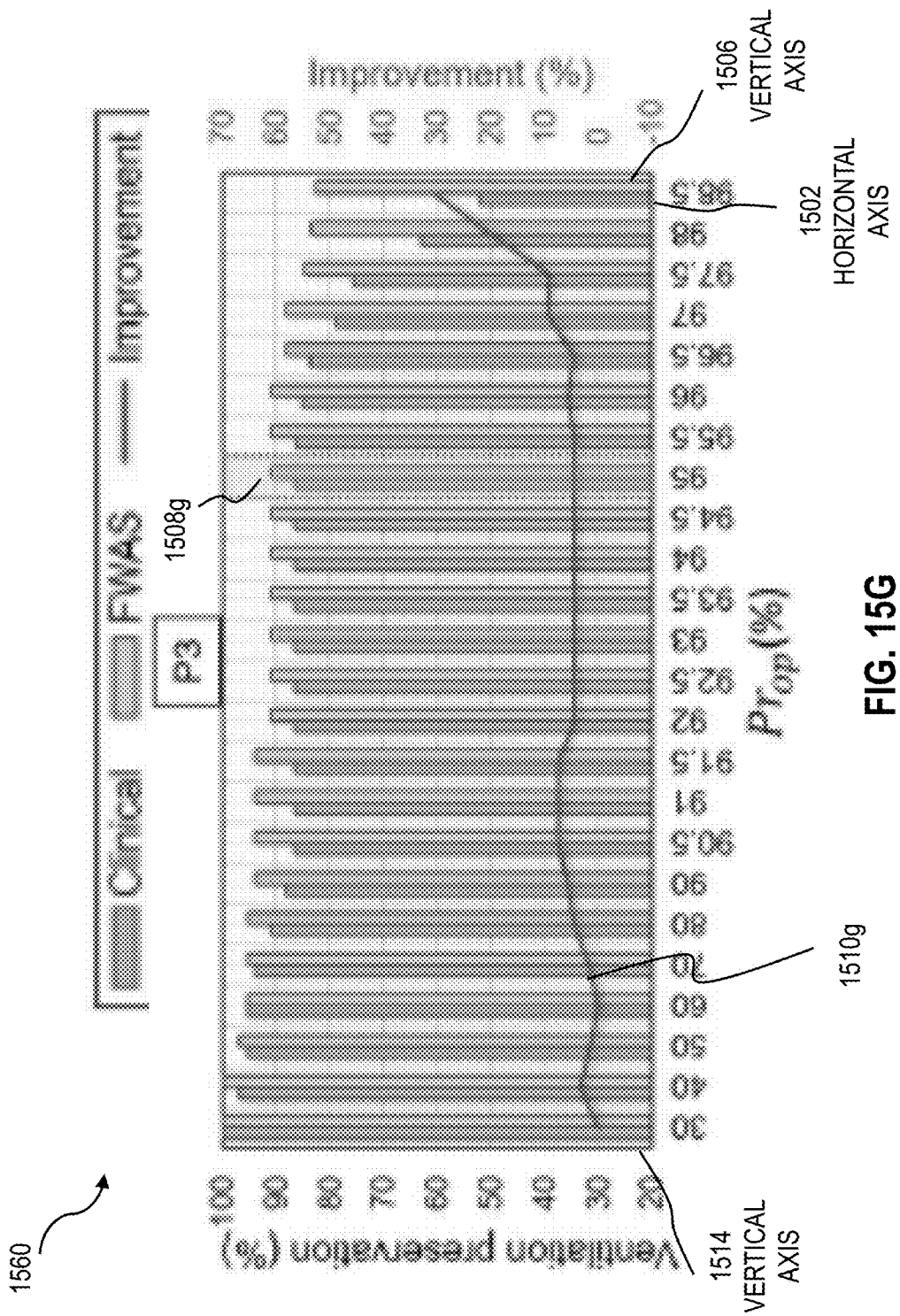
Figure 15H:
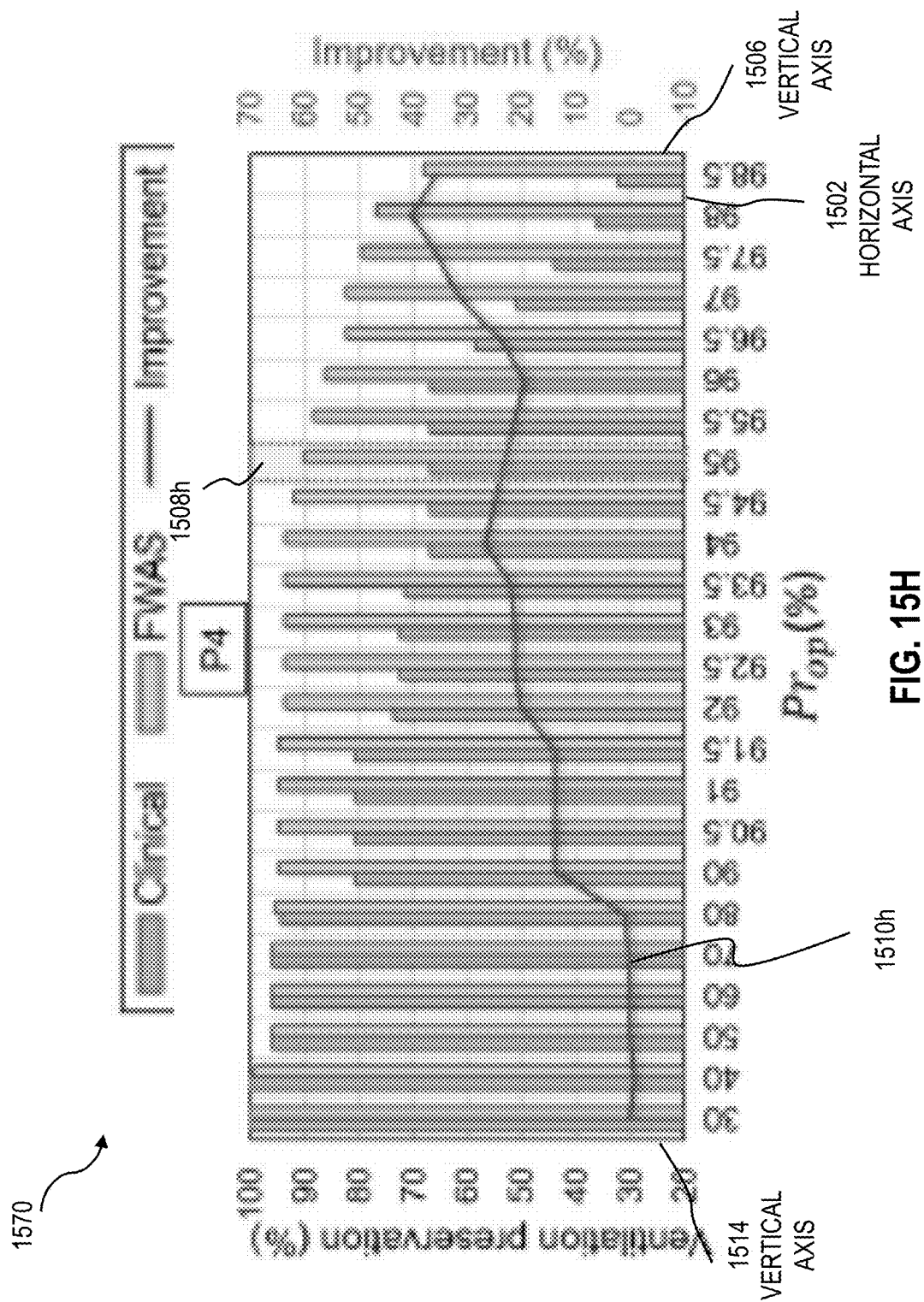
Figures 16A, 16B:
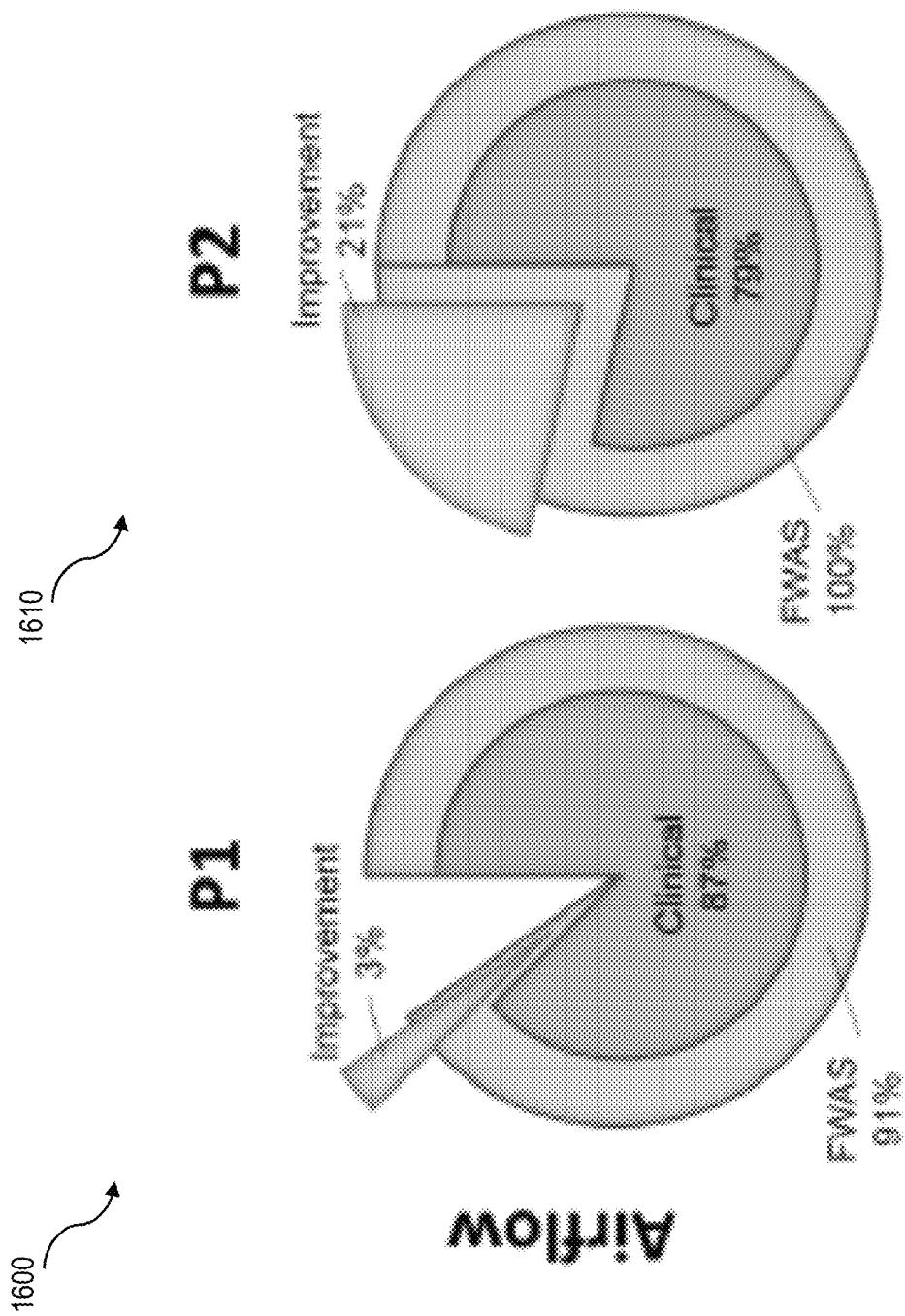
FIGS. 16A through 16D are pie charts that illustrate an example of the preservation of airflow at terminal airway segments for a probability of no airway collapse of 95% for different subjects based on FIGS. 15A through 15D, according to embodiments.
Figures 16C, 16D:
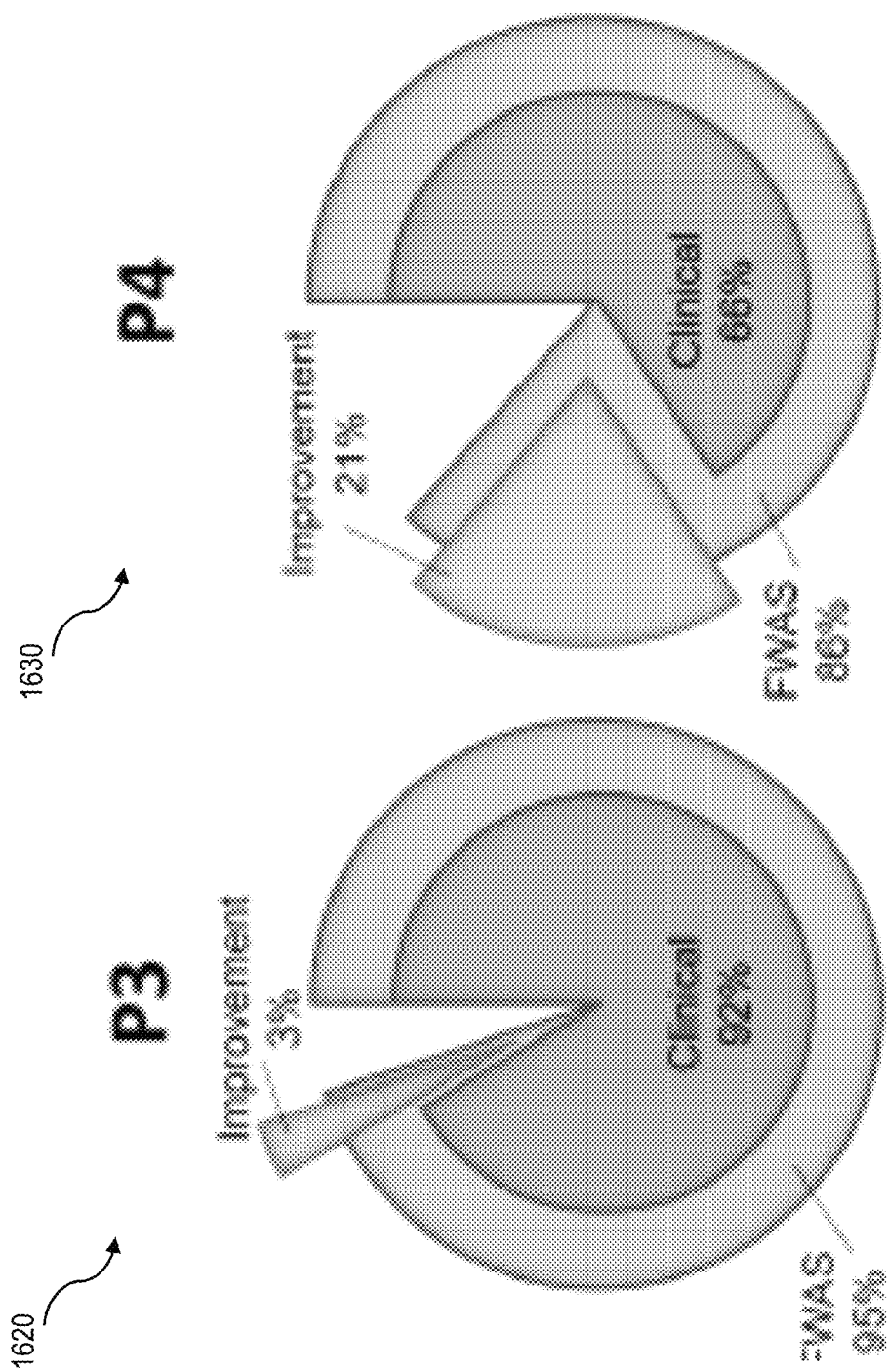
Figures 16G, 16H:
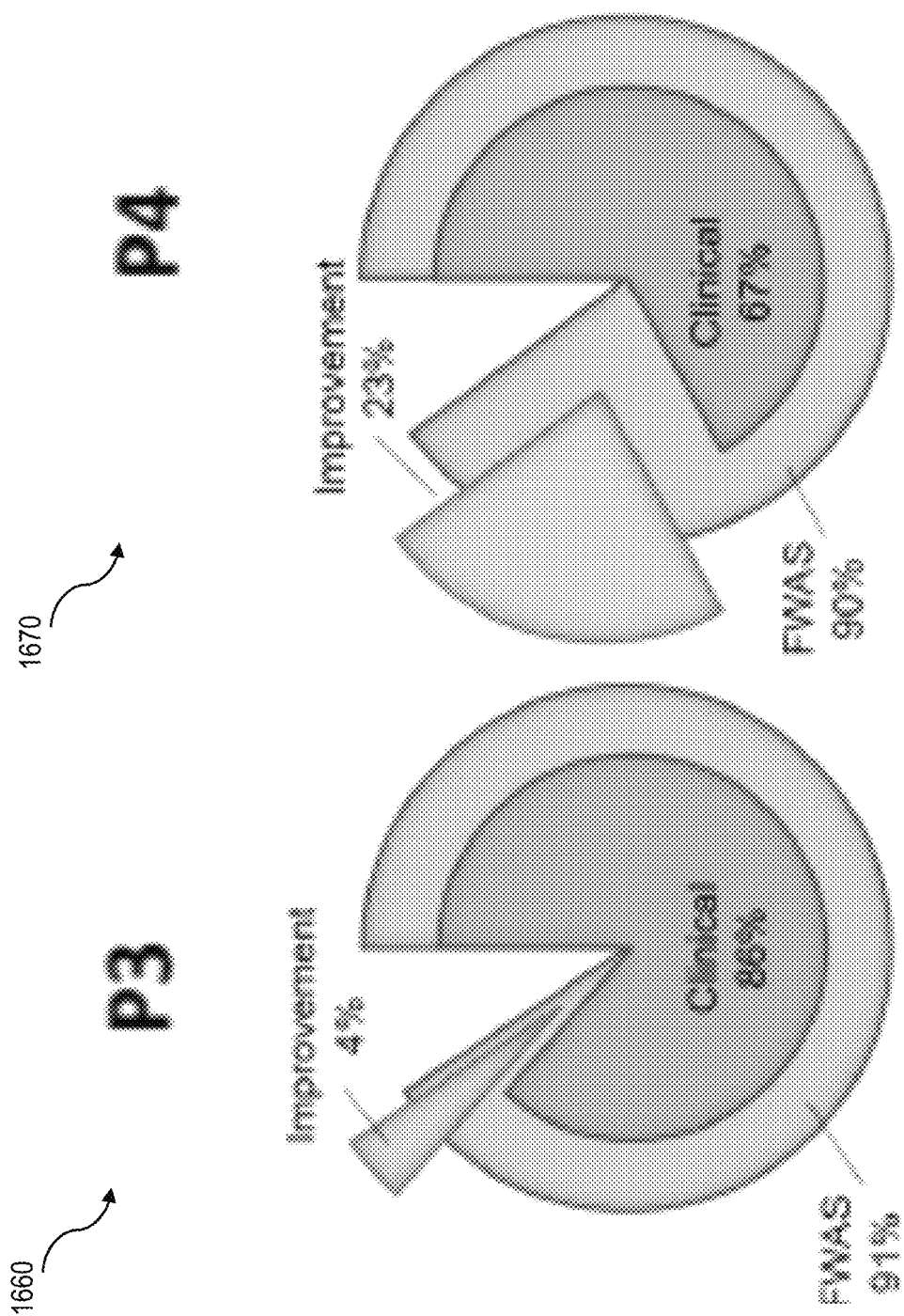

In some embodiments, the dosage level received at airway segments 184 of different diameters is compared between the conventional radiation plan and the RT plan determined by step 518. FIGS. 13A through 13D are graphs that illustrate an example of a maximum dose based on airway segment diameter for different subjects (P1 through P4 from Table 1) using the conventional plan and the plan according to an embodiment. The horizontal axis 1302 of each graph is airway segment diameter in units of millimeters (mm). The vertical axis 1304 is maximum dose $D_{max}$ in units of gray (Gy). The graph 1300 of FIG. 13A is for a first subject (P1 from Table 1) and depicts bars 1308a that represent the maximum dose received at airway segments of different diameter according to the conventional radiation plan and corresponding dots 1306a that represent the maximum dose received at airway segments of different diameters according to the radiation plan according to the present invention. In one embodiment, the graph 1300 indicates that for a vast majority of the airway segment diameters along the axis 1302, the maximum dose (dots 1306a) for the radiation plan according to the present invention is less than the maximum dose (bars 1308a) for the conventional radiation plan. Additionally, the graph 1300 represents a maximum dose constraint 1310a whose value is calculated based on equation 11. Graphs 1310, 1320, 1330 of FIGS. 13B through 13D achieve similar findings for three other patients (P2, P3, P4 from Table 1). In one example embodiment, except for the cases where the dose value is too high (e.g. the airway segment 205 is quite close to the PTV), the optimization process used in step 518 efficiently reduces the dose under the dose constraint.

In some embodiments, the probability of collapse $Pr_{coll}$ of the airway segments 184 is compared between the conventional radiation plan and the RT plan determined in step 518. In one embodiment, a statistical correlation is obtained between a reduction in the probability of airway collapse $Pr_{coll}$ with the term $w_j \times (D_j - D_j^c)^2$ from equation 6 that includes the airway segments 184 as OARs in the optimization process. This term $w_j \times (D_j - D_j^c)^2$ represents the square of the clinical overdose/underdose weighted by the utility measurement of the airway segment. The reduction in probability of collapse, $\Delta Pr_{coll}$ is defined as:

$$\Delta Pr_{coll}[\%] = Pr_{coll}^{cl}[\%] - Pr_{coll}[\%] \tag{12}$$

Where $Pr_{coll}^{cl}$ is the probability of airway segment collapse calculated with equation 3 under a conventional clinical radiation plan and $Pr_{coll}$ is the probability of airway segment collapse calculated with the maximum dose delivered to the airway segment using the RT plan of step 518. This is demonstrated in FIGS. 14A through 14E which analyzes a statistical correlation of the reduction in the airway segment collapse $\Delta Pr_{coll}$ with the term $w_j \times (D_j - D_j^c)^2$.

FIGS. 14A through 14E are graphs that illustrate an example of a reduction in airway collapse probability for different subjects (P1 through P4 of Table 1) using the conventional plan and the plan according to an embodiment. FIGS. 14A through 14D demonstrate that the optimization process used in step 518 reduces the probability of collapse in most of the overdosed airways (dots 1408 in each graph) and does not change the probability (or the changes are very small, as side effects of dose redistribution) of underdosed airways (triangles 1406 in each graph). However, there are some overdosed cases with no reduction in the probability of collapse or the reduction is lower than expected. These cases are showed as crosses 1410 in the graphs. The reason for these cases is that these airway segments 184 are close (e.g. <5 mm) or inside the volume delimited by the PTV. Accordingly, reduction of the maximum dose (and therefore reduction in the probability of collapse) in these airway segments is not possible without compromising PTV coverage. For the airways located further (e.g. ≥5 mm) from the PTV (dots 1408), a monotonic (positive) quasilinear correlation between the reduction in $Pr_{coll}$ and the mentioned term of equation 6. This means that the higher the overdose in a high-functional airway in a conventional plan (weighted by $w_1$), the higher the reduction in $Pr_{coll}$ achieved by the plan described in this invention. This is better shown in FIG. 14E where the data from each of the four subjects (P1 through P4) are plotted together. Spearman and Pearson correlation coefficients were calculated for each patient and for all the subjects (P1 through P4) together and are presented in Table 2.

TABLE 2

| | Correlation coefficients | | | |
|---|---|---|---|---|
| | Spearman | | Pearson | |
| | $r_s$ | p-value | $r_p$ | p-value |
| P1 | 0.62 | 0.01 | 0.62 | 0.01 |
| P2 | 0.94 | <1 × 10$^{-20}$ | 0.97 | 5 × 10$^{-6}$ |

TABLE 2-continued

| | Correlation coefficients | | | |
|---|---|---|---|---|
| | Spearman | | Pearson | |
| | $r_s$ | p-value | $r_p$ | p-value |
| P3 | 0.98 | $<1 \times 10^{-20}$ | 0.98 | $2 \times 10^{-9}$ |
| P4 | 0.78 | $2 \times 10^{-7}$ | 0.67 | $6 \times 10^{-6}$ |
| All patients | 0.79 | $<1 \times 10^{-20}$ | 0.82 | $9 \times 10^{-20}$ |

Highly significant (e.g. p≤0.01) values in Spearman coefficients (0.62-0.98) confirm the monotonic behavior, and highly significant (e.g. p≤0.01) values in Pearson coefficients (0.62-0.98) confirmed the linear correlation.

The preservation of airway flow (e.g. at the terminal airway segments 184) and/or the preservation of total ventilation (e.g. at the dependent lung volumes 189) is also utilized to compare the conventional radiation plan with the RT plan from step 518. The method according to the present invention is analyzed in FIGS. 15A through 15H, where the airflow at terminal airway segments (FIGS. 15A through 15D) and the related ventilation preservation (FIGS. 15E through 15H) are analyzed after radiation therapy for the four subjects (P1 through P4). The horizontal axis 1502 is a probably of no airway collapse ($Pr_{op}=1-Pr_{coll}$) expressed in percentage (%). The vertical axis 1504 in FIGS. 15A through 15D is airflow preservation (through terminal airway segments) expressed in a percentage (%) defined as a difference between the airflow before and after the radiation plan. The vertical axis 1514 in FIGS. 15E through 15H is ventilation preservation (at volumes 189) expressed in a percentage (%) and defined as the ventilation preserved due to airway preservation. The left bar at each $Pr_{op}$ value along the axis 1502 indicates a value of the airway or ventilation preservation for the convention plan and the right bar at each $Pr_{op}$ value indicates a value of the airway or ventilation preservation for the plan according to the present invention. The vertical axis 1506 in FIGS. 15A through 15D is the improvement in the airflow preservation expressed in a percentage (%) and defined as the difference between the airflow preservation between the conventional and the RT plan from step 518 for each value along the axis 1502. The vertical axis 1516 of FIGS. 15E through 15H is the improvement in the ventilation preservation expressed in a percentage (%) and defined as the difference between the ventilation preservation between the conventional and RT plan from step 518 for each value along the axis 1502. Curves 1510 in FIGS. 15A through 15H indicate the value of the improvement in the airflow preservation (FIGS. 15A through 15D) and/or the value of the improvement in the ventilation preservation.

In FIGS. 15A through 15D the value of airflow preservation is presented and in FIGS. 15E through 15H the value of ventilation preservation is presented for several probability levels of no airway collapse ($Pr_{op}=1-Pr_{coll}$), ranging from 30% to 98.5%. $Pr_{op}=30\%$ is the lower threshold for which airflow and ventilation preservation were 100% for both plans in all subjects. $Pr_{op}>98.5\%$ results are not shown in the figures, because airflow and ventilation preservation were very low for both methods. The values estimated for $Pr_{op}=95\%$ are highlighted at region 1508 in each figure, since in one embodiment this threshold value was used to calculate the airway segment dose constraints (equation 6) used in the optimization process of the method of the present invention. In order for an airway segment 184 to be considered open for purposes of both plans, the probability of no collapse for that airway segment 184 has to be greater than the threshold probability value along the axis 1502. Thus, as expected, the higher the probability of no collapse threshold applied to estimate airway segment collapse, the lower the estimated lung function (e.g. airflow and ventilation) for both plans. This is due to the higher probability of no collapse threshold value causing fewer airway segments 184 to be considered open and thus contributing to the airway and/or ventilation for that respective plan. However, the plan of the present invention provided higher lung function than the clinical plan, as indicated by the curve 1510 in each figure showing higher improvements for higher values of $Pr_{op}$. An exception is observed in FIG. 15A (P1) where, some airway segments increased their maximum delivered dose in the plan according to the present invention under the dose constraint (calculated for the 95% threshold), in order to reduce the dose in other overdosed airways. This was a difficult optimization problem in this subject (P1) because the PTV was large and close to the central airways.

For a better visualization of the airflow and ventilation results for $Pr_{op}=95\%$, pie charts 1600 through 1670 are presented in FIGS. 16A through 16H. It was observed that the plan determined according to the present invention ("FWAS" in FIGS. 16A through 16H) provides higher values of airflow at terminal airways and therefore ventilation for the four patients.

3. HARDWARE OVERVIEW

FIG. 17 is a block diagram that illustrates a computer system 1700 upon which an embodiment of the invention may be implemented. Computer system 1700 includes a communication mechanism such as a bus 1710 for passing information between other internal and external components of the computer system 1700. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 1700, or a portion thereof, constitutes a means for performing one or more steps of one or more methods described herein.

A sequence of binary digits constitutes digital data that is used to represent a number or code for a character. A bus 1710 includes many parallel conductors of information so that information is transferred quickly among devices coupled to the bus 1710. One or more processors 1702 for processing information are coupled with the bus 1710. A processor 1702 performs a set of operations on information. The set of operations include bringing information in from the bus 1710 and placing information on the bus 1710. The set of operations also typically include comparing two or more units of information, shifting positions of units of information, and combining two or more units of information, such as by addition or multiplication. A sequence of operations to be executed by the processor 1702 constitutes computer instructions.

Computer system 1700 also includes a memory 1704 coupled to bus 1710. The memory 1704, such as a random access memory (RAM) or other dynamic storage device, stores information including computer instructions. Dynamic memory allows information stored therein to be changed by the computer system 1700. RAM allows a unit of information stored at a location called a memory address to be stored and retrieved independently of information at neighboring addresses. The memory 1704 is also used by the processor 1702 to store temporary values during execution of computer instructions. The computer system 1700 also includes a read only memory (ROM) 1706 or other static storage device coupled to the bus 1710 for storing static information, including instructions, that is not changed by the computer system 1700. Also coupled to bus 1710 is a non-volatile (persistent) storage device 1708, such as a magnetic disk or optical disk, for storing information, including instructions, that persists even when the computer system 1700 is turned off or otherwise loses power.

Information, including instructions, is provided to the bus 1710 for use by the processor from an external input device 1712, such as a keyboard containing alphanumeric keys operated by a human user, or a sensor. A sensor detects conditions in its vicinity and transforms those detections into signals compatible with the signals used to represent information in computer system 1700. Other external devices coupled to bus 1710, used primarily for interacting with humans, include a display device 1714, such as a cathode ray tube (CRT) or a liquid crystal display (LCD), for presenting images, and a pointing device 1716, such as a mouse or a trackball or cursor direction keys, for controlling a position of a small cursor image presented on the display 1714 and issuing commands associated with graphical elements presented on the display 1714.

In the illustrated embodiment, special purpose hardware, such as an application specific integrated circuit (IC) 1720, is coupled to bus 1710. The special purpose hardware is configured to perform operations not performed by processor 1702 quickly enough for special purposes. Examples of application specific ICs include graphics accelerator cards for generating images for display 1714, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1700 also includes one or more instances of a communications interface 1770 coupled to bus 1710. Communication interface 1770 provides a two-way communication coupling to a variety of external devices that operate with their own processors, such as printers, scanners and external disks. In general, the coupling is with a network link 1778 that is connected to a local network 1780 to which a variety of external devices with their own processors are connected. For example, communication interface 1770 may be a parallel port or a serial port or a universal serial bus (USB) port on a personal computer. In some embodiments, communications interface 1770 is an integrated services digital network (ISDN) card or a digital subscriber line (DSL) card or a telephone modem that provides an information communication connection to a corresponding type of telephone line. In some embodiments, a communication interface 1770 is a cable modem that converts signals on bus 1710 into signals for a communication connection over a coaxial cable or into optical signals for a communication connection over a fiber optic cable. As another example, communications interface 1770 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 1770 sends and receives electrical, acoustic or electromagnetic signals, including infrared and optical signals, that carry information streams, such as digital data.

The term computer-readable medium is used herein to refer to any medium that participates in providing information to processor 1702, including instructions for execution. Such a medium may take many forms, including, but not limited to, non-volatile media, volatile media and transmission media. Non-volatile media include, for example, optical or magnetic disks, such as storage device 1708. Volatile media include, for example, dynamic memory 1704. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 1702, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 1702, except for carrier waves and other signals.

Logic encoded in one or more tangible media includes one or both of processor instructions on a computer-readable storage media and special purpose hardware, such as ASIC *1720.

Network link 1778 typically provides information communication through one or more networks to other devices that use or process the information. For example, network link 1778 may provide a connection through local network 1780 to a host computer 1782 or to equipment 1784 operated by an Internet Service Provider (ISP). ISP equipment 1784 in turn provides data communication services through the public, world-wide packet-switching communication network of networks now commonly referred to as the Internet 1790. A computer called a server 1792 connected to the Internet provides a service in response to information received over the Internet. For example, server 1792 provides information representing video data for presentation at display 1714.

The invention is related to the use of computer system 1700 for implementing the techniques described herein. According to one embodiment of the invention, those techniques are performed by computer system 1700 in response to processor 1702 executing one or more sequences of one or more instructions contained in memory 1704. Such instructions, also called software and program code, may be read into memory 1704 from another computer-readable medium such as storage device 1708. Execution of the sequences of instructions contained in memory 1704 causes processor 1702 to perform the method steps described herein. In alternative embodiments, hardware, such as application specific integrated circuit 1720, may be used in place of or in combination with software to implement the invention. Thus, embodiments of the invention are not limited to any specific combination of hardware and software.

The signals transmitted over network link 1778 and other networks through communications interface 1770, carry information to and from computer system 1700. Computer system 1700 can send and receive information, including program code, through the networks 1780, 1790 among others, through network link 1778 and communications interface 1770. In an example using the Internet 1790, a server 1792 transmits program code for a particular application, requested by a message sent from computer 1700, through Internet 1790, ISP equipment 1784, local network 1780 and communications interface 1770. The received code may be executed by processor 1702 as it is received, or may be stored in storage device 1708 or other non-volatile storage for later execution, or both. In this manner, computer system 1700 may obtain application program code in the form of a signal on a carrier wave.

Various forms of computer readable media may be involved in carrying one or more sequence of instructions or data or both to processor 1702 for execution. For example, instructions and data may initially be carried on a magnetic disk of a remote computer such as host 1782. The remote computer loads the instructions and data into its dynamic memory and sends the instructions and data over a telephone line using a modem. A modem local to the computer system 1700 receives the instructions and data on a telephone line and uses an infra-red transmitter to convert the instructions and data to a signal on an infra-red a carrier wave serving as the network link 1778. An infrared detector serving as communications interface 1770 receives the instructions and data carried in the infrared signal and places information representing the instructions and data onto bus 1710. Bus 1710 carries the information to memory 1704 from which processor 1702 retrieves and executes the instructions using some of the data sent with the instructions. The instructions and data received in memory 1704 may optionally be stored on storage device 1708, either before or after execution by the processor 1702.

FIG. 18 illustrates a chip set 1800 upon which an embodiment of the invention may be implemented. Chip set 1800 is programmed to perform one or more steps of a method described herein and includes, for instance, the processor and memory components described with respect to FIG. 1A incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 1800, or a portion thereof, constitutes a means for performing one or more steps of a method described herein.

In one embodiment, the chip set 1800 includes a communication mechanism such as a bus 1801 for passing information among the components of the chip set 1800. A processor 1803 has connectivity to the bus 1801 to execute instructions and process information stored in, for example, a memory 1805. The processor 1803 may include one or more processing cores with each core configured to perform independently. A multi-core processor enables multiprocessing within a single physical package. Examples of a multi-core processor include two, four, eight, or greater numbers of processing cores. Alternatively or in addition, the processor 1803 may include one or more microprocessors configured in tandem via the bus 1801 to enable independent execution of instructions, pipelining, and multithreading. The processor 1803 may also be accompanied with one or more specialized components to perform certain processing functions and tasks such as one or more digital signal processors (DSP) 1807, or one or more application-specific integrated circuits (ASIC) 1809. A DSP 1807 typically is configured to process real-world signals (e.g., sound) in real time independently of the processor 1803. Similarly, an ASIC 1809 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 1803 and accompanying components have connectivity to the memory 1805 via the bus 1801. The memory 1805 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 1805 also stores the data associated with or generated by the execution of one or more steps of the methods described herein.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article. As used herein, unless otherwise clear from the context, a value is "about" another value if it is within a factor of two (twice or half) of the other value. While example ranges are given, unless otherwise clear from the context, any contained ranges are also intended in various embodiments. Thus, a range from 0 to 10 includes the range 1 to 4 in some embodiments.

4. REFERENCES

[1] World Wide Web domain slicer in top level domain org.
[2] World Wide Web domain chestimagingplatform in top level domain org.
[3] Graham M W, Gibbs J D, Cornish D C and Higgins W E 2010 Robust 3-D Airway Tree Segmentation for Image-Guided Peripheral Bronchoscopy *IEEE Transactions on Medical Imaging* 29 982-97.
[4] Ref. Phys. Med Biol. 1999 44(11):R99; 155, *Dose calculations from external photon beams in radiotherapy*, Ahnnesio A. Aspradakis, M M.
[5] Modiri A, Gu X, Hagan A, Bland R, Iyengar P, Timmerman R and Sawant A 2016 Inverse 4D conformal planning for lung SBRT using particle swarm optimization *Physics in Medicine & Biology* 61 6181

[6] Aaron H, Amit S, Michael F and Arezoo M 2018 Multi-GPU configuration of 4D intensity modulated radiation therapy inverse planning using global optimization *Physics in Medicine & Biology* 63 025028

What is claimed is:

1. A method comprising:
   determining a plurality of first subsets of a plurality of voxels in a reference frame of a radiation device that emits a beam of radiation with controlled intensity and beam cross sectional shape, wherein each first subset is based on an anatomical parameter of a respective branching structure of a set of branching structures indicated by measurements from an imaging device that indicate a tissue type inside a subject at each voxel of the plurality of voxels;
   determining a second subset of the plurality of voxels, wherein the second subset encloses an organ-at-risk (OAR) volume and the second subset is associated with one or more first subsets;
   determining, on a processor, data that indicates a series of beam shapes and intensities from the radiation device which minimize a value of an objective function that is based on a computed dose delivered to a voxel summed over all voxels; and
   controlling the radiation device to deliver the series of beam shapes and intensities based on the determined data.

2. A method as recited in claim 1, further comprising:
   determining a location of each voxel of the plurality of voxels in the reference frame of the radiation device that emits the beam of radiation with controlled intensity and beam cross sectional shape;
   obtaining the measurements that indicate the tissue type inside the subject at each voxel of the plurality of voxels based on the imaging device; and
   determining a third subset of the plurality of voxels, wherein the third subset encloses a target volume to be irradiated with a therapeutic dose of radiation by the radiation device.

3. A method as recited in claim 1, further comprising determining on a processor a value of a utility measure at each voxel of the plurality of voxels based on a tissue type for the voxel based on the imaging device, wherein the objective function is further based on the value of the utility measure for each voxel.

4. A method as recited in claim 3, wherein the determining the value of the utility measure comprises determining a value of a first utility measure wi at each voxel of the second subset of voxels based on a corresponding value of the measurements of the second subset of voxels;
   and wherein the objective function is based on a computed dose delivered to each voxel of the second subset of voxels multiplied by the value of the first utility measure for that voxel summed over all voxels of the second subset.

5. A method as recited in claim 3, wherein the determining the value of the utility measure comprises determining a value of a second utility measure $w_j$ at each first subset based on the value of the anatomical parameter of the respective first subset;
   and wherein the objective function is further based on a computed dose delivered to each first subset multiplied by the value of the second utility measure for that first subset summed over all first subsets.

6. A method as recited in claim 5, further comprising determining a value of a cumulative ventilation for each first subset based on a total number of voxels in one or more second subsets of voxels associated with the first subset;
   and wherein the determining the value of the second utility measure $w_j$ at each first subset is further based on the value of the cumulative ventilation for each first subset.

7. A method as recited in claim 6, wherein the determining the value of the second utility measure $w_j$ at each first subset is further based on a value of a first utility measure $w_i$ at each voxel of the total number of voxels, wherein the first utility measure $w_i$ is based on a corresponding value of the measurements for the total number of voxels.

8. A method as recited in claim 1 wherein the imaging device is an X-ray Computed tomography (CT) scanner; and
   wherein the method further comprises obtaining the measurements that indicate the tissue type inside the subject at each voxel of the plurality of voxels based on the imaging device, wherein the obtaining the measurements includes generating a CT image with the CT scanner at one or more phases of the breathing cycle, wherein the determining the plurality of first subsets comprises using the CT image to segment the set of branching structures and determining the second subset comprises using the CT image to segment one or more OAR volumes.

9. A method as recited in claim 8, wherein the CT image is a breath-hold CT (BHCT) image of a lung of the subject, wherein the determining the plurality of first subsets comprises using the BHCT image to segment a set of branching airways of the lung into a plurality of airway segments and wherein the determining the second subset comprises using the BHCT image to segment the lung into a plurality of lobes and to further segment each lobe into one or more sublobes and to further segment each sublobe into the one or more OAR volumes.

10. A method as recited in claim 4 wherein the value of the first utility measure wi is based on the measurements at a first phase of a breathing cycle that indicates a first quantity of the second subset of voxels that enclose the OAR volume at the first phase and the measurements at a second phase of the breathing cycle that indicates a second quantity of the second subset of voxels that enclose the OAR volume at the second phase.

11. A method as recited in claim 1 wherein the set of branching structures is a set of branching airways within a lung of the subject and wherein the OAR volume is downstream of one or more branching airways; and
    wherein the anatomical parameter is a diameter of each branching airway in the set of branching airways.

12. A method as recited in claim 1,
    wherein each first subset of voxels encloses the respective branching structure, wherein the minimization of the objective function is subject to a maximum constraint on the computed dose to each first subset of voxels and wherein the maximum constraint is based on a maximum value of a probability of collapse of the branching structure enclosed by the first subset of voxels; and
    wherein the maximum constraint is further based on the value of the anatomical parameter of the branching structure.

13. A method as recited in claim 12, further comprising:
    determining a location of each voxel of the plurality of voxels in the reference frame of the radiation device that emits the beam of radiation with controlled intensity and beam cross sectional shape;

obtaining the measurements that indicate the tissue type inside the subject at each voxel of the plurality of voxels based on the imaging device; and determining a third subset of the plurality of voxels, wherein the third subset encloses a target volume to be irradiated with a therapeutic dose of radiation by the radiation device.

14. A method as recited in claim 12, further comprising determining on a processor a value of a utility measure at each voxel of the plurality of voxels based on a tissue type for the voxel based on the imaging device, wherein the objective function is further based on the value of the utility measure for each voxel.

15. A method as recited in claim 5, further comprising obtaining the measurements that indicate the tissue type inside the subject at each voxel of the plurality of voxels based on the imaging device;

wherein the obtaining the measurements is performed at multiple phases of the breathing cycle to indicate the plurality of first subsets of voxels occupied by the respective set of branching structures at each phase of the breathing cycle;

wherein the minimizing of the objective function is performed for each branching structure and comprises calculating a received dose at the branching structure at each phase of the breathing cycle based on the plurality of first subsets of voxels at each phase of the breathing cycle to determine a dose delivered to the branching structure at each phase of the breathing cycle; and wherein the computed dose of the objective function delivered to each first subset of voxels is based on an average of the determined doses delivered to each branching structure for the multiple phases of the breathing cycle.

16. A method as recited in claim 15, wherein the obtaining the measurements includes obtaining a four-dimensional high resolution computed tomography (4D-HRCT) that includes a high resolution (HR) image of the set of branching structures at ten phases of the breathing cycle;

wherein the minimizing of the objective function is performed for each branching structure based on each HR image to determine the dose delivered to the branching structure at each of the ten phases of the breathing cycle; and wherein the computed dose of the objective function delivered to each first subset of voxels is based on the average of the determined doses to each branching structure for the ten phases of the breathing cycle.

17. A method as recited in claim 1, further comprising determining a third subset of the plurality of voxels, wherein the third subset encloses an OAR volume different than the OAR volume enclosed by the second subset and the third subset is not associated with the one or more first subsets.

18. A non-transitory computer-readable medium carrying one or more sequences of instructions, wherein execution of the one or more sequences of instructions by one or more processors causes the one or more processors to perform the steps of:

determining a plurality of first subsets of a plurality of voxels in a reference frame of a radiation device that emits a beam of radiation with controlled intensity and beam cross sectional shape, wherein each first subset is based on an anatomical parameter of a respective branching structure of a set of branching structures indicated by measurements from an imaging device that indicate a tissue type inside a subject at each voxel of the plurality of voxels;

determining a second subset of the plurality of voxels that enclose an OAR volume, wherein the second subset is associated with one or more first subsets;

determining data that indicates a series of beam shapes and intensities from a radiation device which minimize a value of an objective function that is based on a computed dose delivered to each voxel summed over all voxels; and controlling the radiation device to deliver the series of beam shapes and intensities based on the determined data.

19. A system comprising:

a radiation device to emit a beam of radiation with controlled intensity and beam cross sectional shape in each voxel of a plurality of voxels in a reference frame of the radiation device;

one or more imaging devices to obtain one or more measurements that relate to tissue type inside a subject at each voxel of the plurality of voxels;

at least one processor; and at least one memory including one or more sequence of instructions;

the at least one memory and the one or more sequence of instructions configured to, with the at least one processor, cause the at least one processor;

to determine a plurality of first subsets of the plurality of voxels in the reference frame of the radiation device, wherein each first subset is based on an anatomical parameter of a respective branching structure of a set of branching structures indicated by measurements from the one or more imaging devices that indicate a tissue type inside a subject at each voxel of the plurality of voxels;

to determine a second subset of the plurality of voxels that enclose an organ-at-risk (OAR) volume and the second subset is associated with one or more first subsets;

to determine data that indicates the controlled intensity and beam cross sectional shape in each voxel that minimize a value of an objective function that is based on a computed dose delivered to each voxel summed over all voxels and to control the radiation device to deliver a series of beam shapes and intensities based on the determined data.

20. A system as recited in claim 19 wherein the set of branching structures is a set of branching airways of a lung of the subject and the OAR volume is downstream of one or more branching airways.

* * * * *